United States Patent
Chou et al.

(10) Patent No.: US 12,181,472 B2
(45) Date of Patent: *Dec. 31, 2024

(54) HOMOGENEOUS ASSAY

(71) Applicant: Essenlix Corporation, Monmouth Junction, NJ (US)

(72) Inventors: Stephen Y. Chou, Princeton, NJ (US); Wei Ding, Princeton, NJ (US); Yufan Zhang, Monmouth Junction, NJ (US); Ji Li, Princeton, NJ (US); Ji Qi, Hillsborough, NJ (US); Jun Tian, Belle Mead, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 311 days.

This patent is subject to a terminal disclaimer.

(21) Appl. No.: 16/621,185

(22) PCT Filed: Jun. 12, 2018

(86) PCT No.: PCT/US2018/037168
§ 371 (c)(1),
(2) Date: Dec. 10, 2019

(87) PCT Pub. No.: WO2018/231877
PCT Pub. Date: Dec. 20, 2018

(65) Prior Publication Data
US 2021/0140957 A1 May 13, 2021

Related U.S. Application Data

(60) Provisional application No. 62/518,514, filed on Jun. 12, 2017, provisional application No. 62/523,570, filed on Jun. 22, 2017.

(51) Int. Cl.
G01N 33/543 (2006.01)
G06T 7/00 (2017.01)

(52) U.S. Cl.
CPC . *G01N 33/54386* (2013.01); *G01N 33/54393* (2013.01); *G06T 7/0012* (2013.01);
(Continued)

(58) Field of Classification Search
None
See application file for complete search history.

(56) References Cited

U.S. PATENT DOCUMENTS

| | | |
|---|---|---|
| 3,368,872 A | 2/1968 | Natelson |
| 3,447,863 A | 6/1969 | Patterson |

(Continued)

FOREIGN PATENT DOCUMENTS

| | | |
|---|---|---|
| AU | 198813789 A | 9/1988 |
| AU | 619459 B | 1/1992 |

(Continued)

OTHER PUBLICATIONS

Van Vliet, Dillys et al., Prediction of asthma exacerbations in children by innovative exhaled inflammatory markers: Results of a longitudinal study, Plos One, Mar. 23, 2015, vol. 10. No. 3, e0119434.

(Continued)

*Primary Examiner* — Rebecca M Giere

(57) ABSTRACT

Among other things, the present invention is related to devices and methods of performing biological and chemical assays, such as but not limited to immunoassays and nucleic assay acid, particularly the homogeneous assay that does not use the step of wash and that is fast (e.g. 60 seconds from dropping a sample to displaying results).

160 Claims, 14 Drawing Sheets

(52) U.S. Cl.
CPC ............... *G01N 2333/4737* (2013.01); *G06T 2207/10064* (2013.01); *G06T 2207/30004* (2013.01)

(56) References Cited

U.S. PATENT DOCUMENTS

| | | | |
|---|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Evine et al. |
| 6,016,367 A | 1/2000 | Benedetti et al. |
| 6,017,767 A | 1/2000 | Chandler |
| 6,022,734 A | 2/2000 | Wardlaw |
| 6,083,761 A | 7/2000 | Kedar et al. |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Fichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,945,852 B2 | 2/2015 | Ettlinger et al. |
| 8,974,732 B2 | 3/2015 | Alpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,267,953 B2 | 2/2016 | Upmeier et al. |
| 9,274,094 B2 | 3/2016 | Wardlaw et al. |
| 9,291,617 B2 | 3/2016 | Levine et al. |

(56) References Cited

U.S. PATENT DOCUMENTS

| | | | |
|---|---|---|---|
| 9,322,835 | B2 | 4/2016 | Wardlaw |
| 9,347,962 | B2 | 5/2016 | Salsman |
| 9,354,159 | B2 | 5/2016 | Vaartstra |
| 9,395,365 | B2 | 7/2016 | Levine et al. |
| 9,469,871 | B2 | 10/2016 | Bearinger et al. |
| 9,523,670 | B2 | 12/2016 | Mueller et al. |
| 9,523,682 | B2 | 12/2016 | Huang et al. |
| 9,696,252 | B2 | 7/2017 | Wardlaw |
| 2001/0055882 | A1 | 12/2001 | Ostuni |
| 2002/0164820 | A1 | 11/2002 | Brown |
| 2003/0068614 | A1 | 4/2003 | Cima et al. |
| 2003/0107946 | A1 | 6/2003 | Cosby et al. |
| 2003/0109059 | A1 | 6/2003 | Adrien et al. |
| 2004/0131345 | A1 | 7/2004 | Kylberg et al. |
| 2004/0156755 | A1 | 8/2004 | Levine |
| 2004/0214310 | A1 | 10/2004 | Parker et al. |
| 2004/0259162 | A1 | 12/2004 | Kappel et al. |
| 2005/0026161 | A1 | 2/2005 | Jablonski et al. |
| 2005/0032138 | A1 | 2/2005 | Lathrop et al. |
| 2005/0112277 | A1 | 5/2005 | Banerjee et al. |
| 2005/0158880 | A1 | 7/2005 | Ostuni et al. |
| 2005/0254995 | A1 | 11/2005 | Sostek et al. |
| 2006/0015157 | A1 | 1/2006 | Leong |
| 2006/0051253 | A1 | 3/2006 | Gousepohl |
| 2006/0062440 | A1 | 3/2006 | Hollars et al. |
| 2006/0062695 | A1 | 3/2006 | Haab et al. |
| 2006/0090658 | A1 | 5/2006 | Phillips |
| 2006/0160134 | A1 | 7/2006 | Melker et al. |
| 2007/0087442 | A1 | 4/2007 | Wardlaw |
| 2007/0243117 | A1 | 10/2007 | Wardlaw |
| 2008/0028962 | A1 | 2/2008 | Phillips et al. |
| 2008/0214947 | A1 | 9/2008 | Hunt et al. |
| 2008/0274564 | A1 | 11/2008 | D'Aurora |
| 2008/0286152 | A1 | 11/2008 | Schmidt et al. |
| 2009/0211344 | A1 | 8/2009 | Wang |
| 2009/0227472 | A1 | 9/2009 | Stuelpnagel et al. |
| 2009/0233329 | A1 | 9/2009 | Rodriguez et al. |
| 2009/0246781 | A1 | 10/2009 | Klem et al. |
| 2009/0258371 | A1 | 10/2009 | Wardlaw et al. |
| 2009/0298716 | A1 | 12/2009 | Stuelpnagel et al. |
| 2010/0081583 | A1 | 4/2010 | Shirazi |
| 2010/0085067 | A1 | 4/2010 | Gabriel et al. |
| 2010/0151593 | A1 | 6/2010 | D'Aurora |
| 2010/0216248 | A1 | 8/2010 | Wardlaw |
| 2010/0255605 | A1 | 10/2010 | Wardlaw |
| 2010/0272345 | A1 | 10/2010 | Wardlaw |
| 2010/0273244 | A1 | 10/2010 | Wardlaw |
| 2010/0291562 | A1 | 11/2010 | Adler |
| 2011/0009297 | A1 | 1/2011 | Jones et al. |
| 2011/0206557 | A1 | 8/2011 | Phan et al. |
| 2011/0212462 | A1 | 9/2011 | Duffy et al. |
| 2011/0294198 | A1 | 12/2011 | Wardlaw |
| 2012/0034647 | A1 | 2/2012 | Herzog et al. |
| 2012/0107799 | A1 | 5/2012 | Daum |
| 2012/0108787 | A1 | 5/2012 | Lue |
| 2012/0157332 | A1 | 6/2012 | Kumar et al. |
| 2012/0300293 | A1 | 11/2012 | Selvin et al. |
| 2012/0321518 | A1 | 12/2012 | Ermantraut et al. |
| 2013/0065788 | A1 | 3/2013 | Glezer et al. |
| 2013/0102018 | A1 | 4/2013 | Schentag et al. |
| 2013/0102500 | A1 | 4/2013 | Stumber et al. |
| 2013/0157288 | A1 | 6/2013 | Kilfeather et al. |
| 2013/0209332 | A1 | 8/2013 | Wardlaw |
| 2013/0217049 | A1 | 8/2013 | Anderson et al. |
| 2013/0252847 | A1 | 9/2013 | Mckenna et al. |
| 2013/0265054 | A1 | 10/2013 | Lowery et al. |
| 2013/0309679 | A1 | 11/2013 | Ismagilov et al. |
| 2014/0170642 | A1 | 6/2014 | Huang et al. |
| 2014/0273272 | A1 | 9/2014 | Gayda et al. |
| 2014/0315242 | A1 | 10/2014 | Rodriguez et al. |
| 2014/0323330 | A1 | 10/2014 | Bergo |
| 2014/0368631 | A1 | 12/2014 | Wardlaw et al. |
| 2014/0378320 | A1 | 12/2014 | Hoffmann et al. |
| 2015/0036131 | A1 | 2/2015 | Salsman |
| 2015/0253321 | A1 | 9/2015 | Chou et al. |
| 2015/0317506 | A1 | 11/2015 | Xie et al. |
| 2015/0323519 | A1 | 11/2015 | Wardlaw |
| 2016/0025637 | A1 | 1/2016 | Halverson et al. |
| 2016/0033496 | A1 | 2/2016 | Chou et al. |
| 2016/0245797 | A1 | 8/2016 | Ahmad et al. |
| 2016/0266091 | A1 | 9/2016 | Levine et al. |
| 2017/0021356 | A1 | 1/2017 | Dority et al. |
| 2017/0038401 | A1 | 2/2017 | Holmes et al. |
| 2017/0045504 | A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 101358969 A | 2/2009 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2008135274 A2 | 11/2008 |
| WO | 2009117652 | 9/2009 |
| WO | 2009117664 | 9/2009 |
| WO | 2009117678 | 9/2009 |
| WO | 2009117682 | 9/2009 |
| WO | 2009122159 A2 | 10/2009 |
| WO | 2009124186 | 10/2009 |
| WO | 2009124190 | 10/2009 |
| WO | 2009126800 | 10/2009 |
| WO | 2010115026 | 10/2010 |
| WO | 2011147563 A1 | 12/2011 |
| WO | 2013075031 A1 | 5/2013 |
| WO | 2013126522 A1 | 8/2013 |
| WO | 2014055559 | 4/2014 |
| WO | 2014089468 | 6/2014 |
| WO | 2014183049 | 11/2014 |
| WO | 2014205576 | 12/2014 |
| WO | 2016081941 A1 | 5/2016 |
| WO | 2017027643 A1 | 2/2017 |
| WO | 2017048871 | 3/2017 |
| WO | 2017048871 A1 | 3/2017 |

OTHER PUBLICATIONS

International Report on Patentability for PCT/US2018/037168 established by IPEA/US mailed on Aug. 19, 2019.

HOMOGENEOUS ASSAY

CROSS-REFERENCING

This application is a National Stage entry (§ 371) application of International Application No. PCT/US2018/037168, filed on Jun. 12, 2018, which claims the benefit of U.S. Provisional Patent Application No. 62/518,514, filed on Jun. 12, 2017, and U.S. Provisional Patent Application No. 62/523,570, filed on Jun. 22, 2017, the contents of which are relied upon and incorporated herein by reference in their entirety.

The entire disclosure of any publication or patent document mentioned herein is entirely incorporated by reference.

FIELD

Among other things, the present invention is related to devices and methods of performing biological and chemical assays, such as but not limited to immunoassays and nucleic assay acid.

BACKGROUND

In biological and chemical assays (e.g. diagnostic testing), often a homogeneous assay, which does not need to wash, is preferred. The current invention provides devices and methods for achieving these goals.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means.

DETAILED DESCRIPTION OF EXEMPLARY EMBODIMENTS

Figure 1A:
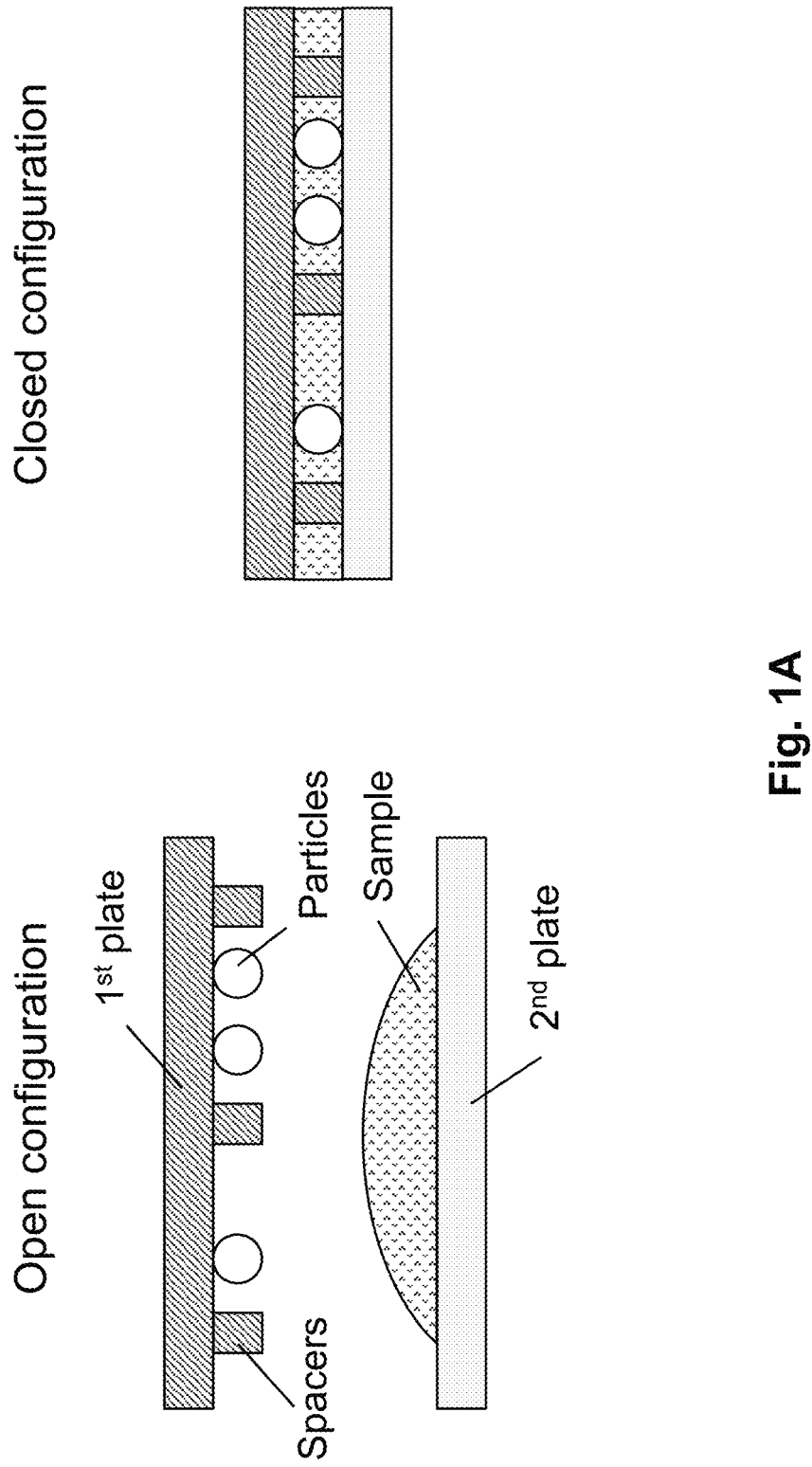
FIG. 1A illustrates open and closed configurations of an exemplary embodiment of the present disclosure.

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It should be noted that the Figures do not intend to show the elements in strict proportion. For clarity purposes, some elements are enlarged when illustrated in the Figures. The dimensions of the elements should be delineated from the descriptions herein provided and incorporated by reference.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The terms "labeled analyte" and "bound label" are interchangeable. The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The terms "unbound label" and "background" are interchangeable, with understanding that the signal of "unbound label" includes signals from other background that are not "unbound label".

The term "lateral area" refers to the area that is in parallel with the plate.

The term "analyte-concentration area" refers to an area of a surface where the area has a higher affinity to bind the labeled analyte/bound label (or to bind an analyte what later binds a label) than the rest area of the surface.

The term "lateral distance between two neighboring analyte concentration areas" or "IACD (inter analyte concentration-area distance)" refers to the distance between the average center of each analyte concentration area. For example, if each of the analyte concentration area has a circular shape in lateral shape, the IACD is the distance between the centers of the two circles. Another example, if each of the two analyte concentration areas is a vertical plane, then the IACD is the lateral distance between the two planes.

The term "diffusion parameter" or "DP" as used herein refers to a parameter that is equal to $\sqrt{Dt}$, wherein D is the diffusion constant of the analyte in the sample and the t is the intended assay time (i.e. the diffusion parameter is equal to the square-root of the diffusion constant of the analyte in the sample multiplying the intended assay time); wherein the intended assay time is a time parameter. For example, if the diffusion constant of the analyte in the sample is $1\times10^{-7}$ cm$^2$/s, the intended assay time is 60 sec, then the diffusion parameter is 24 um (micron). Some of the common analyte diffusion constants are IgG in PBS: $3\times10^{-7}$ cm$^2$/s, IgG in blood: $1\times10^{-7}$ cm$^2$/s, and 20 bp DNA in blood: $4\times10^{-7}$ cm$^2$/s.

The term "bead" as used herein refers to a nano-scale or micro-scale three-dimensional object, regardless of its shape and material. The term "bead" and "particle" is interchangeable.

The term "specifically capture" means that a capture agent selectively bound an analyte that will be detected.

The terms "specific binding" and "selective binding" refer to the ability of a capture agent to preferentially bind to a particular target molecule that is present in a heterogeneous mixture of different target molecule. A specific or selective binding interaction will discriminate between desirable (e.g., active) and undesirable (e.g., inactive) target molecules in a sample, typically more than about 10 to 100-fold or more (e.g., more than about 1000- or 10,000-fold).

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The term "capture agent" as used herein, refers to a binding member, e.g. nucleic acid molecule, polypeptide molecule, or any other molecule or compound, that can specifically bind to its binding partner, e.g., a second nucleic acid molecule containing nucleotide sequences complementary to a first nucleic acid molecule, an antibody that specifically recognizes an antigen, an antigen specifically recognized by an antibody, a nucleic acid aptamer that can specifically bind to a target molecule, etc. A capture agent may concentrate the target molecule from a heterogeneous mixture of different molecules by specifically binding to the target molecule. Binding may be non-covalent or covalent. The affinity between a binding member and its binding partner to which it specifically binds when they are specifically bound to each other in a binding complex is characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower KD.

The term "a secondary capture agent" which can also be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugation (Hermanson, "Bioconjugate Techniques" Academic Press, 2nd Ed., 2008).

The term "capture agent-reactive group" refers to a moiety of chemical function in a molecule that is reactive with capture agents, i.e., can react with a moiety (e.g., a hydroxyl, sulfhydryl, carboxyl or amine group) in a capture agent to produce a stable strong, e.g., covalent bond.

The term "antibody," as used herein, is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (σ), and alpha (α) which encode the IgM, IgD, IgG, IgE, and IgA antibody "isotypes" or "classes" respectively. Antibody herein is meant to include full length antibodies and antibody fragments, and may refer to a natural antibody from any organism, an engineered antibody, or an antibody generated recombinantly for experimental, therapeutic, or other purposes. The term "antibody" includes full length antibodies, and antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies.

The terms "antibody epitope," "epitope," "antigen" are used interchangeably herein to refer to a biomolecule that is bound by an antibody. Antibody epitopes can include proteins, carbohydrates, nucleic acids, hormones, receptors, tumor markers, and the like, and mixtures thereof. An antibody epitope can also be a group of antibody epitopes, such as a particular fraction of proteins eluted from a size exclusion chromatography column. Still further, an antibody epitope can also be identified as a designated clone from an expression library or a random epitope library.

An "allergen," as used herein is a substance that elicits an allergic, inflammatory reaction in an individual when the individual is exposed to the substance, e.g., by skin contact, ingestion, inhalation, eye contact, etc. An allergen may include a group of substances that together elicit the allergic reaction. Allergens may be found in sources classified by the following groups: natural and artificial fibers (cotton, linen, wool, silk, teak, etc., wood, straw, and other dust); tree pollens (alder, birch, hazel, oak, poplar, palm, and others); weeds and flowers (ambrosia, artemisia, and others); grasses and corns (fescue, timothy grass, rye, wheat, corn, bluegrass, and others); drugs (antibiotics, antimicrobial drugs, analgetics and non-steroid anti-inflammatory drugs, anesthetics and muscle relaxants, hormones, and others); epidermal and animal allergens (epithelium of animals, feathers of birds, sera, and others); molds and yeasts (*Penicillium* notation, *Cladosporium* spp., *Aspergillus fumigatus*, *Mucor racemosus*, and others); insect venoms; preservatives (butylparaben, sorbic acid, benzoate, and others); semen (ejaculate); parasitic and mite allergens (ascarids, *Dermatophagoides pteronyssinus*, *Dermatophagoides farinae*, *Euroglyphus maynei*, and others); occupational and hobby allergens (coffee beans, formaldehyde, latex, chloramine, dyes, and others); food allergens (egg products, dairy products and cheeses, meat products, fish and seafood, soy products, mushrooms, flours and cereals, vegetables, melons and gourds, beans, herbs and spices, nuts, citrus and other fruits, berries, teas and herbs, nutritional supplements, and other products), etc.

The term "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these.

As is known to one skilled in the art, hybridization can be performed under conditions of various stringency. Suitable hybridization conditions are such that the recognition interaction between a capture sequence and a target nucleic acid is both sufficiently specific and sufficiently stable. Conditions that increase the stringency of a hybridization reaction are widely known and published in the art. See, for example, Green, et al., (2012), infra.

The term "protein" refers to a polymeric form of amino acids of any length, i.e. greater than 2 amino acids, greater than about 5 amino acids, greater than about 10 amino acids, greater than about 20 amino acids, greater than about 50 amino acids, greater than about 100 amino acids, greater than about 200 amino acids, greater than about 500 amino acids, greater than about 1000 amino acids, greater than about 2000 amino acids, usually not greater than about 10,000 amino acids, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Also included by these terms are polypeptides that are post-translationally modified in a cell, e.g., glycosylated, cleaved, secreted, prenylated, carboxylated, phosphorylated, etc., and polypeptides with secondary or tertiary structure, and polypeptides that are strongly bound, e.g., covalently or non-covalently, to other moieties, e.g., other polypeptides, atoms, cofactors, etc.

The term "complementary" as used herein refers to a nucleotide sequence that base-pairs by hydrogen bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarily may be calculated to assess the possibility of a non-specific (off-target) binding. In general, a complementary of 50% or less does not lead to non-specific binding. In addition, a complementary of 70% or less may not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 200 nucleotides and up to 300 nucleotides in length, or longer, e.g., up to 500 nucleotides in length or longer. Oligonucleotides may be synthetic and, in certain embodiments, are less than 300 nucleotides in length.

The term "attaching" as used herein refers to the strong, e.g., covalent or non-covalent, bond joining of one molecule to another.

The term "surface attached" as used herein refers to a molecule that is strongly attached to a surface.

The term "sample" as used herein relates to a material or mixture of materials containing one or more analytes or entity of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The term "analyte" refers to a molecule (e.g., a protein, peptides, DNA, RNA, nucleic acid, or other molecule), cells, tissues, viruses, and nanoparticles with different shapes.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminescence. An external excitation can be a combination of the above.

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wiley & Sons, 2002).

The term "specific binding conditions" and "conditions suitable for binding," as used herein with respect to binding of a capture agent to an analyte, e.g., a biomarker, a biomolecule, a synthetic organic compound, an inorganic compound, etc., refers to conditions that produce nucleic acid duplexes or, protein/protein (e.g., antibody/antigen) complexes, protein/compound complexes, aptamer/target complexes that contain pairs of molecules that specifically bind to one another, while, at the same time, disfavor to the formation of complexes between molecules that do not specifically bind to one another. Specific binding conditions are the summation or combination (totality) of both hybridization and wash conditions, and may include a wash and blocking steps, if necessary. For nucleic acid hybridization, specific binding conditions can be achieved by incubation at 42° C. in a solution: 50 formamide, 5×SSC (150 mM NaCl, 15 mM trisodium citrate), 50 mM sodium phosphate (pH7.6), 5×Denhardt's solution, 10% dextran sulfate, and 20 ug/ml denatured, sheared salmon sperm DNA, followed by washing the filters in 0.1×SSC at about 65° C.

For binding of an antibody to an antigen, specific binding conditions can be achieved by blocking a first plate containing antibodies in blocking solution (e.g., PBS with 3% BSA or non-fat milk), followed by incubation with a sample containing analytes in diluted blocking buffer. After this incubation, the first plate is washed in washing solution (e.g. PBS+TWEEN 20) and incubated with a secondary capture antibody (detection antibody, which recognizes a second site in the antigen). The secondary capture antibody may be conjugated with an optical detectable label, e.g., a fluorophore such as IRDye800CW, Alexa 790, Dylight 800. After another wash, the presence of the bound secondary capture antibody may be detected. One of skill in the art would be knowledgeable as to the parameters that can be modified to increase the signal detected and to reduce the background noise.

A subject may be any human or non-human animal. A subject may be a person performing the instant method, a patient, a customer in a testing center, etc.

An "analyte," as used herein is any substance that is suitable for testing in the present invention.

As used herein, a "diagnostic sample" refers to any biological sample that is a bodily byproduct, such as bodily fluids, that has been derived from a subject. The diagnostic sample may be obtained directly from the subject in the form of liquid, or may be derived from the subject by first placing the bodily byproduct in a solution, such as a buffer. Exemplary diagnostic samples include, but are not limited to, saliva, serum, blood, sputum, urine, sweat, lacrima, semen, feces, breath, biopsies, mucus, etc.

As used herein, an "environmental sample" refers to any sample that is obtained from the environment. An environmental sample may include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. Typically, samples that are not in liquid form are converted to liquid form before analyzing the sample with the present invention.

As used herein, a "foodstuff sample" refers to any sample that is suitable for animal consumption, e.g., human consumption. A foodstuff sample may include raw ingredients, cooked food, plant and animal sources of food, preprocessed food as well as partially or fully processed food, etc. Typically, samples that are not in liquid form are converted to liquid form before analyzing the sample with the present invention.

The term "diagnostic," as used herein, refers to the use of a method or an analyte for identifying, predicting the outcome of and/or predicting treatment response of a disease or condition of interest. A diagnosis may include predicting the likelihood of or a predisposition to having a disease or condition, estimating the severity of a disease or condition, determining the risk of progression in a disease or condition, assessing the clinical response to a treatment, and/or predicting the response to treatment.

A "biomarker," as used herein, is any molecule or compound that is found in a sample of interest and that is known to be diagnostic of or associated with the presence of or a predisposition to a disease or condition of interest in the subject from which the sample is derived. Biomarkers include, but are not limited to, polypeptides or a complex thereof (e.g., antigen, antibody), nucleic acids (e.g., DNA, miRNA, mRNA), drug metabolites, lipids, carbohydrates, hormones, vitamins, etc., that are known to be associated with a disease or condition of interest.

A "condition" as used herein with respect to diagnosing a health condition, refers to a physiological state of mind or body that is distinguishable from other physiological states. A health condition may not be diagnosed as a disease in some cases. Exemplary health conditions of interest include, but are not limited to, nutritional health; aging; exposure to environmental toxins, pesticides, herbicides, synthetic hormone analogs; pregnancy; menopause; andropause; sleep; stress; prediabetes; exercise; fatigue; chemical balance; etc. The term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least 10-8M. A biotin affinity agent may also include a linker, e.g., -LC-biotin, -LC-LC-Biotin, -SLC-Biotin or -PEGn-Biotin where n is 3-12.

The term "streptavidin" refers to both streptavidin and avidin, as well as any variants thereof that bind to biotin with high affinity.

The term "marker", as used in describing a biological sample, refers to an analyte whose presence or abundance in a biological sample is correlated with a disease or condition.

The term "bond" includes covalent and non-covalent bonds, including hydrogen bonds, ionic bonds and bonds produced by van der Waal forces.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

The term "entity" refers to, but not limited to, proteins, peptides, DNA, RNA, nucleic acid, molecules (small or large), cells, tissues, viruses, nanoparticles with different shapes, that would bind to a "binding site". The entity includes the capture agent, detection agent, and blocking agent. The "entity" includes the "analyte", and the two terms are used interchangeably.

The term "binding site" refers to a location on a solid surface that can immobilize "entity" in a sample.

The term "entity partners" refers to, but not limited to proteins, peptides, DNA, RNA, nucleic acid, molecules (small or large), cells, tissues, viruses, nanoparticles with different shapes, that are on a "binding site" and would bind to the entity. The entity, include, but not limited to, capture agents, detection agents, secondary detection agents, or "capture agent/analyte complex".

The term "target analytes" or "target entity" refers to a particular analyte that will be specifically analyzed (i.e. detected), or a particular entity that will be specifically bound to the binding site.

The term "smart phone" or "mobile phone", which are used interchangeably, refers to the type of phones that has a camera and communication hardware and software that can take an image using the camera, manipulate the image taken by the camera, and communicate data to a remote place. In some embodiments, the Smart Phone has a flash light.

The term "light" refers to, unless specifically specified, an electromagnetic radiation with various wavelength.

The term "average linear dimension" of an area is defined as a length that equals to the area times 4 then divided by the perimeter of the area. For example, the area is a rectangle, that has width w, and length L, then the average of the linear dimension of the rectangle is $4*W*L/(2*(L+W))$ (where "*" means multiply and "/" means divide). By this definition, the average line dimension is, respectively, W for a square of a width W, and d for a circle with a diameter d. The area includes, but is not limited to, the area of a binding site or a storage site.

The term "period" of periodic structure array refers to the distance from the center of a structure to the center of the nearest neighboring identical structure.

The term "storage site" refers to a site of an area on a plate, wherein the site contains reagents to be added into a sample, and the reagents are capable of being dissolving into the sample that is in contract with the reagents and diffusing in the sample.

The term "relevant" means that it is relevant to detection of analytes, quantification and/or control of analyte or entity in a sample or on a plate, or quantification or control of reagent to be added to a sample or a plate.

The term "hydrophilic", "wetting", or "wet" of a surface means that the contact angle of a sample on the surface is less than 90 degrees.

The term "hydrophobic", "non-wetting", or "does not wet" of a surface means that the contact angle of a sample on the surface is equal to or larger than 90 degrees.

The term "variation" of a quantity refers to the difference between the actual value and the desired value or the average of the quantity. And the term "relative variation" of a quantity refers to the ratio of the variation to the desired value or the average of the quantity. For example, if the desired value of a quantity is Q and the actual value is (Q+□), then the □ is the variation and the □/(Q+□) is the relative variation. The term "relative sample thickness variation" refers to the ratio of the sample thickness variation to the average sample thickness.

The term "optical transparent" refers to a material that allows a transmission of an optical signal, wherein the term "optical signal" refers to, unless specified otherwise, the optical signal that is used to probe a property of the sample, the plate, the spacers, the scale-marks, any structures used, or any combinations of thereof.

The term "none-sample-volume" refers to, at a closed configuration of a CROF process, the volume between the plates that is occupied not by the sample but by other objects that are not the sample. The objects include, but not limited to, spacers, air bubbles, dusts, or any combinations of thereof. Often none-sample-volume(s) is mixed inside the sample.

The term "saturation incubation time" refers to the time needed for the binding between two types of molecules (e.g. capture agents and analytes) to reach an equilibrium. For a surface immobilization assay, the "saturation incubation time" refers the time needed for the binding between the target analyte (entity) in the sample and the binding site on plate surface reaches an equilibrium, namely, the time after which the average number of the target molecules (the entity) captured and immobilized by the binding site is statistically nearly constant.

In some cases, the "analyte" and "binding entity" and "entity" are interchangeable.

A "processor," "communication device," "mobile device," refer to computer systems that contain basic electronic elements (including one or more of a memory, input-output interface, central processing unit, instructions, network interface, power source, etc.) to perform computational tasks. The computer system may be a general purpose computer that contains instructions to perform a specific task, or may be a special-purpose computer.

A "site" or "location" as used in describing signal or data communication refers to the local area in which a device or subject resides. A site may refer to a room within a building structure, such as a hospital, or a smaller geographically defined area within a larger geographically defined area. A remote site or remote location, with reference to a first site that is remote from a second site, is a first site that is physically separated from the second site by distance and/or by physical obstruction. The remote site may be a first site that is in a separate room from the second site in a building structure, a first site that is in a different building structure from the second site, a first site that is in a different city from the second site, etc.

As used herein, "raw data" includes signals and direct read-outs from sensors, cameras, and other components and instruments which detect or measure properties or characteristics of a sample. For example, raw data includes voltage or current output from a sensor, detector, counter, camera, or other component or device; raw data includes digital or analog numerical output from a sensor, detector, counter, camera, or other component or device; and raw data may include digitized or filtered output from a sensor, detector, counter, camera, or other component or device. For example, raw data includes the output of a luminometer, which may include output in "relative light units" which are related to the number of photons detected by the luminometer. Raw data may include a JPEG, bitmap, or other image file produced by a camera. Raw data may include cell counts; light intensity (at a particular wavelength, or at or within a range of wavelengths); a rate of change of the output of a detector; a difference between similar measurements made at two times; a number of events detected; the number of events detected within a pre-set range or that meet a pre-set criterion; the minimum value measured within a time period, or within a field of view; the maximum value measured within a time period, or within a field of view; and other data. Where sufficient, raw data may be used without further processing or analysis. In other cases, raw data may be further processed or used for further analysis related to the sample, the subject, or for other purposes.

"Representative of a sample" as used in reference to an output signal or raw data that are representative of the sample, refers to the output signal or raw data reflecting a measured property of the sample or a portion thereof, e.g., reflecting the amount of analyte of interest present in the sample. For instance, the intensity of a fluorescence signal representative of a sample may be more intense in a fluorescently labeled sample that contains more analyte of interest than the intensity of a fluorescence signal representative of a fluorescently labeled sample that contains less analyte.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

1. Principles and Certain Examples

One objective of the present invention is to perform a homogeneous assay in "one step". The "one step" assay means that in assaying, one drops a sample on the assay and then reads the signal, and there are no other steps in between (e.g. washing). The assays include, but not limited to, protein assays and nucleic acid assays.

Another objective of the present invention is to perform a "one step" assay in a time frame of about 60 seconds or less. The time is defined as the time from a sample touching the assay plate to the signal of the assay being ready to be read.

The present invention is to allow performing a homogeneous assay in "one-step" without using any washing, often being completed in about 60 seconds or less. In the "one-step" assay, it uses two plates that are movable relative to each other, a sample with an analyte is dropped on one or both of the plates, the two plates are pressed against each other to compress at least a portion of the sample into a thin layer, followed by reading the signal from the plate without any washing. Often the time, from the sample touching one of the plates to reading the signal from the plate is about 60 sec or less.

Another important feature of the present invention is that in certain embodiments, the two plates of the assay are pressed by human hands, and by using particular set of the plates and the spacers, as specified herein, at least a portion of the sample have a uniform thickness.

Another objective of the present invention is to perform homogenous assays, while removing the shortcoming of lateral flow assay (LFA). Particularly, some embodiments of the present inventions that uses CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow") refers to a particular type of COF, wherein the final thickness of a part or entire sample after the compression is "regulated" by spacers, wherein the spacers, that are placed between the two plates.

CROF has a number of advances over LFA, including not limited to:

(1) In LFA, analyte has higher concentration for the particles at the entrance area than that in the end area of a lateral flow. Therefore, LFA often needs to wait for a complete flow and/or check all areas of the device.

In CROF, analyte is more uniformly distributed for each area in a sample layer, partly because CROF change from an open configuration to a closed configuration in seconds and forced by a compressing (i.e. using the fingers to press).

(2) IN LFA, if the beads for capturing are not fixed with a device, the bead may flow with the sample during a sample loading, causing a non-uniformity of the beads (average over an area). But by the nature of the CROF, the beads can have much more uniformly distributed for each area than that LFA.

(3) Because (1) and (2), in CROF, one can pick up certain local areas that should be sufficient to represent entire sample. But in LFA, one may need to measure the entire sample or taking other steps for an accurate measurements.

EXAMPLES

According to one embodiment of the present invention, as shown in FIG. 1, a device for a homogeneous assay, comprising:

a first plate, a second plate, spacers, a plurality of particles, and capture agents, wherein:
 i. the first and second plates are movable relative to each other into different configurations, including an open configuration and a closed configuration;
 ii. each of the plates has, on its respective inner surface, a sample contact area for contacting a sample suspected of containing a analyte;
 iii. the first plate comprises the spacers that are fixed on its inner surface, at least one of the spacers is inside the sample contact area, the spacers have a predetermined substantially uniform height that is equal to 100 um or less;
 iv. the plurality of particles has the capture agents immobilized on their surface, wherein the capture agents are capable of specifically binding and immobilizing the analyte; and
 v. the plurality of particles are (a) distributed on the sample contact area of the first plate, except the areas occupied by the spacers, and (b) are temporarily or permanently fixed on the first plate;
 wherein in the open configuration, the two plates are partially or entirely separated apart, the spacing between the plates is not regulated by the spacers, and the sample is deposited on one or both of the plates; and
 wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

According to one embodiment of the present invention, a device for a homogeneous assay, comprising:
a first plate, a second plate, spacers, a plurality of particles, and capture agents, wherein:
 i. the first and second plates are movable relative to each other into different configurations, including an open configuration and a closed configuration;
 ii. each of the plates has, on its respective inner surface, a sample contact area for contacting a sample suspected of containing a analyte;
 iii. one or both plates comprises the spacers that are fixed on its inner surface, at least one of the spacers is inside the sample contact area, the spacers have a predetermined substantially uniform height that is equal to 100 um or less;
 iv. the plurality of particles has the capture agents immobilized on their surface, wherein the capture agents are capable of specifically binding and immobilizing the analyte; and
 v. the plurality of particles are (a) distributed on a sample contact area of the first, and (b) are temporarily or permanently fixed on the plate;
 wherein in the open configuration, the two plates are partially or entirely separated apart, the spacing between the plates is not regulated by the spacers, and the sample is deposited on one or both of the plates; and
 wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

Another objective of the present invention is to perform homogenous assays accurately by (1) measuring the total optical signal for an particle area and the total optical signal from its neighboring area, and by (2) averaging several pairs of the particle area and its surrounding area.

According to one embodiment of the present invention, a method of performing a homogeneous assay, comprising the steps of:
 (a) obtaining a sample suspected of containing an analyte;
 (b) obtaining a device of any prior embodiment, wherein the capture agents are capable of specifically binding an binding site of the analyte;
 (c) having optical labels on at least a part of the sample contact areas of the device, wherein the optical labels are capable of binding to the analytes;
 (d) depositing the sample on one or both of the plates when the plates are in an open configuration, wherein in an open configuration;
 (e) after (d), bringing the two plates together and pressing the plates into a closed configuration, at least part of the sample is compressed by the two plates into a layer of highly uniform thickness, the uniform thickness of the layer is confined by the inner surfaces of the plates and is regulated by the plates and the spacers;
 (f) while the plates are in the closed configuration, analyzing the analyte in the layer of uniform thickness, wherein the analyzing comprises:
  i. measuring, from outside of the sample layer, the total light signal from (a) a particle area that is an area of the sample layer that contains one particle and from (b) a surrounding area that is the area of the sample layer which is around the particle area, wherein the surrounding area is 50 D within the edge of the particle, wherein the D is the diameter of the particle; and
  ii. measuring the total light signal from each of the particle area and the surrounding area of at least two different particle areas.

According to one embodiment of the present invention, an apparatus for homogenous assaying an analyte in a sample, comprising:
  i. a device of any prior embodiment,
  ii. an imager or imagers that images at least a part of the sample contact area.

According to one embodiment of the present invention, a smartphone system for homogeneous assay, comprising:
  (a) a device of any prior embodiment;
  (b) a mobile communication device that comprises:
    i. one or a plurality of cameras for detecting and/or imaging the sample;
    ii. electronics, signal processors, hardware and software for receiving and/or processing the detected signal and/or the image(s) of the sample and for remote communication; and
  (c) an adaptor that is configured to accommodate the device that is in the closed configuration and be engageable to the mobile communication device;
  wherein when engaged with the mobile communication device, the adaptor is configured to facilitate the detection and/or imaging of the analyte in the sample.

The device of any prior embodiment, wherein the distribution of the plurality of particles on the plate is random.

The device of any prior embodiment, wherein the plurality of particles are fixed on the plate and has periodic distribution.

The device of any prior embodiment, wherein the spacer has a flat top.

The device of any prior embodiment, wherein the plurality of particles is temporarily fixed on the first plate, and in an open configuration the sample is deposited first on the first plate before the two plates being bought into the closed configuration.

The device of any prior embodiments, wherein the thickness of the spacer is configured, so that in a closed configuration, for a certain concentration of the analytes in the sample, at least one area of the uniform thickness sample that contains one of the particle becomes optically distinguishable, when viewed outside of the sample layer, from its neighboring area that does not contain a particle.

The device of any prior embodiment, the device comprising two plates and spacers, wherein the pressing is by human hand.

The device of any prior embodiment, the device comprising two plates and spacers, wherein at least a portion of the inner surface of one plate or both plate is hydrophilic.

The device of any prior embodiment, the device comprising two plates and spacers, wherein the inter spacer distance is periodic.

The device of any prior embodiment, the device comprising two plates and spacers, wherein the sample is a deposition directly from a subject to the plate without using any transferring devices.

The device of any prior embodiment, the device comprising two plates and spacers, wherein after the sample deformation at a closed configuration, the sample maintains the same final sample thickness, when some or all of the compressing forces are removed. The device of any prior embodiment, the device comprising two plates and spacers, wherein the spacers have pillar shape and nearly uniform cross-section.

The device of any prior embodiment, the device comprising two plates and spacers, wherein the inter spacer distance (SD) is equal or less than about 120 um (micrometer).

The device of any prior embodiment, the device comprising two plates and spacers, wherein the inter spacer distance (SD) is equal or less than about 100 um (micrometer). The device of any prior embodiment, the device comprising two plates and spacers, wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The device of any prior embodiment, the device comprising two plates and spacers, wherein the fourth power of the inter-spacer-distance (ISD) divided by the thickness (h) and the Young's modulus (E) of the flexible plate ($ISD^4/(hE)$) is $5 \times 10^5$ um3/GPa or less.

The device of any prior embodiment, the device comprising two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device of any prior embodiment, the device comprising two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The device of any prior embodiment, wherein the ratio of the inter-spacing distance of the spacers to the average width of the spacer is 2 or larger, and the filling factor of the spacers multiplied by the Young's modulus of the spacers is 2 MPa or larger.

The method of any prior embodiment, wherein the particle area for the total light signal measurement has substantially the same area as the particle diameter.

The method of any prior embodiment, wherein the particle area for the total light signal measurement is smaller than the area defined by the particle diameter.

The method of any prior embodiment, wherein the analyzing the analyte in the uniform sample layer comprising averaging of the total light signal from each area.

The method of any prior embodiment, wherein the analyzing the analyte in the uniform sample layer comprising (i) taking a ration of the total light signal of each particle area to that of its surrounding area, and (ii) averaging the ratio of all particle area and surround area pairs.

The method of any prior embodiment, wherein the time from the end of the sample deposition to the end of reach a closed configuration is less than 15 seconds.

The method of any prior embodiment, wherein the time from the end of the sample deposition to the end of reach a closed configuration is less than 5 seconds.

The method of any prior embodiment, wherein the surrounding area is 2 D within the edge of the particle.

The method of any prior embodiment, wherein the surrounding area is 5 D within the edge of the particle.

The method of any prior embodiment, wherein the surrounding area is 10 D within the edge of the particle.

The method of any prior embodiment, wherein the surrounding area is 20 D within the edge of the particle.

The method of any prior embodiment, wherein the surrounding area is 50 D within the edge of the particle.

1.1 One Step Assay.

In order to achieve one-step assay that detects an analyte in a sample, a key approach of the present invention is to make the captured analyte "visible" in the sample (i.e. that is distinguishable from the rest of the sample) without any washing. The term "captured analyte" refers to the analyte that is being selectively (i.e. specifically) captured by a capture agent.

A captured analyte can give a signal by (a) being attached to a label that can give a signal, (b) giving a signal on its own, and (c) both (a) and (b). Here we focus on the situation (a), wherein the signal from a captured analyte comes from a light label ("label"), wherein the label is capable of selectively attaching to the analyte using a detection agent, and wherein the detection agent can selectively bind to the analyte. However, the invention equally applies to the situations of (b) and (c).

In a one-step assay for situation (a), the objective is to identify/detect the bound labels that are bound to the analyte (the label is termed "bound label", and the analyte is termed "labeled analyte") from the labels that are not bound to the analyte ("unbound label").

In a one-step assay for situation (b), the objective is to identify/detect the bound analyte (i.e. captured by a capture agent) from the analytes that are not captured by a capture agent ("unbound analyte"). When the principle of situation (a) is used to situation (b), the bond label and unbound label in situation (a) becomes the bound analyte and the unbound analyte in the situation (b).

According to the present invention, the one step assay uses two plates to sandwich a thin layer of a sample that has an analyte between the plates, uses a detector above the sample layer to detect a signal from a label (FIG. 2), and identify bound label from unbound label through one of the following approaches:

(i) concentrating the bound label into a or a plurality of locations in the sample (termed "concentrated location"), while reduce the concentration of the bound label in the other locations of the sample;

(ii) reducing the local background signal at analyte concentration area (C-LBS), wherein the C-LBS is defined as the background signal generate by the sample volume that is in front of the concentration surface (hence the sample volume is equal to the local sample thickness (from the analyte concentration area to the front plate's inner surface) multiplies by the area of the concentration surface at that location. For example, the C-LBS at a location of a concentration protrusion (with only the protrusion top surface has an analyte concentration area) is the background signal in the sample volume, wherein the volume is equal to the distance between the top of the protrusion to the top plate surface multiplying the area of protrusion's top at the interested location. In this example, clearly the higher the protrusion, the smaller the local background volume, and hence the smaller the C-LBS.

(iii) selectively (i.e. only the bound label, not unbound label) attaching the bound label onto an amplification surface, wherein the amplification surface amplifies the signal of a label only when the label is attached to the surface or within a short distance from the surface (e.g. less than 1 um);

(iv) selectively attaching the bound quencher onto a surface with label, wherein the labeling surface reduces the signal only when the quencher is attached to the surface or within a short distance from the surface (e.g. less than 1 um);

(v) a combination of thereof.

A. Concentrating the Labeled Analyte/Bound Label

Example of embodiments of the present invention for concentrating the labeled analyte/bound label are given below.

(1) Concentration surface. A device for concentrating bound label, comprises: two plates (or an enclosed channel) with a sample (that has an analyte) sandwiched between the two plates, wherein one or both of the plates has a analyte concentration area on its inner surface of the plate, wherein the analyte concentration area has an capture agent that selectively binds the bound label directly or indirectly (i.e. the analyte concentration area has a higher affinity to bind the bound label than the rest area of the plate). An indirect binding means that the capture agent captures an analyte, while the analyte is bound to a label (this is most common case).

The term "analyte concentration area" refers to an area of a surface where the area has a higher affinity to bind the labeled analyte/bound label (or to bind an analyte what later binds a label) than the rest area of the surface.

In some embodiments, a concentration surface can be formed by immobilizing capture agent on the concentration surface, wherein the capture agent specifically binds the analyte.

In some embodiments, a concentration surface can be formed by reducing the binding of the analytes in the surfaces other than the concentration surface.

(2) Concentration protrusion (e.g. pillar). A device for concentrating bound label, comprises: two plates (or an enclosed channel) with a sample (that has an analyte) sandwiched between the two plates, wherein one or both of the plates has a or a plurality of protrusions, wherein the protrusion has an analyte concentration area on at least one of the protrusion's surfaces, wherein the analyte concentration area selectively bind the labeled analyte/bound label.

(3) Concentration bead. A device for concentrating labeled analyte/bound label, comprises: two plates (or an enclosed channel) with a sample (that has an analyte) sandwiched between the two plates, wherein one bead or a plurality of beads is placed in the sample, wherein the bead has an analyte concentration area on the bead's surface, wherein the analyte concentration area selectively binds the bound label.

(4) Combination. Any combination of (1)-(3).

B. Making the Captured Analyte (with Label) Visible

When a detector is used to image an optical signal emitting through the front plate of the sample-plate sandwich, a 2D image will be obtained.

In this 2D image, the requirement for making the analyte concentration area (after catching the labeled analyte) visible (i.e. distinguishable) over the background signal from the latera areas that are not analyte concentration area (i.e. non-analyte concentration area local background signal, "NC-LBS") is that the signal from the analyte concentration area plus the C-LBL must be larger than NC-LBS by at least one standard variation of the NC-LBS (This condition is termed "visible condition"). The visible condition can be achieved by (i) increase the signal in the analyte concentration area, (ii) reducing C-LBS, (iii) reducing NC-LBS, or (iv) a combination of thereof.

A visible condition can be achieved by adjusting (i) total label concentration in a sample (since some will form bound label with analyte, and the rest will be unbound become a part of background signal), (ii) the total analyte concentration (i.e. limit of detection), (iii) the area or density of the analyte concentration area, (iv) the distance between the analyte concentration area to the front plate, (v) amplification factor of an amplification surface, (vi) the shape of the concentration/amplification area, (vii) the capture reagent concentration on the concentration/amplification area, (viii) the incubation time, or (ix) a combination thereof.

C. Making Assay Rapid

According to the present invention, an assay can have a short assaying time (i.e. being speeded up) by using the following three approaches: (a) using two plates to sandwich a sample into a thin layer between the plates and by limiting the spacing between the two plates (hence the thickness of at least a port of the sample) into small size (e.g. the spacing is equal to or less than the diffusion parameter (as defined in Definition), since a smaller diffusion parameter will have less diffusion time); (b) making the average lateral distance between two neighboring analyte concentration areas (i.e. inter analyte concentration-area distance (IACD) small (e.g. IACD is equal to or less than 2 times of the diffusion parameter); and (c) (a) and (b).

In certain embodiments, the spacing between the two plate (or the spacer height) is 50 nm, 100 nm, 200 nm, 500 nm, 700 nm, 900 nm, 1 um, 2 um, 3 um, 4 um, 5 um, 6 um, 7 um, 8 um, 9 um, 10 um, 20 um, 30 um, 40 um, 50 um, 60 um, 70 um, 80 um, 90 um, 100 um, 120 um, 150 um, 180 um, 200 um, or in a range between any two of these values.

In some preferred embodiments, the spacing between the two plates (or the spacer height) is 500 nm, 700 nm, 900 nm, 1 um, 2 um, 3 um, 4 um, 5 um, 6 um, 7 um, 8 um, 9 um, 10 um, 20 um, 30 um, 40 um, 50 um, or in a range between any two of these values.

In certain preferred embodiments, the spacing between the two plates (or the spacer height) is 500 nm, 700 nm, 900 nm, 1 um, 2 um, 3 um, 4 um, 5 um, 6 um, 7 um, 8 um, 9 um, 10 um, 20 um, or in a range between any two of these values.

In certain embodiments, the spacing between the two plate (or the spacer height) is 0.01 times of the DP (diffusion parameter), 0.01 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 2.5 times of the DP, 3 times of the DP, 4 times of the DP, 5 times of the DP, or in a range between any two of these values.

In some preferred embodiments, the spacing between the two plates (or the spacer height) is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 2.5 times of the DP, or in a range between any two of these values.

In certain preferred embodiments, the spacing between the two plates (or the spacer height) is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, or in a range between any two of these values.

In certain embodiments, the average IACD is 50 nm, 100 nm, 200 nm, 500 nm, 700 nm, 900 nm, 1 um, 2 um, 3 um, 4 um, 5 um, 6 um, 7 um, 8 um, 9 um, 10 um, 20 um, 30 um, 40 um, 50 um, 60 um, 70 um, 80 um, 90 um, 100 um, 120 um, 150 um, 180 um, 200 um, or in a range between any two of these values.

In some preferred embodiments, the average IACD is 500 nm, 700 nm, 900 nm, 1 um, 2 um, 3 um, 4 um, 5 um, 6 um, 7 um, 8 um, 9 um, 10 um, 20 um, 30 um, 40 um, 50 um, or in a range between any two of these values.

In certain preferred embodiments, the average IACD is 500 nm, 700 nm, 900 nm, 1 um, 2 um, 3 um, 4 um, 5 um, 6 um, 7 um, 8 um, 9 um, 10 um, 20 um, or in a range between any two of these values.

In certain embodiments, the average IACD is 0.01 times of the DP (diffusion parameter), 0.01 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 3 times of the DP, 4 times of the DP, 5 times of the DP, or in a range between any two of these values.

In some preferred embodiments, the average IACD is 0.01 times of the DP (diffusion parameter), 0.01 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 2.5 times of the DP, or in a range between any two of these values.

In certain preferred embodiments, the average IACD is 0.01 times of the DP (diffusion parameter), 0.01 times of the DP, 0.1 times of the DP, 0.3 times of the DP, 0.5 times of the DP, 0.7 times of the DP, 1 times of the DP, 1.2 times of the DP, 1.5 times of the DP, or in a range between any two of these values.

In certain preferred embodiments, the average IACD is 500 nm, 700 nm, 900 nm, 1 um, 2 um, 3 um, 4 um, 5 um, 6 um, 7 um, 8 um, 9 um, 10 um, 20 um, or in a range between any two of these values.

In certain embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, 70 sec, 80 sec, 100 sec, 120 sec, 140 sec, 160 sec, 180 sec, 200 sec, 220 sec, 240 sec, or in a range between any two of these values.

In some preferred embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, 70 sec, 80 sec, 100 sec, 120 sec, 140 sec, 160 sec, 180 sec, or in a range between any two of these values.

In certain preferred embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, 70 sec, 80 sec, 100 sec, 120 sec, or in a range between any two of these values.

In certain preferred embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, or in a range between any two of these values.

In certain embodiments, each of the embodiments has an average IACD and a spacing between the two plate (or a spacer height) that are chosen from the size value or range given in previous paragraphs.

The spacing between the plates can be formed either without using a spacer or with spacers. In some embodiments, the two plates with spacers are parts of a QMAX device (or QMAX card, CROF device, CROF card, which all refer to the same device).

D. Control Plate Spacing and Sample Thickness Using Spacers

According to the present invention, the spacing between the two plates and hence the sample thickness are controlled by using the spacers.

The present invention uses a combination of A to D to achieve a one-step assay. Spacer height. In some embodiments, all spacers have the same pre-determined height. In some embodiments, spacers have different pre-determined heights. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment.

In some embodiments, the spacer height is controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or in a range between any of the values.

In some embodiments, the spacer height, the spacing between the plates, and/or sample thickness is: (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

For example, the red blood cell has a disk shape with a minim dimension of 2 µm (disk thickness) and a maximum dimension of 11 µm (a disk diameter). In an embodiment of the present invention, the spacers are selected to make the inner surface spacing of the plates in a relevant area to be 2 µm (equal to the minimum dimension) in one embodiment, 2.2 µm in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 µm and any number between the two values, an undiluted whole blood sample is confined in the spacing; on average, each red blood cell (RBC) does not overlap with others, allowing an accurate counting of the red blood cells visually. (Too many overlaps between the RBC's can cause serious errors in counting).

In some embodiments, the spacer height, the spacing between the plates, and/or sample thickness is: (i) equal to or smaller than the minimum dimension of an analyte, or (ii) equal to or slightly smaller than the maximum dimension of an analyte. The "slightly smaller" means that it is about 1% to 5% smaller and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

In the present invention, in some embodiments, the plates and the spacers are used to regulate not only the thickness of a sample, but also the orientation and/or surface density of the analytes/entity in the sample when the plates are at the closed configuration. When the plates are at a closed configuration, a thinner thickness of the sample results in less analytes/entity per surface area (i.e. less surface concentration).

Spacer lateral dimension. For an open-spacer, the lateral dimensions can be characterized by its lateral dimension (sometimes called width) in the x and y-two orthogonal directions. The lateral dimension of a spacer in each direction is the same or different. In some embodiments, the lateral dimension for each direction (x or y) is 1 nm or less, 3 nm or less, 5 nm or less, 7 nm or less, 10 nm or less, 20 nm or less, 30 nm or less, 40 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, or 500 µm or less, or in a range between any two of the values.

In some embodiments, the ratio of the lateral dimensions of x toy direction is 1, 1.5, 2, 5, 10, 100, 500, 1000, 10,000, or in a range between any two of the value. In some embodiments, a different ratio is used to regulate the sample flow direction; the larger the ratio, the flow is along one direction (larger size direction).

In some embodiments, different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height of the spacers are substantially the same. In some embodiments, all spacers have the same shape and dimensions. In some embodiments, the spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or in a range between any two of the values.

Inter-spacer distance. The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers is arranged as lattices of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

In some embodiments, the distance between neighboring spacers (i.e. the inter-spacer distance) is 1 µm or less, 5 µm or less, 7 µm or less, 10 µm or less, 20 µm or less, 30 µm or less, 40 µm or less, 50 µm or less, 60 µm or less, 70 µm or less, 80 µm or less, 90 µm or less, 100 µm or less, 200 µm or less, 300 µm or less, 400 µm or less, or in a range between any two of the values.

In certain embodiments, the inter-spacer distance is at 400 µm or less, 500 µm or less, 1 mm or less, 2 mm or less, 3 mm or less, 5 mm or less, 7 mm or less, 10 mm or less, or in any range between the values. In certain embodiments, the inter-spacer distance is a 10 mm or less, 20 mm or less, 30 mm or less, 50 mm or less, 70 mm or less, 100 mm or less, or in any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or in any range between the values; or in certain embodiments, at most 80%, 100%, 200%, 400%, or in a range between any two of the values.

Clearly, for maintaining a given sample thickness variation between two neighboring spacers, when a more flexible plate is used, a closer inter-spacer distance is needed.

In a preferred embodiment, the spacer is a periodic square array, wherein the spacer is a pillar that has a height of 2 to 4 µm, an average lateral dimension of from 1 to 20 µm, and inter-spacer spacing of 1 µm to 100 µm.

In a preferred embodiment, the spacer is a periodic square array, wherein the spacer is a pillar that has a height of 2 to 4 µm, an average lateral dimension of from 1 to 20 µm, and inter-spacer spacing of 100 µm to 250 µm.

In a preferred embodiment, the spacer is a periodic square array, wherein the spacer is a pillar that has a height of 4 to 50 µm, an average lateral dimension of from 1 to 20 µm, and inter-spacer spacing of 1 µm to 100 µm.

In a preferred embodiment, the spacer is a periodic square array, wherein the spacer is a pillar that has a height of 4 to 50 µm, an average lateral dimension of from 1 to 20 µm, and inter-spacer spacing of 100 µm to 250 µm.

The period of spacer array is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment, 100 µm to 175 µm in a separate preferred embodiment, and 175 µm to 300 µm in a separate preferred embodiment.

Spacer density. The spacers are arranged on the respective plates at a surface density of greater than one per µm², greater than one per 10 µm², greater than one per 100 µm², greater than one per 500 µm², greater than one per 1000 µm², greater than one per 5000 µm², greater than one per 0.01 mm², greater than one per 0.1 mm², greater than one per 1 mm², greater than one per 5 mm², greater than one per 10 mm², greater than one per 100 mm², greater than one per 1000 mm², greater than one per 10000 mm², or in a range between any two of the values. In some embodiments, the spacers have a density of at least 1/mm², at least 10/mm², at least 50/mm², at least 100/mm², at least 1,000/mm², or at least 10,000/mm².

Spacer area filling factor is defined as the ratio of spacer area to the total area or the ratio of spacer period to the width. In some embodiments, the filling factor is at least 1%, 2%, 3%, 4%, 5%, 6%, 7%, 8%, 9%, 10%, 20%, or in the range between any of the two values. In certain embodiments, the filling factor is at least 2.3%.

The device that comprises two plates and spacers, wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the fourth power of the inter-spacer-distance (ISD) divided by the thickness (h) and the Young's modulus (E) of the flexible plate (ISD^4/(hE)) is 5×10^5 um3/GPa or less.

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the ratio of the inter-spacing distance of the spacers to the average width of the spacer is 2 or larger, and the filling factor of the spacers multiplied by the Young's modulus of the spacers is 2 MPa or larger.

2. Exemplary Embodiments for Rapid Homogeneous Assays (RHA)

2.1 RHA with Concentration Surface.

A device for concentrating bound label, comprises: two plates (or an enclosed channel) with a sample (that has an analyte) sandwiched between the two plates, wherein one or both of the plates has a analyte concentration area on its inner surface of the plate, wherein the analyte concentration area has a capture agent that selectively binds the bound label directly or indirectly (i.e. the analyte concentration area has a higher affinity to bind the bound label than the rest area of the plate).

Figure 2A:
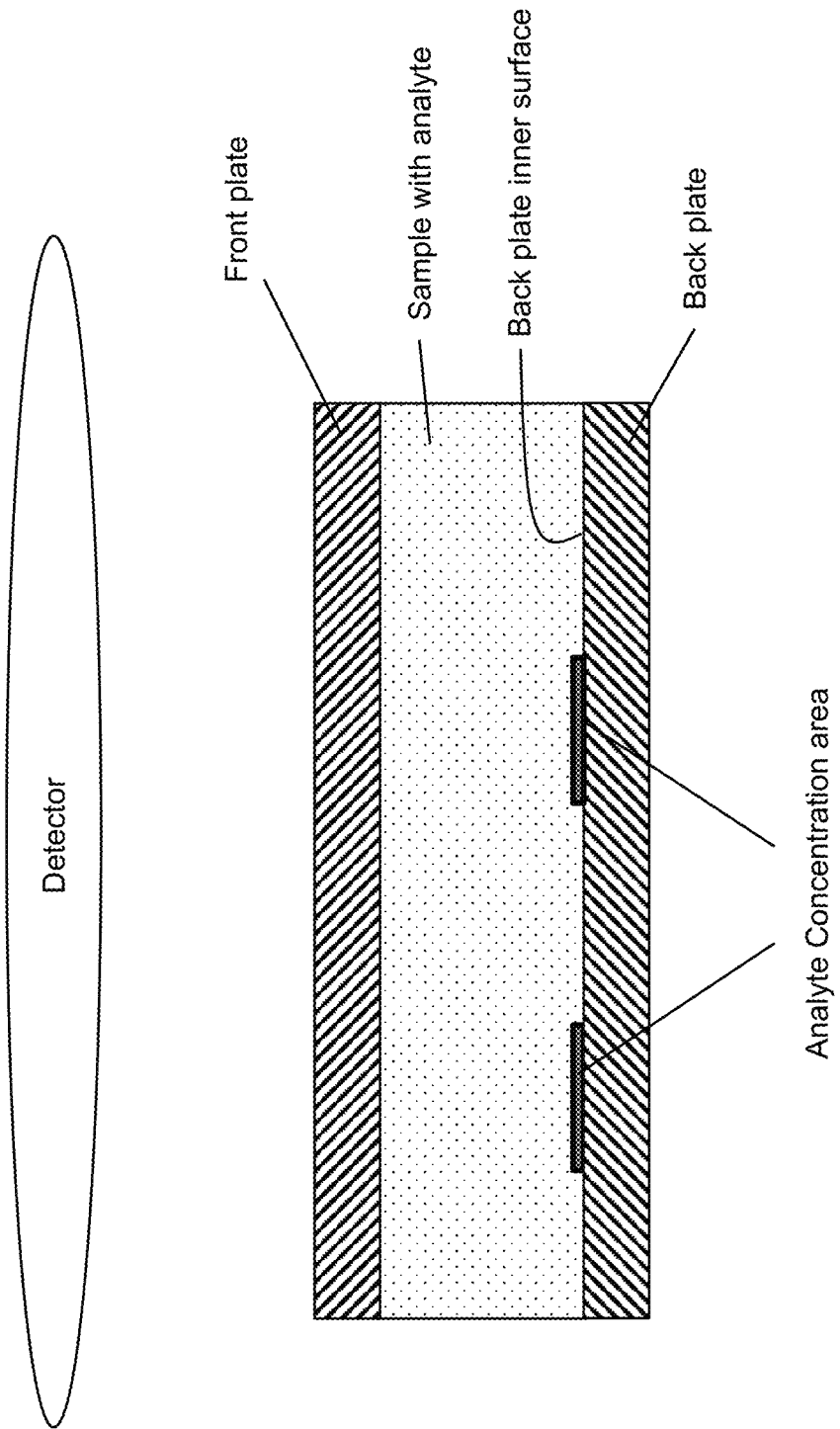
FIG. 2A schematically illustrates a cross-sectional view of an exemplary system for homogeneous assay at its closed configuration, which includes two plates with two analyte concentration areas.

FIG. 2A schematically illustrates a cross-sectional view of an exemplary system for homogeneous assay at its closed configuration, which includes two plates with two analyte concentration areas on one of the plate. As shown in the figure, a sample that contains the analyte is compressed by the two plates (front plate and back plate) into a thin layer. The back plate comprises analyte concentration areas on its inner surface. The analyte concentration areas have surfaces to capture analyte and are configured to have higher affinity to the analyte than other area of the inner surface, thereby concentrating the analyte to the surfaces thereof.

In some embodiments, the concentration of analyte to the analyte concentration areas consequentially significantly reduce the analyte in the surrounding of the analyte concentration areas, therefore each analyte concentration area not only concentrates analyte signal on its surface (higher than the surrounding area), but also reduces the local background signal in the locations that are surrounding the analyte concentration area.

Further, also shown in the figure is the detector on the top side of the two plates. The detector is configured to image the distribution of the signal of the analyte on the plate surface, wherein the signal is indicative of the presence and/or quantity of the analyte.

In some embodiments, the (i) total label concentration in a sample (since some will form bound label with analyte, and the rest will be unbound become a part of background signal), (ii) the total analyte concentration (i.e. limit of detection), or a combination of thereof is configured to achieve the visible condition.

In some embodiments, the (i) total label concentration in a sample (since some will form bound label with analyte, and the rest will be unbound become a part of background signal), (ii) the total analyte concentration (i.e. limit of detection), (iii) the area or density of the analyte concentration area, (iv) the distance between the analyte concentration area to the front plate, or (v) a combination of thereof is configured to achieve the visible condition.

In some embodiments, the amplification factor of an amplification surface is configured to achieve the visible condition.

In some embodiments, the (i) total label concentration in a sample (since some will form bound label with analyte, and the rest will be unbound become a part of background signal), (ii) the total analyte concentration (i.e. limit of detection), (iii) the area or density of the analyte concentration area, (iv) the distance between the analyte concentration area to the front plate, (v) amplification factor of an amplification surface, (vi) the shape of the concentration/amplification area, (vii) the capture reagent concentration on the concentration/amplification area, (viii) the incubation time, or (ix) a combination thereof is configured to achieve the visible condition.

In some embodiments, the analyte concentration area has a pillar shape. The shape of the top surface of the pillar can be round, a point (of a pyramid), polygon, elliptical, elongated bar, polygon, other similar shapes or combinations thereof. The spacing between the pillars in the array can be periodic or aperiodic. In some embodiments, the period (the spacing between adjacent pillars in periodic arrays) is 2 nm or less, 5 nm or less, 10 nm or less, 50 nm or less, 100 nm or less, 500 nm or less, 1000 nm or less, 2000 nm or less, 4000 nm or less, or in a range between any two of these values. In some embodiments, the average spacing between adjacent pillars in aperiodic arrays is 2 nm or less, 5 nm or less, 10 nm or less, 50 nm or less, 100 nm or less, 500 nm or less, 1000 nm or less, 2000 nm or less, 4000 nm or less, or in a range between any two of these values.

In some embodiments, the area density of the analyte concentration areas on the inner surface is 1 per $mm^2$ or less, 2 per $mm^2$ or less, 5 per $mm^2$ or less, 10 per $mm^2$ or less, 50 per $mm^2$ or less, 100 per $mm^2$ or less, 200 per $mm^2$ or less, 500 per $mm^2$ or less, 1000 per $mm^2$ or less, $1\times10^3$ per $mm^2$ or less, $2\times10^3$ per $mm^2$ or less, $3\times10^3$ per $mm^2$ or less, $5\times10^3$ per $mm^2$ or less, $10\times10^3$ per $mm^2$ or less, $2\times10^3$ per $mm^2$ or less, $3\times10^3$ per $mm^2$ or less, $5\times10^3$ per $mm^2$ or less, $10\times10^3$ per $mm^2$ or less, $1\times10^5$ per $mm^2$ or less, $5\times10^5$ per $mm^2$ or less, $1\times10^6$ per $mm^2$ or less, or in a range between any two of these values.

In some embodiments, the analyte concentration area has an average lateral dimension of 10 nm or less, 50 nm or less, 100 nm or less, 200 nm or less, 500 nm or less, or in a range between any two of these values.

In some embodiments, the average lateral dimension of the analyte concentration area is 0.5 um or less, 1 um or less, 2 um or less, 5 um or less, 10 um or less, 50 um or less, 100 um or less, 300 um or less, 500 um or less or in a range between any two of these values.

In some embodiments, the thickness of the analyte concentration area is 10 nm or less, 50 nm or less, 100 nm or less, 200 nm or less, 500 nm or less, or in a range between any two of these values.

In some embodiments, the thickness of analyte concentration area is 0.5 um or less, 1 um or less, 2 um or less, 5 um or less, 10 um or less, 50 um or less, 100 um or less, 300 um or less, 500 um or less, or in a range between any two of these values.

In some embodiments, the ratio of the spacing between two plates at the closed configuration versus the height (thickness) of the analyte concentration area is 1 or less, 1.1 or less, 1.2 or less, 1.5 or less, 2 or less, 3 or less, 5 or less, 10 or less, 15 or less, 20 or less, 30 or less, 40 or less, 50 or less, 60 or less, 80 or less, 100 or less, 200 or less, 300 or less, 400 or less, 500 or less, 600 or less, 800 or less, 1000 or less, or in a range between any two of these values.

In some embodiments, the height (thickness) of the analyte concentration area is 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, 300 um or more, 500 um or more, or in a range between any two of these values.

2.2 RHA with Concentration Protrusion (e.g. Pillar)

A device for concentrating bound label, comprises: two plates (or an enclosed channel) with a sample (that has an analyte) sandwiched between the two plates, wherein one or both of the plates has a protrusion, wherein the protrusion has an analyte concentration area on at least one of the protrusion's surfaces, wherein the analyte concentration area has a capture agent that selectively binds to the labeled analyte/bound label and/or the analyte to be labeled.

Figure 2B:
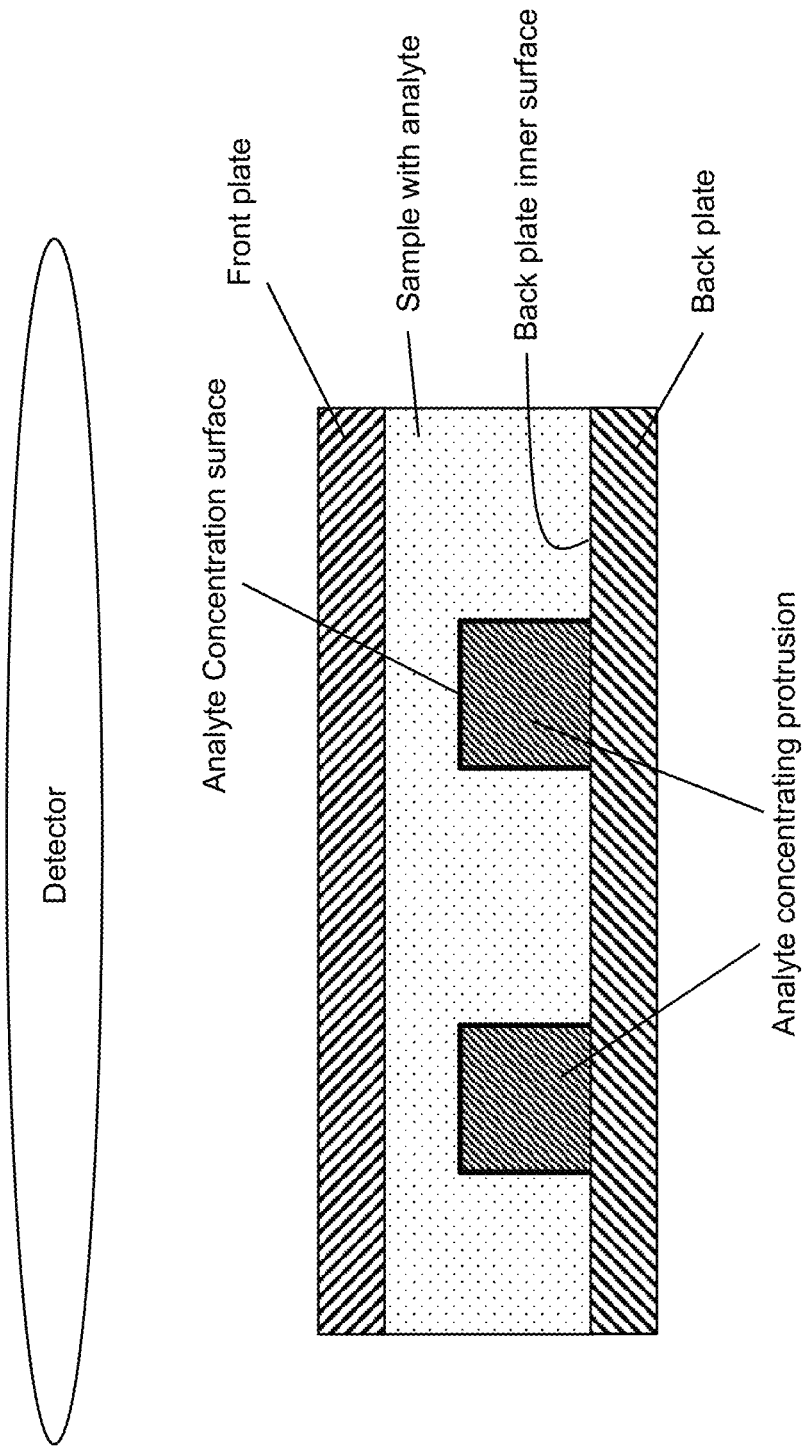
FIG. 2B schematically illustrates a cross-sectional view of another exemplary system for homogeneous assay at its closed configuration, which includes two plates with two analyte concentrating protrusions.

FIG. 2B schematically illustrates a cross-sectional view of another exemplary system for homogeneous assay at its closed configuration, which includes two plates with two analyte concentrating protrusions. Similar as FIG. 2A, the sample is compressed by the two plates (front plate and back plate) into a thin layer. The back plate comprises the two analyte concentrating protrusions that extending from its inner surface. Each of the concentrating protrusions has a concentration surface to capture the analyte. In addition to the analyte signal enhancing effect and background reduction effect, each protrusion further reduces the local background signal on top of it, by reducing the sample thickness on top of it. Similar to FIG. 2A, the system also includes the detector that detects the signal of the analyte.

Figure 7:
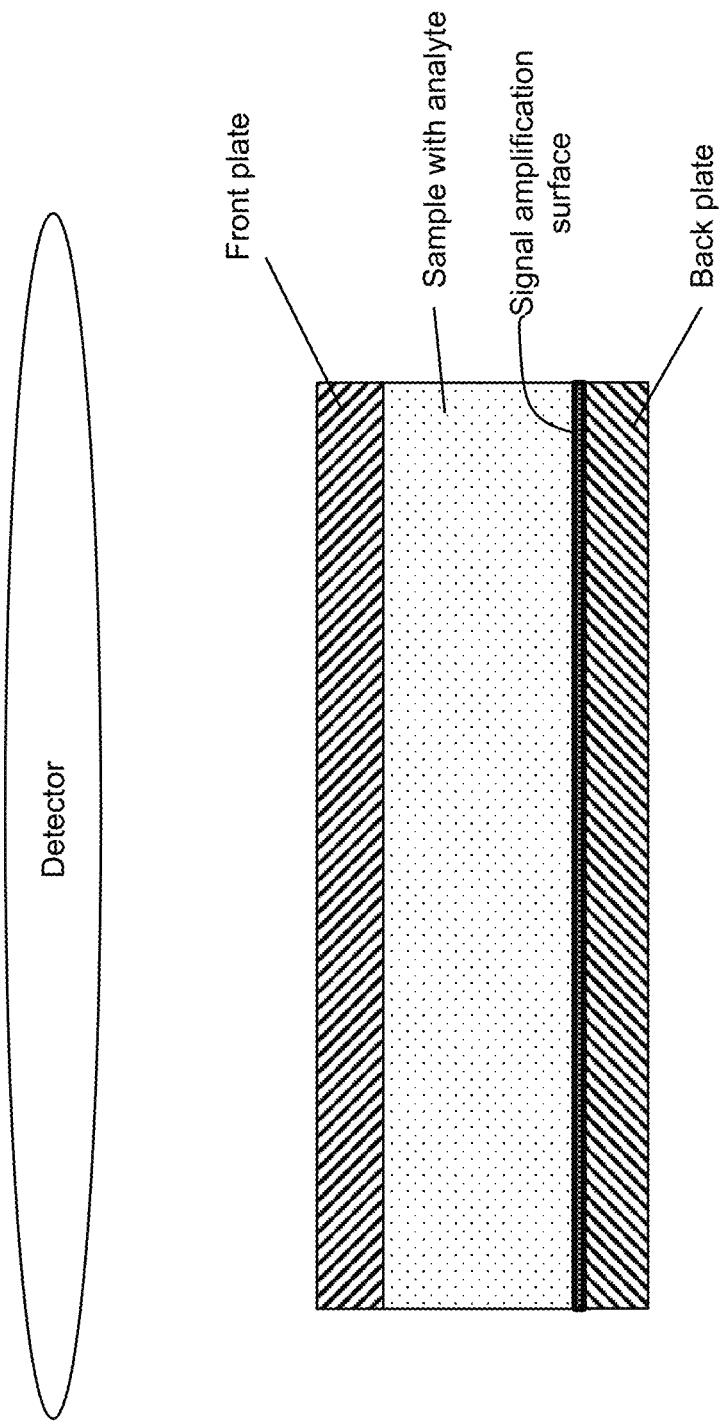
FIG. 7 schematically illustrates a cross-sectional view of another exemplary system for homogeneous assay at its closed configuration, which includes a signal amplification surface on one of the two plates.

FIG. 7 schematically illustrates a cross-sectional view of another exemplary system for homogeneous assay at its closed configuration, which includes a signal amplification surface on one of the two plates. As shown in the figure, the back plate comprises a signal amplification surface on its inner surface. When the labeled analyte is bound to the signal amplification surface, the signal amplification surface is configured to amplify the signal of the bound analyte to a level that is distinguishable from the background.

The spacing between the pillars (analytes concentration area) in the array can be periodic or aperiodic. In many embodiments, a periodic array is preferred. In some embodiments, the period (the spacing between adjacent pillars in periodic arrays) is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, 25 um or less, 30 um or less, 40 um or less, 50 um or less, 60 um or less, 70 um or less, or in a range between any two of these values.

In some embodiments, the average spacing between adjacent pillars in aperiodic arrays is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, 25 um or less, 30 um or less, 40 um or less, 50 um or less, 60 um or less, 70 um or less, or in a range between any two of these values.

In certain preferred embodiments, the average lateral dimension of the protrusion is 0.5 um, 1 um, 3 um, 5 um, 10 um, 20 um, 50 um, 100 um, 150 um, 200 um, or in a range between any two of these values.

In certain preferred embodiments, the average height of the protrusion is 0.5 um, 1 um, 3 um, 5 um, 10 um, 20 um, 50 um, 100 um, 150 um, 200 um, or in a range between any two of these values.

In certain preferred embodiments, the average spacing between adjacent pillars is 1 um, 2 um, 5 um, 10 um, 20 um, 50 um, 100 um, 150 um, 200 um, 500 um, or in a range between any two of these values.

In certain preferred embodiments, the average lateral dimension of the protrusion is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, 2 times of the DP, 3 times of the DP or in a range between any two of these values.

In certain preferred embodiments, the average height of the protrusion is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, 2 times of the DP, 3 times of the DP or in a range between any two of these values. In certain preferred embodiments, the average spacing between adjacent pillars is 0.01 times of the DP, 0.1 times of the DP, 0.3 times of the DP, 0.5 times of the DP, 0.7 times of the DP, 1 times of the DP, 1.2 times of the DP, 1.5 times of the DP, 2 times of the DP, 5 times of the DP or in a range between any two of these values.

Spacing between the top surface of the protrusion and the plate above (i.e. protrusion-surface to plate surface distance (PsPsD)). In certain embodiments, the PsPsD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, or in a range between any two of these values.

In certain preferred embodiments, the PsPsD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, or in a range between any two of these values.

In some preferred embodiments, the PsPsD is 2 nm or less, 5 nm or less, 10 nm or less, 50 nm or less, 100 nm or less, 500 nm or less, 1 um or less, 2 um or less, 3 um or less, 4 um or less, 5 um or less, or in a range between any two of these values.

Difference between protrusion height and spacer height (i.e. Protrusion and Spacer Height Difference (PSHD)). In certain embodiments, the PSHD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, or in a range between any two of these values.

In certain preferred embodiments, the PSHD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, or in a range between any two of these values.

In some preferred embodiments, the PSHD is 2 nm or less, 5 nm or less, 10 nm or less, 50 nm or less, 100 nm or less, 500 nm or less, 1 um or less, 2 um or less, 3 um or less, 4 um or less, 5 um or less, or in a range between any two of these values.

Protrusion also served as spacers. In certain embodiments, the protrusion for analyte concentration also served as the spacer that regulate the spacing between the two plates. The protrusion then can have the similar characteristics of the spacer specified herein, such as the flat top, significantly uniform height. In these cases, the analyte concentration area on the sidewall of the protrusion (which also serves as the spacer) can catch the analytes.

In some embodiments, the area density of the concentrating protrusions on the inner surface is 1 per $mm^2$ or less, 2 per $mm^2$ or less, 5 per $mm^2$ or less, 10 per $mm^2$ or less, 50 per $mm^2$ or less, 100 per $mm^2$ or less, 200 per $mm^2$ or less, 500 per $mm^2$ or less, 1000 per $mm^2$ or less, $1\times10^3$ per $mm^2$ or less, $2\times10^3$ per $mm^2$ or less, $3\times10^3$ per $mm^2$ or less, $5\times10^3$ per $mm^2$ or less, $10\times10^3$ per $mm^2$ or less, $2\times10^3$ per $mm^2$ or less, $3\times10^3$ per $mm^2$ or less, $5\times10^3$ per $mm^2$ or less, $10\times10^3$ per $mm^2$ or less, $1\times10^5$ per $mm^2$ or less, $5\times10^5$ per $mm^2$ or less, $1\times10^6$ per $mm^2$ or less, or in a range between any two of these values.

In some embodiments, the protrusion (nano or micro islands) has an average lateral dimension of 10 nm or less, 50 nm or less, 100 nm or less, 200 nm or less, 500 nm or less, or in a range between any two of these values.

In some embodiments, the average lateral dimension of the protrusion (nano or micro islands) is 0.5 um or less, 1 um or less, 2 um or less, 5 um or less, 10 um or less, 50 um or less, 100 um or less, 300 um or less, 500 um or less or in a range between any two of these values.

In some embodiments, the height of the protrusion (nano or micro islands) is 10 nm or less, 50 nm or less, 100 nm or less, 200 nm or less, 500 nm or less, or in a range between any two of these values.

In some embodiments, the height of protrusion (nano or micro islands) is 0.5 um or less, 1 um or less, 2 um or less, 5 um or less, 10 um or less, 50 um or less, 100 um or less, 300 um or less, 500 um or less, or in a range between any two of these values.

In some embodiments, the ratio of the spacing between two plates at the closed configuration versus the height of the concentrating protrusion is 1 or less, 1.1 or less, 1.2 or less, 1.5 or less, 2 or less, 3 or less, 10 or less, 15 or less, 20 or less, 30 or less, 40 or less, 50 or less, 60 or less, 80 or less, 100 or less, 200 or less, 300 or less, 400 or less, 500 or less, 600 or less, 800 or less, 1000 or less, or in a range between any two of these values.

In some embodiments, the height of the concentrating protrusion is 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, 300 um or more, 500 um or more, or in a range between any two of these values.

ADDITIONAL EMBODIMENTS

Figure 3:
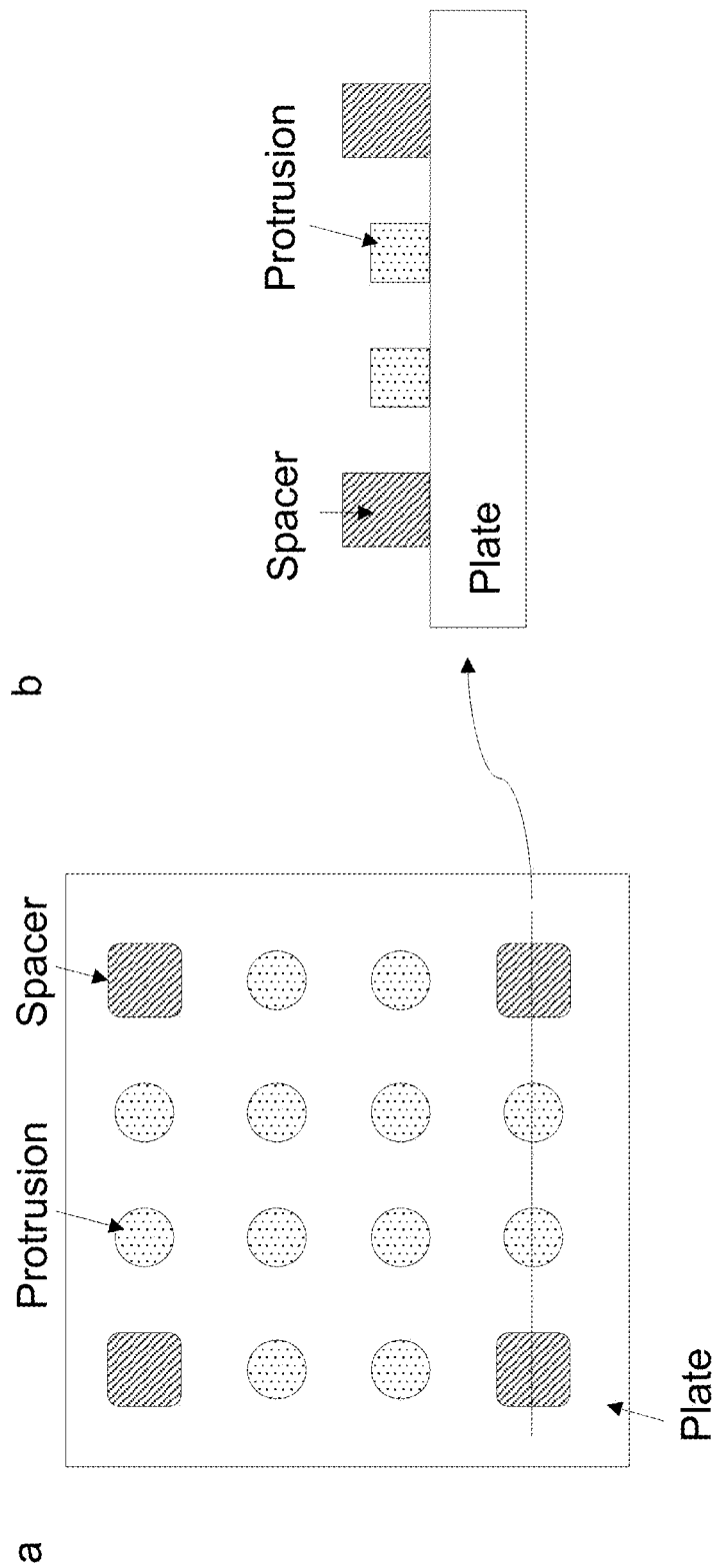
FIG. 3 shows schematic drawings for exemplary embodiments of the device for homogeneous assay with "protrusion" pillars and "spacer" pillars on the plate. (a) Top view and (b) cross sectional view.

FIG. 3 shows schematic drawings for exemplary embodiments of the device for homogeneous assay with "protrusion" pillars and "spacer" pillars on the plate. (a) Top view and (b) cross sectional view. As shown in the figure, protrusion pillars have a smaller height than the spacers in the device. In some embodiments, the protrusions and the spacers have similar shapes, while in other embodiments, their shapes are different.

In some embodiments, only the top surface of the protrusions has the concentrating area. In some embodiments, only the side surface(s) of the protrusions has/have the concentrating area. In some embodiments, there are 1, 2, 3, 4, 5, 6, 7 or more side surfaces of the protrusions have the concentrating area. In some embodiments, both the top surface and a number of the protrusions have the concentrating area. In some embodiments, all the surfaces of the protrusions have the concentrating area. The exact number and location of the surfaces having the concentrating area (i.e. coated with capture agent) determines the concentrating efficiency, therefore is subject to empirical test and adjustment.

In some embodiments, the protrusion on the plate have analyte concentration area (ACA) on one or several of its surfaces. In some embodiments, the analyte concentration area (ACA) on the protrusion is created by the surface coating.

Figure 4:
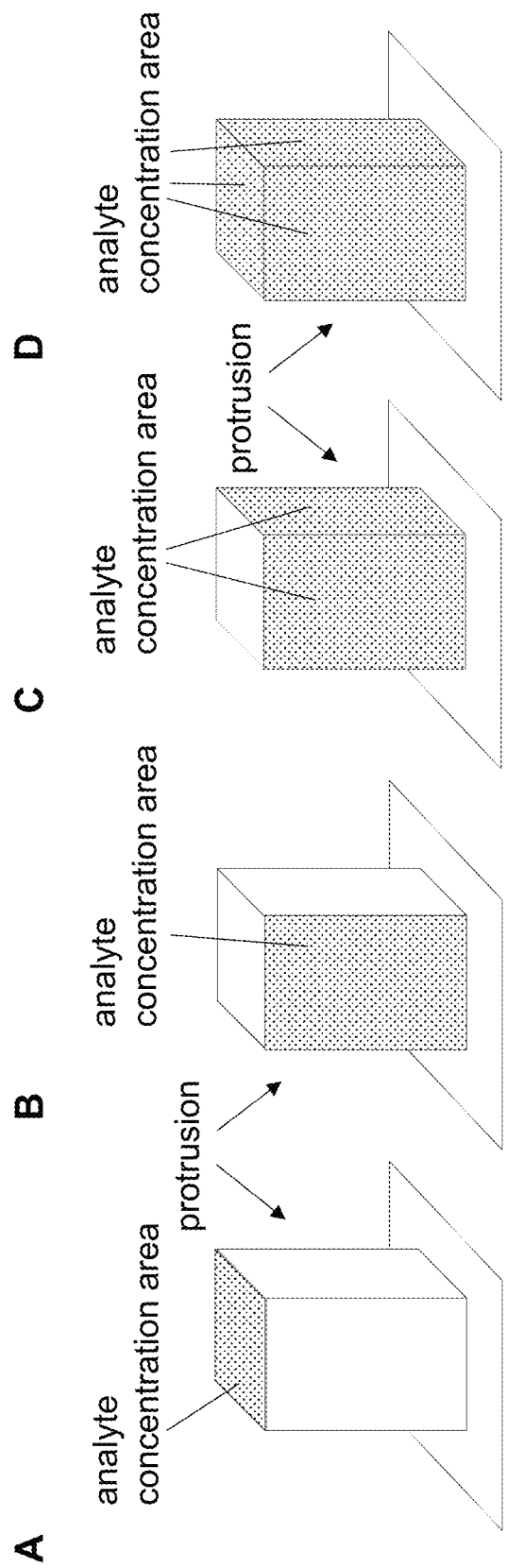
FIG. 4 shows schematic drawings for exemplary embodiments of analyte concentration area (ACA) created by surface coating on the protrusions: (a) coating on the top surface of the protrusion; (b) coating on one side or several side surfaces of the protrusion; (c) coating on all the side surfaces of the protrusion; and (d) coating on all the surfaces of the protrusion, to create the analyte concentration area (ACA).

FIG. 4 shows schematic drawings for exemplary embodiments of analyte concentration area (ACA) created by surface coating on the protrusions: (a) coating on the top surface of the protrusion; (b) coating on one side or several side surfaces of the protrusion; (c) coating on all the side surfaces of the protrusion; and (d) coating on all the surfaces of the protrusion.

The methods of selectively coating a surface or several surfaces of the protrusion include, but not limited to,
(a) touching the one or several surfaces of the protrusion with a reagent on a surface of a coating device, wherein the reagent comprises the capture agent that is configured to selectively bind to the labeled analyte/bound label and/or the analyte to be labeled;
(b) evaporating the one or several surfaces of the protrusion with a binding layer, wherein the binding layer binds the capture agent when immersing the device in the reagent;
(c) evaporating the one or several surfaces of the protrusion and/or back plane with a binding-prohibition layer, wherein the surfaces with the binding-prohibition layer are prevented by the from binding the capture agent, while the surfaces without the binding-prohibition layer are capable of binding the capture agent; and
(d) combination of above methods.

Figure 5:
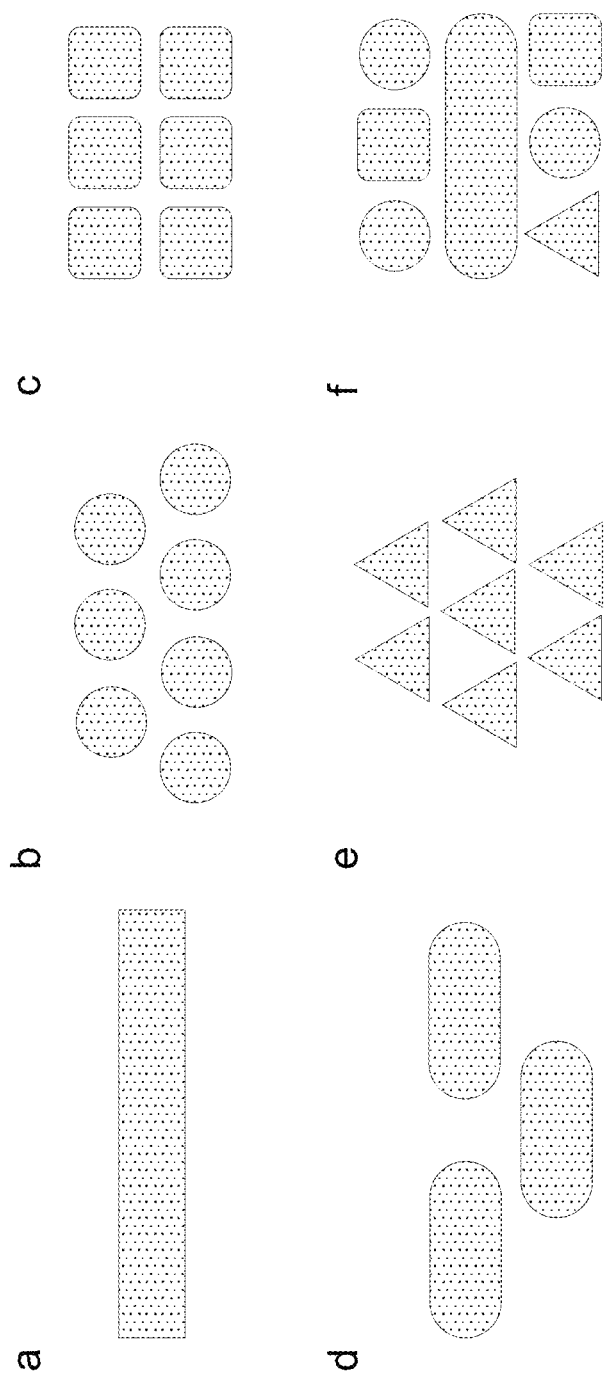
FIG. 5 shows schematic drawings for exemplary embodiments of the shapes of the protrusions from the top view: (a) line shape protrusion; (b) circle dots shape protrusion; (c) square dots shape protrusion; (d) bar shape protrusion; (e) triangular shape protrusion; and (f) combination of the above.

In some embodiments, the protrusion (nano or micro islands) have a pillar shape. The shape of the top surface of the pillar can be round, a point (of a pyramid), polygon, elliptical, elongated bar, polygon, other similar shapes or combinations thereof. FIG. 5 shows schematic drawings for exemplary embodiments of the shapes of the protrusions from the top view: (a) line shape protrusion; (b) circle dots shape protrusion; (c) square dots shape protrusion; (d) bar shape protrusion; (e) triangular shape protrusion; and (f) combination of the above.

Figure 6:
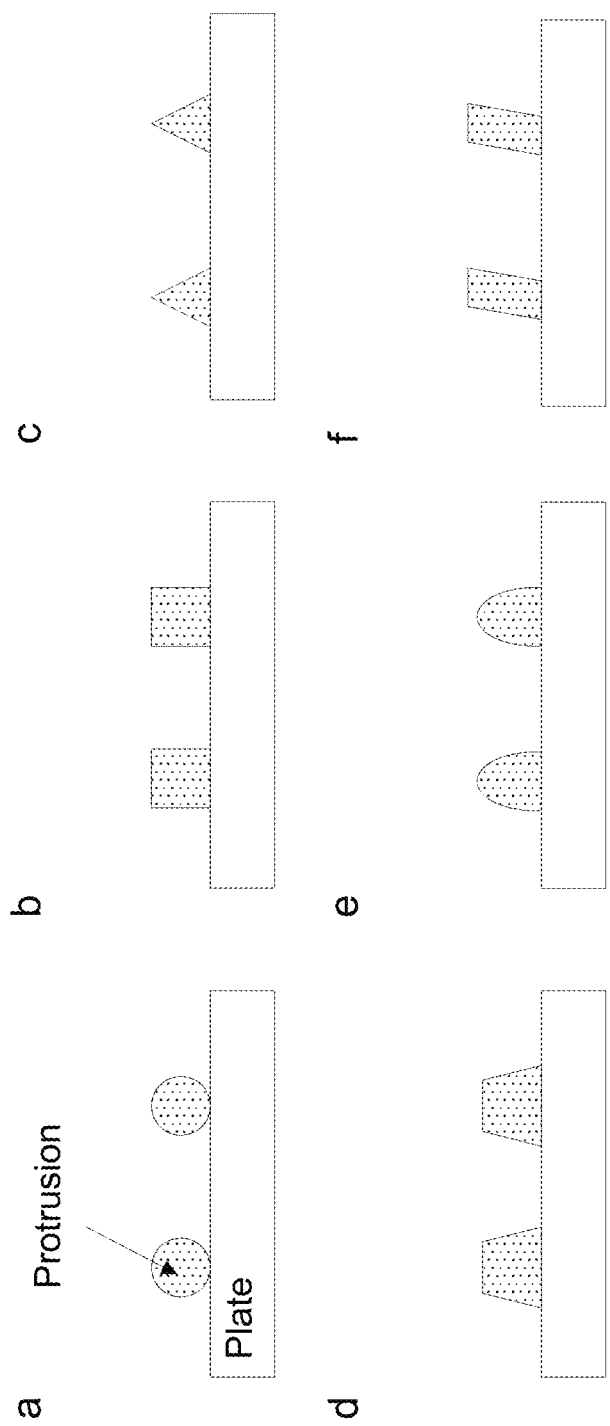
FIG. 6 shows schematic drawings for exemplary embodiments of the shapes of protrusions from the side view: (a) circle shape protrusion; (b) square shape protrusion; (c) pyramid shape protrusion; (d) trapezoid shape protrusion; (e) ellipse shape protrusion; and (f) parallelogram shape protrusion.

In some embodiments, the shape of the side surface of the protrusion can be round, a point (of a pyramid), polygon, elliptical, elongated bar, polygon, other similar shapes or combinations thereof. FIG. 6 shows schematic drawings for exemplary embodiments of the shapes of protrusions from the side view: (a) circle shape protrusion; (b) square shape protrusion; (c) pyramid shape protrusion; (d) trapezoid shape protrusion; (e) ellipse shape protrusion; and (f) parallelogram shape protrusion.

2.3 RHA with Concentration Beads

A device for concentrating labeled analyte/bound label, comprises: two plates (or an enclosed channel) with a sample (that has an analyte) sandwiched between the two plates, wherein one bead or a plurality of beads is placed in the sample, wherein the bead has an analyte concentration area on the bead's surface, wherein the analyte concentration area has a capture agent selectively binds the labeled analyte/bound label and/or the analyte to be labeled.

In some embodiments, the beads, the ratio of the spacing between the two plate and the diameter of the beads is 1, 1.1, 1.2, 1.3, 1.5, 2, 5, 10, 20, 30, 50, 100, or in a range between any two of these values.

One aspect of the present invention provides a device for homogeneous assay with concentration beads. In some embodiments, the device comprises: a first plate, a second plate, and spacers. In some embodiments, the plates are movable relative to each other into different configurations, including an open configuration and a closed configuration. In some embodiments, each of the plates has, on its respective inner surface, a sample contact area for contacting a sample suspected of comprising an analyte. In some embodiments, one or both of the plates comprise the spacers, at least one of the spacers is inside the sample contact area, and the spacers have a predetermined substantially uniform height. In some embodiments, one or both of the plates comprise, on the respective inner surface, a plurality of beads that have capture agent immobilized thereon, wherein the capture agent is capable of binding to and immobilizing the analyte. In some embodiments, one or both of the plates comprise, on the respective inner surface, detection agent that is configured to, upon contacting the sample, be dissolved in the sample and bind to the analyte.

In some embodiments, in the open configuration, the two plates are partially or entirely separated apart, the spacing between the plates is not regulated by the spacers, and the sample is deposited on one or both of the plates.

In some embodiments, in the closed configuration, which is configured after deposition of the sample in the open configuration: at least part of the sample is compressed by the two plates into a layer of highly uniform thickness, and the uniform thickness of the layer is confined by the inner surfaces of the plates and is regulated by the plates and the spacers.

In some embodiments, the capture agent and the detection agent are configured to bind to the analyte at different locations thereof and to form a capture agent-analyte-detection agent sandwich that is immobilized to the bead.

In some embodiments, the analyte in the layer of uniform thickness is concentrated by the beads so that signal of the captured analyte on the beads is distinguishable from signal emanating from other area in the layer of uniform thickness.

In some embodiments, the beads have a spherical shape. In some embodiments, the beads have a shape of tube, sphere, cylinder, cube, ellipsoid, cone, tetrahedron, dodecahedron, octahedron, triangular prism, torus, pyramid, or any other shapes, or any combination thereof.

In some embodiments, the bead size, capture agent density on the beads, the detection agent concentration are the factors that are among the important factors that affect the distinguishability of the signal of the bound detection agent from the free detection agent.

In some embodiments, the beads are made of a material selected from the group consisting of: polystyrene, polypropylene, polycarbonate, PMMA, PC, COC, COP, glass, resin, aluminum, gold or other metal or any other material whose surface can be modified to be associated with the capture agent.

In some embodiments, the beads are the spacers that regulate the thickness of the layer at the closed configuration.

In some embodiments, the beads and the detection agent are on the same plate. In some embodiments, the beads and the detection agent are on different plates.

In some embodiments, the beads are micro- or nanoparticles. In some embodiments, the beads have an average diameter of 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, or in a range between any two of these values. In some preferred embodiments, the beads have an average diameter of 0.1 um or more, 0.2 um or more, 0.5 um or more, 1 um or more, 2 um or more, 3 um or more, 5 um or more, 10 um or more, or in a range between any two of these values.

In some embodiments, the beads have an area density of 1 per $mm^2$ or more, 2 per $mm^2$ or more, 5 per $mm^2$ or more, 10 per $mm^2$ or more, 50 per $mm^2$ or more, 100 per $mm^2$ or more, 200 per $mm^2$ or more, 500 per $mm^2$ or more, 1000 per $mm^2$ or more, $2\times10^3$ per $mm^2$ or more, $3\times10^3$ per $mm^2$ or more, $5\times10^3$ per $mm^2$ or more, $10\times10^3$ per $mm^2$ or more, $1\times10^5$ per $mm^2$ or more, $5\times10^5$ per $mm^2$ or more, $1\times10^6$ per $mm^2$ or more, or in a range between any two of these values.

In some embodiments, the beads are aligned on the plate inner surface in periodic or aperiodic arrays. In some embodiments, the period (the spacing between adjacent beads in periodic arrays) is 2 nm or less, 5 nm or less, 10 nm or less, 50 nm or less, 100 nm or less, 500 nm or less, 1000 nm or less, 2000 nm or less, 4000 nm or less, or in a range between any two of these values. In some embodiments, the average spacing between adjacent beads in aperiodic arrays is 2 nm or less, 5 nm or less, 10 nm or less, 50 nm or less, 100 nm or less, 500 nm or less, 1000 nm or less, 2000 nm or less, 4000 nm or less, or in a range between any two of these values.

In some embodiments, the beads are configured to have a concentration in the layer of uniform thickness of $1\times10^3$/uL or more, $5\times10^3$/uL or more, $1\times10^4$/uL or more, $5\times10^4$/uL or more, $1\times10^5$/uL or more, $5\times10^5$/uL or more, $1\times10^6$/uL or more, $5\times10^6$/uL or more, $1\times10^7$/uL or more, $5\times10^7$/uL or more, $1\times10^8$/uL or more, $5\times10^8$/uL or more, $1\times10^9$/uL or more, or in a range between any two of these values.

In some embodiments, it is preferable to have the beads forming one single layer in the layer of uniform thickness. In some embodiments, the product of beads concentration, top area size of one bead and spacing size between plates is 1 or less, 0.9 or less, 0.8 or less, 0.7 or less, 0.6 or less, 0.5 or less, 0.4 or less, 0.3 or less, 0.2 or less, 0.1 or less, 0.08 or less, 0.06 or less, 0.04 or less, 0.01 or less, 0.008 or less, 0.006 or less, 0.004 or less, 0.002 or less, 0.001 or less, or in a range between any two of these values.

In some embodiments, the ratio of the spacing between two plates at the closed configuration versus the height (thickness) of the beads is 1 or less, 1.1 or less, 1.2 or less, 1.5 or less, 2 or less, 3 or less, 5 or less, 10 or less, 15 or less, 20 or less, 30 or less, 40 or less, 50 or less, 60 or less, 80 or less, 100 or less, 200 or less, 300 or less, 400 or less, 500 or less, 600 or less, 800 or less, 1000 or less, or in a range between any two of these values.

In some embodiments, the height (thickness) of the beads is 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, 300 um or more, 500 um or more, or in a range between any two of these values.

In some embodiments, the beads have signal amplification properties. In some embodiments, the beads are configured to amplify a signal of the analyte and/or the detection agent in proximity of the beads. In some embodiments, the beads amplify the signal that is at a distance of 0-1 um from the bead surface. In some embodiments, the distance is very small (e.g. 20 nm, 50 nm, or 100 nm). In some embodiments, the beads have a signal amplification factor of 1 or more, 2 or more, 5 or more, 10 or more, 20 or more, 30 or more, 50 or more, 100 or more, 200 or more, 500 or more, 1000 or more, 5000 or more, 10000 or more, or in a range between any two of these values.

Another aspect of the present invention provides a method of homogeneous assay. In some embodiments, the method comprises the steps of:
  (a) obtaining a sample suspected of containing an analyte;
  (b) obtaining a first and second plates that are movable relative to each other into different configurations, including an open configuration and a closed configuration, wherein:
    i. each of the plates has, on its respective inner surface, a sample contact area for contacting the sample,
    ii. one or both of the plates comprise the spacers, and at least one of the spacers is inside the sample contact area;
    iii. one or both of the plates comprise, on the respective inner surface, a plurality of beads that have capture agent immobilized thereon, wherein the capture agent is capable of binding to and immobilizing the analyte; and
    iv. one or both of the plates comprise, on the respective inner surface, detection agent that is configured to, upon contacting the sample, be dissolved in the sample and bind to the analyte;
      wherein the spacers have a predetermined substantially uniform height;
  (c) depositing the sample on one or both of the plates when the plates are in an open configuration, wherein in the open configuration the two plates are partially or entirely separated apart and the spacing between the plates is not regulated by the spacers;
  (d) after (c), bringing the two plates together and pressing the plates into a closed configuration, wherein in the closed configuration: at least part of the sample is compressed by the two plates into a layer of highly uniform thickness, the uniform thickness of the layer is confined by the inner surfaces of the two plates and is regulated by the spacers and the plates; and (e) while the plates are at the closed configuration, detecting the analyte in the layer of uniform thickness, wherein the capture agent and the detection agent are configured to bind to the analyte at different locations thereof and to form a capture agent-analyte-detection agent sandwich that is immobilized to the bead; and wherein the beads, the capture agent, and the detection agent are configured to render signal from the bead-associated capture agent-analyte-detection agent sandwich distinguishable from signal of free detection agent in the layer of uniform thickness.

In some embodiments, the sample contact sites are not washed before the imaging step (e).

In some embodiments, the method further comprises washing the sample contact area before the imaging step (e).

In some embodiments, the method further comprises determining the presence of the analyte and/or measuring the amount of the analyte.

In some embodiments, the first plate and the second plate are obtained for a homogeneous assay. Before starting the assay, the two plates are pre-treated as follows: capture antibody is first immobilized on the beads, and then these beads are coated on the first plate; while labeled detection antibody is coated on the second plate. For the assay, when the two plates are separated apart (in the open configuration), a sample suspected of containing the analyte is deposited on one of the plates (the first or second plate) or both plates (not shown). After the sample deposition, the two plates are then brought together and pressed against each other to enter the closed configuration. As discussed above, the detection antibody, upon contacting the sample, is dissolved in the sample. And in the closed configuration, at least part of the sample is compressed into a layer of uniform thickness. In such a layer of uniform thickness, the capture antibody on the beads and the diffusing detection antibody both bind to the analyte, but at different locations thereof, thereby forming a capture antibody-analyte-detection antibody sandwich. As the detection antibody is labeled with fluorophore (red asterisks), the attraction of the analyte and labeled antibody around the surface of the beads due to antibody-antigen interactions renders the local concentration of fluorescent signal surrounding the beads significantly higher than the ambient background. Imaging is performed 30 seconds after closing the two plates without washing.

Another aspect of the present invention provides a method of analyzing the image for a rapid homogeneous assay. In some embodiments, the method comprises the steps of:

(a) obtaining an image of the signal in the device of embodiment AB1 at the closed configuration, wherein the image is selected from the group consisting of bright field image, dark field image, fluorescence image, and phosphorescence image;

(b) analyzing the image, identifying beads in the image, and extracting information of beads size, signal intensity of beads, distance between beads, distribution of beads, and number of beads;

(c) deducing analyte concentration by analyzing the extracted information from step (b) and calculating parameters of the beads.

In some embodiments, calculated parameter is the average signal intensity from all the tested bead in the device;

In some embodiments, calculated parameter is the highest signal intensity from all the tested bead in the device;

In some embodiments, calculated parameter is the signal intensity distribution from all the tested bead in the device;

In some embodiments, calculated parameter is the counting number of all the tested bead in the device with signal intensity larger than a threshold;

In some embodiments, calculated parameter is the average signal intensity from all the tested bead in a certain area on the device;

In some embodiments, calculated parameter is the highest signal intensity from all the tested bead in a certain area on the device;

In some embodiments, calculated parameter is the signal intensity distribution from all the tested bead in a certain area on the device;

In some embodiments, calculated parameter is the counting number of all the tested bead in a certain area on the device with signal intensity larger than a threshold.

Plate with Significantly Periodically Arranged Beads and Method of Making the Same In certain embodiments, periodically arrangement of the concentrating beads on the plate is advantageous in that: 1) periodicity reduces the chance of bead aggregation; 2) carefully designed inter-bead spacing ensures maximal concentration efficiency when the concentrating space (the space surrounding the bead in which all analytes can be absorbed by the individual bead within a certain period of time, e.g. assay incubation time) of each bead does not significantly overlap with one another, therefore making the maximal use of each individual bead.

Figure 10:
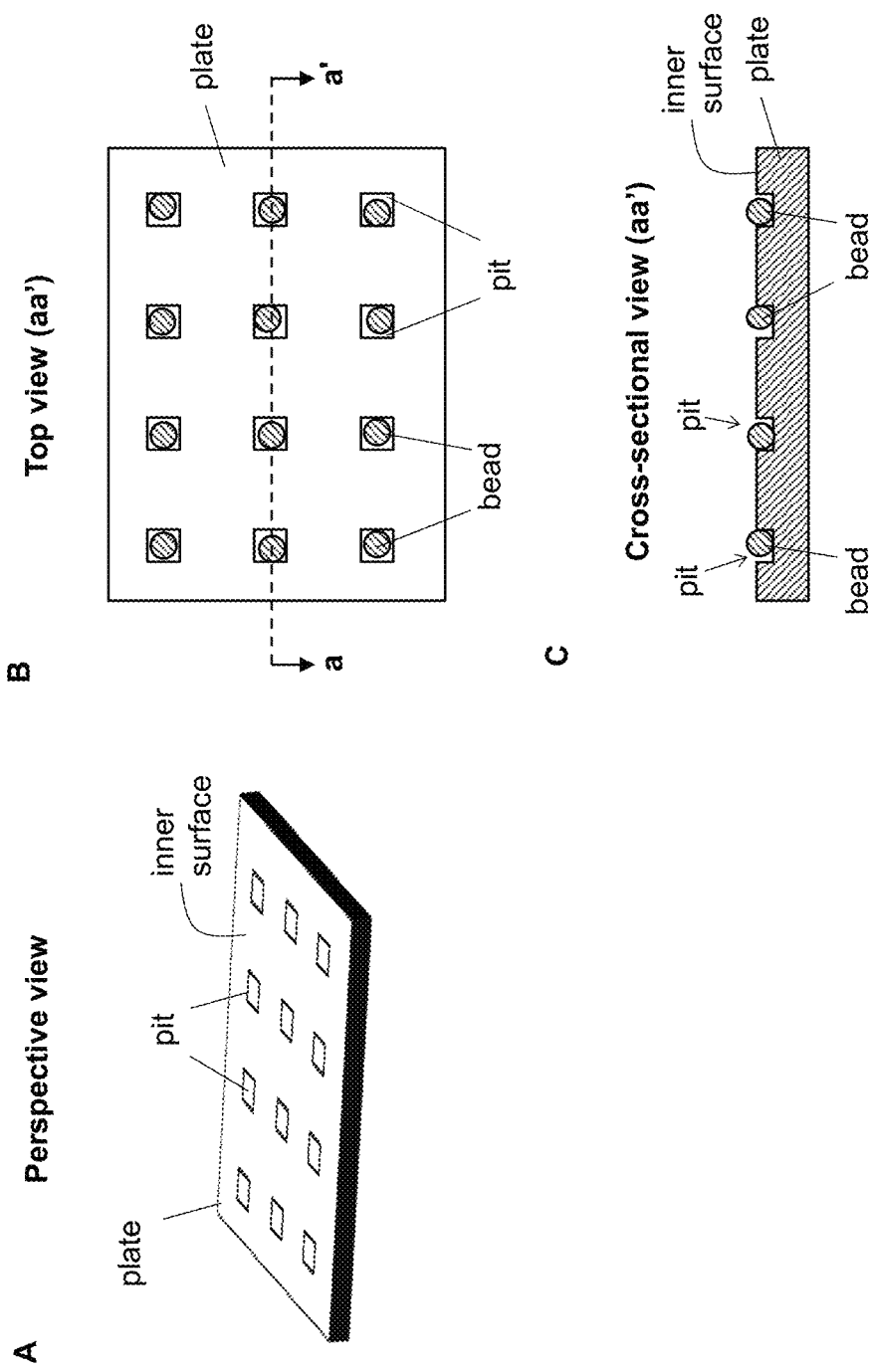
FIG. 10 provides schematic illustrations of one embodiment of the device which have periodically arranged beads on one plate.

FIG. 10 provides schematic illustrations of one embodiment of the device which have periodically arranged beads on one plate. As shown in the figure, the plate comprises a plurality of pits periodically arranged on the inner surface. The plurality of pits have a depth and a lateral shape that are configured to contain one bead per each pit, thereby making the beads periodically arranged on the inner surface of the plate as well.

In some embodiments, the shape of the pits is round, a point (of a pyramid), polygon, elliptical, elongated bar, polygon, other similar shapes or combinations thereof.

In some embodiments, the pits' diameter is 10 nm, 50 nm, 100 nm, 500 nm, 1 um, 2 um, 3 um, 5 um, 10 um, 20 um, 30 um, 50 um, 100 um, 200 um, 500 um or in a range between any of the two values.

In some embodiments, the preferred pits' diameter is 1 um, 2 um, 3 um, 5 um, 10 um, 20 um, 30 um, 50 um, 100 um or in a range between any of the two values.

In some embodiments, the pits' depth is 10 nm, 50 nm, 100 nm, 500 nm, 1 um, 2 um, 3 um, 5 um, 10 um, 20 um, 30 um, 50 um, 100 um, 200 um, 500 um or in a range between any of the two values.

In some embodiments, the preferred pits' depth is 500 nm, 1 um, 2 um, 3 um, 5 um, 10 um, 20 um, 30 um, 50 um or in a range between any of the two values.

In some embodiments, the inter-pit spacing is 10 nm, 50 nm, 100 nm, 500 nm, 1 um, 2 um, 3 um, 5 um, 10 um, 20 um, 30 um, 50 um, 100 um, 200 um, 500 um or in a range between any of the two values.

In some embodiments, the preferred inter-pit spacing is 1 um, 5 um, 10 um, 20 um, 30 um, 50 um, 100 um, 150 um, 200 um or in a range between any of the two values.

In some embodiments, it is preferred that the pits are hydrophilic. In some embodiments, the liquid contact angle (wetting property) of the pits plate is 5 degrees, 10 degrees, 20 degrees, 30 degrees, 60 degrees, 80 degrees, or in a range between any of the two values. In some embodiments, the liquid contact angles of the pits and other area on the plate are different, where the difference is 0 degrees, 20 degrees, 30 degrees, 60 degrees, 80 degrees, or in a range between any of the two values.

Another aspect of the present invention is to provide a method of making a plate with beads significantly periodically arranged thereon. The method provides a self-assembly process for the beads to be distributed into each individual pit on the plate.

Figure 11:
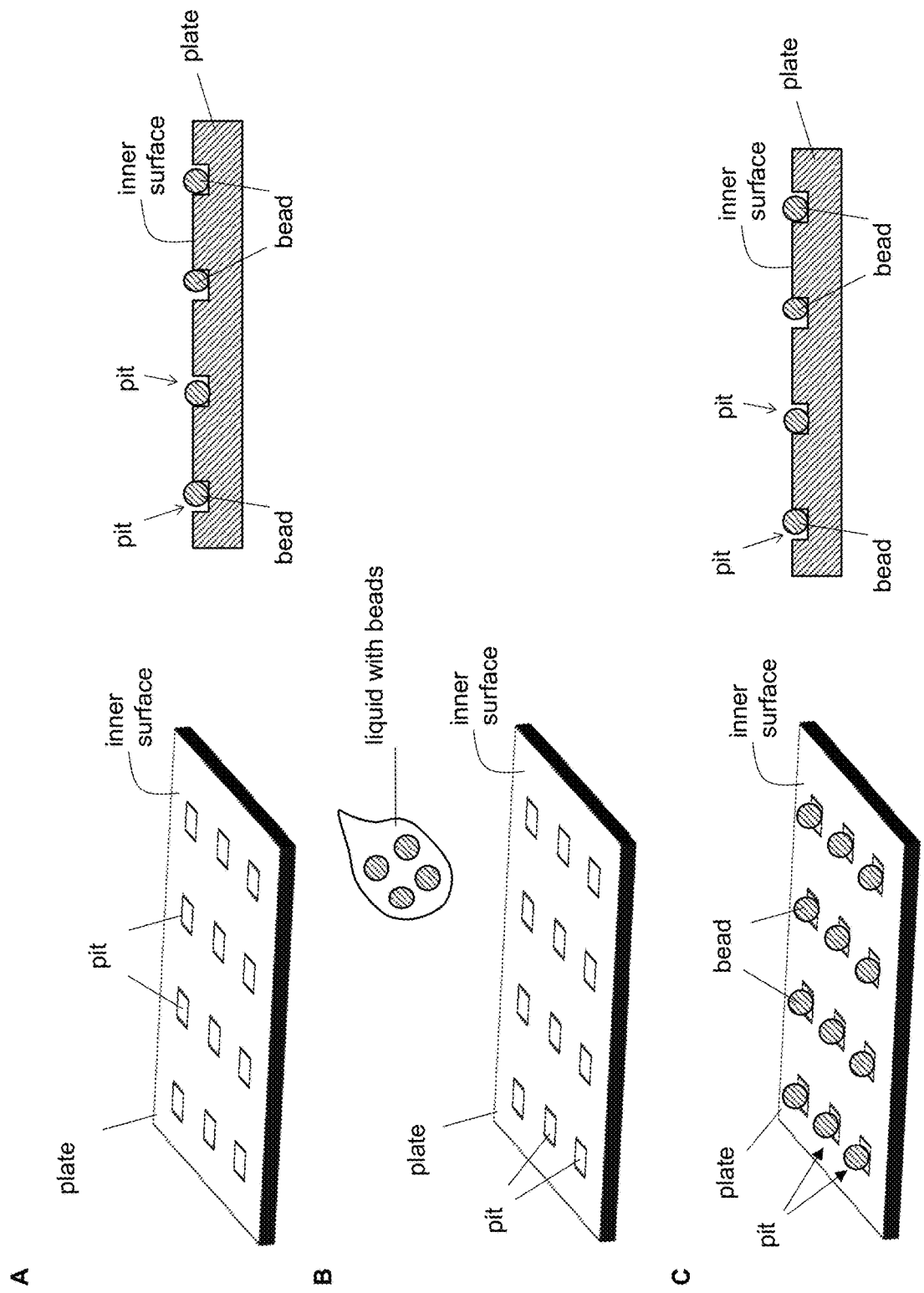
FIG. 11 provides schematic illustration of an exemplary process of making beads significantly periodically arranged on a plate.

FIG. 11 provides schematic illustration of an exemplary process of making beads significantly periodically arranged on a plate. As shown in the figure, the first step is to have a plate that has a plurality of pits periodically arranged on the plate's inner surface. Next, depositing a liquid that contains a plurality of beads on the inner surface of the plate. Last, drying the plate.

In some embodiments, the plate (pit plate) is hydrophilic. In some embodiments, the pits are hydrophilic. Initially during the drying process, due to capillary force on the ridge of the pit holding the liquid, the liquid film on the plate inner surface starts to dry out and shrink from the non-pit flat area of the inner surface, while the liquid inside the pits remains. Later, as the liquid continues to dry out, the film breaks into droplets that are either on the non-pit flat area, inside the pits, or partially covering both pit and the neighboring flat area. The droplets inside the pits have a low surface energy compared with the droplets on the flat area and the droplets partially covering both pit and the neighboring flat area. As a result of a combinatory action of the capillary force, the difference in surface energy, and potentially many other factors, the beads that are randomly distributed on the plate inner surface (mostly on the non-put flat area) are pushed into their neighboring pits. As the liquid continues to dry, the pits eventually become dry as well, while the beads are now located inside the periodically arranged pits.

In some embodiments, the beads are significantly periodically arranged. The term "significantly" as used herein in reference to the arrangement of the beads on the plate means that the percentage of the bead that are periodically arranged over the total number of beads on the plate is 50% or more, 60% or more, 70% or more, 80% or more, 90% or more, 95% or more, 96% or more, 97% or more, 98% or more, 99% or more, or 100%. In some embodiments, there are a certain number of pits that do not have beads therein. In some embodiments, the percentage of pits that do not have beads therein over the total number of pits on the sample contact area is 90% or less, 80% or less, 70% or less, 60% or less, 50% or less, 40% or less, 30% or less, 20% or less, 10% or less, 5% or less, 4% or less, 3% or less, 2% or less, 1% or less, or 0. In some embodiments, there are beads that are not inside the pits, but rather on the non-pit flat area of the plate. In some embodiments, the percentage of the beads that are not inside the pits, but on the non-pit flat area of the sample contact area of the plate is 50% or less, 40% or less, 30% or less, 20% or less, 10% or less, 5% or less, 4% or less, 3% or less, 2% or less, 1% or less, or 0.

2.4 Homogeneous Nucleic Acid Hybridization Assay

In addition to immunoassays, the present invention also finds use in homogeneous nucleic acid hybridization assays.

In some embodiments, in nucleic acid hybridization assays, the capture agent is oligonucleotide or oligomimetics capture probe. In some embodiments of the present invention, the concentration surface, protrusions, or beads are coated with the capture probes. The capture probes are complementary to one part of the nucleic acid analyte, therefore capturing the analyte to the surface. Further, the analyte is bound with a labeled detection probe that is complementary to another part of the analyte.

In some embodiments of the beads-enhanced speed test (BEST) for homogeneous nucleic acid hybridization assay, the first plate and the second plate are obtained for a homogeneous nucleic acid hybridization assay. Before starting the assay, the two plates are pre-treated as follows: capture probe is first immobilized on the beads, and then these beads are coated on the first plate; while labeled detection probe is coated on the second plate. For the assay, when the two plates are separated apart (in the open configuration), a sample suspected of containing the nucleic acid analyte is deposited on one of the plates (the first or second plate) or both plates (not shown). After the sample deposition, the two plates are then brought together and pressed against each other to enter the closed configuration. As discussed above, the detection probe, upon contacting the sample, is dissolved in the sample. And in the closed configuration, at least part of the sample is compressed into a layer of uniform thickness. In such a layer of uniform thickness, the capture probe on the beads and the diffusing detection probe both hybridize to the analyte, but at different locations thereof, thereby forming a capture probe-analyte-detection probe sandwich. As the detection probe is labeled with fluorophore (red asterisks), the attraction of the analyte and labeled probe around the surface of the beads due to base-pair interactions renders the local concentration of fluorescent signal surrounding the beads significantly higher than the ambient background. Imaging is performed after closing the two plates without washing.

In some embodiments, for the nucleic acid hybridization assays, the beads have a diameter of 100 nm, 500 nm, 1 µm, 5 µm, 50 µm, 500 µm, 1 mm or in a range between any two of the values. In some preferred embodiments, the beads have a diameter of in a range of 1 µm to 10 µm, or 10 µm to 50 µm.

In some embodiments, for the nucleic acid hybridization assays, the beads are made of polystyrene, polypropylene, polycarbonate, glass, metal or any other material whose surface can be modified to bind capture antibody, or any combination thereof.

In some embodiments, the concentration surface, protrusion, or beads are blocked by blocking agent that is configured to reduce the non-specific binding to the concentration surface, protrusion, or beads. In some embodiments, the blocking agent comprises bovine serum albumin (BSA), milk, sodium caseinate, or any other reagent that can block the non-specific binding, or any combination thereof.

Below is an exemplary procedure for homogeneous nucleic acid hybridization assay using the BEST technology according to some embodiments of the present invention:

1. Conjugation of capture probe to beads. Biotinylated capture probes are coated on streptavidin coated beads (Piece, 10 µm in diameter);
2. Blocking of beads. The capture probe coated beads are blocked by 4% BSA in PBS at 4° C. over night and washed by PBST for 6 times prior to use;
3. Coating first plate. 1 µL of beads from Step 2 (beads concentration $10^7$-$10^8$/mL) are dropped on glass slide (Fisher Scientific) and air dried at room temperature;
4. Homogeneous assay. 1 µL of sample containing target nucleic acid of interest and 1 µL of Cy5-labeled detection probe are dropped onto the area of coated beads on the glass slide. The mix is immediately covered by X-plate (second plate) with 10 µm pillars and incubated for 1 min;
5. Imaging. Without washing, the fluorescent images are taken by fluorescence microscope.

2.5 RHA for Homogeneous Competitive Assay

According to some embodiments of the present invention, the RHA also can be used for competitive assays, where the certain area (e.g. analyte concentration area, concentrating protrusion, or beads) capture the unlabeled analyte. In these cases, the unlabeled analyte competes with the labeled detection agent to bind to the capture agent. The signal of the capture analyte is distinguishable from the background signal in that the certain area with the capture agent (e.g. analyte concentration area, concentrating protrusion, or beads) exhibits lower signal level as compared to the unbound labeled detection agent in the background. The homogeneous does not use the step of washing. The homogeneous assay is also one step: drop the sample on one plate and close the plates, ready for reading the signal.

2.6. Hand Pressing

For the devices, apparatus, systems, and methods herein disclosed, human hands can be used for manipulating or handling of the plates and/or samples. In some embodiments, human hands can be used to press the plates into a closed configuration. In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in US Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, the plates are movable relative to each other into different configurations, including an open configuration and a closed configuration. In the open configuration, the two plates are partially or completely separated apart, the spacing between the plates is not regulated by the spacers, and the sample is deposited on one or both of the plates. In the closed configuration, at least part of the sample is compressed by the two plates into a layer of highly uniform thickness and is substantially stagnant relative to the plates, wherein the uniform thickness of the layer is confined by the sample contact areas of the two plates and is regulated by the plates and the spacers. In some embodiments, the force that presses the two plates into the closed configuration is an imprecise pressing force provided by human hand.

In some embodiments, the plates are conformably pressed. Conformable pressing refers to pressing, in certain embodiments by human hand, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers. In certain embodiments, a conformable pressing is a method that makes the pressure applied over an area is substantially constant regardless the shape variation of the outer surfaces of the plates. In certain embodiments, parallel pressing applies the pressures on the intended area at the same time, and a sequential pressing applies the pressure on a part of the intended area and gradually move to other area.

In some embodiments, the plates are pressed into a closed configuration by an imprecise force. In certain embodiments, the imprecise force is applied by human hand. In some embodiments, the force is an imprecise force that has a magnitude which is, at the time that the force is applied, either (a) unknown and unpredictable, or (b) cannot be known and cannot be predicted within an accuracy equal or better than 30% of the force applied. In some embodiments, the force is an imprecise force that has a magnitude which cannot, at the time that the force is applied, be determined within an accuracy equal or better than 30%, 40%, 50%, 70%, 100%, 200%, 300%, 500%, 1000%, 2000%, or any range between the two values.

3. Multiplexed Assays

It is another aspect of the present invention to provide devices and methods with multiplexing capability for homogeneous assays.

In some embodiments, the sample comprises more than one analyte of interest, and there is need to detect the more than one analytes simultaneously using the same device ("multiplexing").

In some embodiments, the device for multiplexed homogeneous assays comprises: a first plate, a second plate, and spacers. In some embodiments, the plates are movable relative to each other into different configurations, including an open configuration and a closed configuration. In some embodiments, each of the plates has, on its respective inner surface, a sample contact area for contacting a sample suspected of containing a first analyte and a second analyte. In some embodiments, one or both of the plates comprise the spacers, at least one of the spacers is inside the sample contact area, and the spacers have a predetermined substantially uniform height. In some embodiments, one or both of the plates comprise, on the respective inner surface, a plurality of first beads and second beads, wherein the first and second beads have first and second capture agents immobilized thereon, respectively. In some embodiments, the first and second capture agents are capable of binding to and immobilizing the first and second analytes, respectively.

In some embodiments, in the open configuration of the device for multiplexed assays, the two plates are partially or entirely separated apart, the spacing between the plates is not regulated by the spacers, and the sample is deposited on one or both of the plates.

In some embodiments, in the closed configuration of the device for multiplexed assays, at least part of the sample is compressed by the two plates into a layer of highly uniform thickness, the uniform thickness of the layer is confined by the inner surfaces of the plates and is regulated by the plates and the spacers, the analytes in the layer of uniform thickness are concentrated by the beads so that signal of the captured analytes on the beads is distinguishable from signal emanating from other area in the layer of uniform thickness.

In some embodiments, the assay is designed to detect analytes of two different species. In some embodiments, the number of analyte species the assay is designed to detect is 3, 4, 5, 6, 7, 8, 10 or more, 20 or more, 30 or more, 100 or more, or an integral number in a range between any two of these values.

In multiplexed assays, it is often critical to distinguish the signals from different assays. In some embodiments of the present invention, the signals of the captured first and second analytes are distinguishable from one another by one of the following designs or methods:

(1) different types of labels are attached to the analytes of different species directly or the different detection agents that bind to the analytes of corresponding species;

(2) different types of beads are used to capture analytes of different species, and the bead types are distinguishable by the detection methods; and (3) a combination of (1) and (2).

In some embodiments, the beads for different analytes (e.g. the first and second beads) are different in their sizes.

In some embodiments, the beads for different analytes (e.g. the first and second beads) are different in their optical properties selected from the group consisting of: photoluminescence, electroluminescence, and electrochemiluminescence, light absorption, reflection, transmission, diffraction, scattering, diffusion, surface Raman scattering, and any combination thereof.

In some embodiments, the beads for different analytes (e.g. the first and second beads) are different in their electric densities, and a detector that can detect electric density is used.

In some embodiments, beads of different colors are used to capture analytes of different species (symbolized by the different shapes in the sample). In this case, a detector with the capability of visualizing or imaging the sample under bright-field illumination is used to facilitate the virtual separation of signals from analytes of different species. For instance, in some embodiments, the bright-field images are superimposed with the fluorescent images to sort out the signals, when the assay signals (signal of the analytes or the bound detection agents) are fluorescent.

In some embodiments, beads of different sizes are used to capture analytes of different species (symbolized by the different shapes in the sample). In this case, a detector with the capability of detecting the geometric distribution of the signal of the capture analytes or visualizing or imaging the beads under bright-field illumination is used to facilitate the virtual separation of signals from analytes of different species. For instance, in some embodiments, the assay signals are fluorescent, a detector that can image the fluorescent signals is able to record the geometric distribution of the fluorescent signal on the surface of the beads. A skilled artisan can separate beads of different sizes based on the fluorescent images. In other cases, bright-field images of the beads are used to aid the separation of the signals.

In some embodiments, different labels are used to separate analyte of different species (symbolized by the different shapes in the sample). In this exemplary case, different fluorophores are attached to the detection agents that bind to analytes of different species. A detector that can image the sample under fluorescent mode and is equipped with emission filters with different wavelengths of light should be used to distinguish the signals of different analytes.

In some embodiments, beads of different colors are used to capture analytes of different species (symbolized by the different colors in the sample). In this case, a detector with the capability of visualizing or imaging the sample under bright-field illumination is used to facilitate the virtual separation of signals from analytes of different species. For instance, in some embodiments, the bright-field images are superimposed with the fluorescent images to sort out the signals, when the assay signals (signal of the analytes or the bound detection agents) are fluorescent.

In some embodiments, beads of different sizes are used to capture analytes of different species (symbolized by the different colors in the sample). In this case, a detector with the capability of detecting the geometric distribution of the signal of the capture analytes or visualizing or imaging the beads under bright-field illumination is used to facilitate the virtual separation of signals from analytes of different species. For instance, in some embodiments, the assay signals are fluorescent, a detector that can image the fluorescent signals is able to record the geometric distribution of the fluorescent signal on the surface of the beads. A skilled artisan can separate beads of different sizes based on the fluorescent images. In other cases, bright-field images of the beads are used to aid the separation of the signals.

In some embodiments, different labels are used to separate analyte of different species (symbolized by the different color in the sample). In this exemplary case, different fluorophores are attached to the detection agents that bind to analytes of different species. A detector that can image the sample under fluorescent mode and is equipped with emission filters with different wavelengths of light should be used to distinguish the signals of different analytes.

4. Assays, Capture Agent, and Detection Agent

In some embodiments, the assay is a sandwich assay, in which capture agent and detection agent are configured to bind to analyte at different locations thereof, forming capture agent-analyte-detection agent sandwich.

In some embodiments, the assay is a competitive assay, in which analyte and detection agent compete with each other to bind to the capture agent.

In some embodiments, the assay is an immunoassay, in which protein analyte is detected by antibody-antigen interaction. In some embodiments, the assay is a nucleic acid assay, in which nucleic acids (e.g. DNA or RNA) are detected by hybridization with complementary oligonucleotide probes.

In some embodiments, the assay utilizes light signals as readout. In some embodiments, the assay utilizes magnetic signals as readout. In some embodiments, the assay utilizes electric signals as readout. In some embodiments, the assay utilizes signals in any other form as readout.

In some embodiments, the light signal from the assay is luminescence selected from photoluminescence, electroluminescence, and electrochemiluminescence. In some embodiments, the light signal is light absorption, reflection, transmission, diffraction, scattering, or diffusion. In some embodiments, the light signal is surface Raman scattering. In some embodiments, the electrical signal is electrical impedance selected from resistance, capacitance, and inductance. In some embodiments, the magnetic signal is magnetic relaxivity. In some embodiments, the signal is any combination of the foregoing signal forms.

Figure 8:
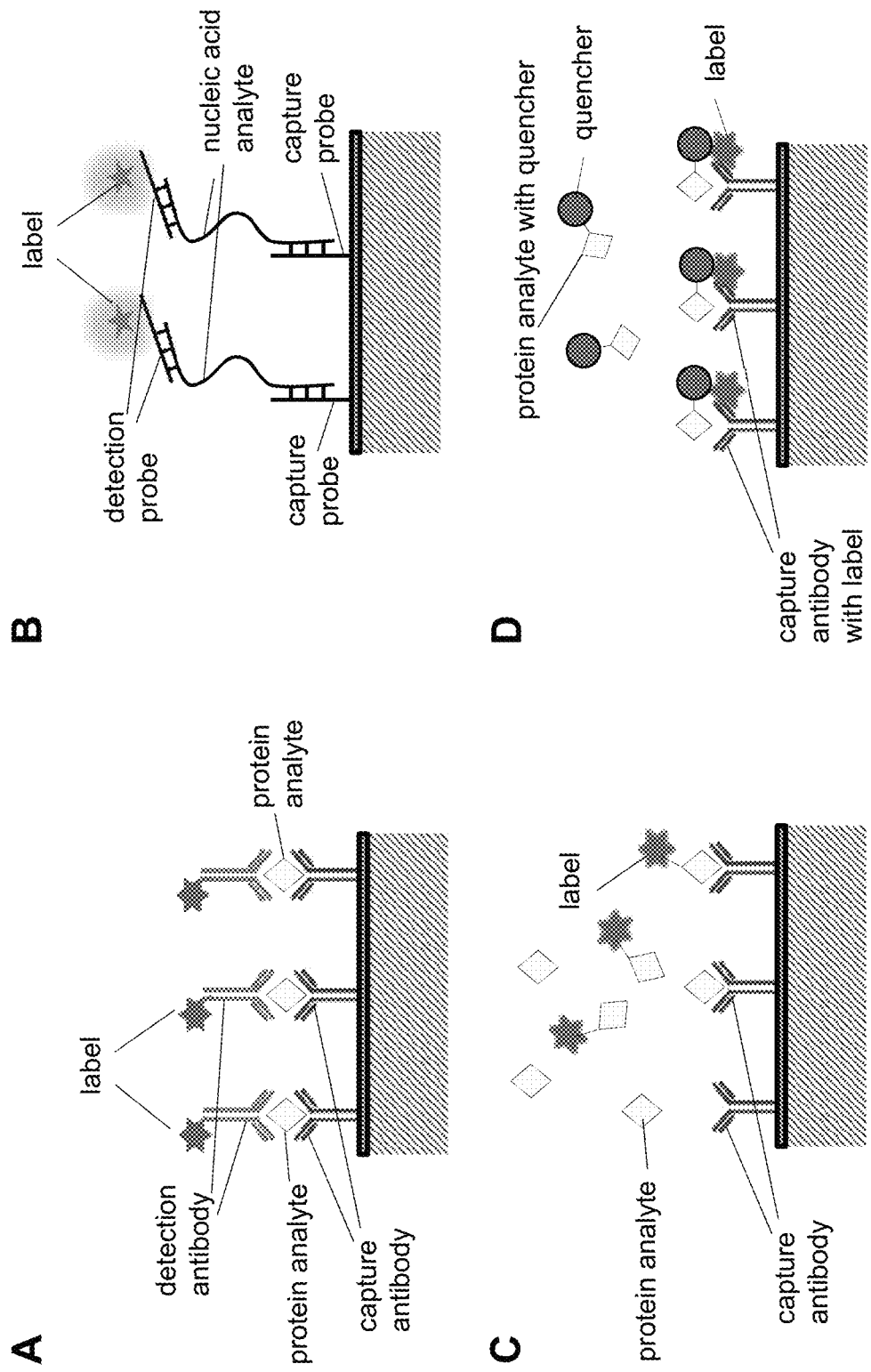
FIG. 8 illustrates examples of analyte concentration surfaces that capture analyte using a capture agent, and the captured analyte are further bound with a label. Panel (A) shows a protein concentration surface, where the capture agent is the capture antibody; panel (B) shows a nucleic acid concentration surface, where the capture agent is the capture probe; panel (C) shows a protein concentration surface, where the protein analyte is directly labeled; panel (D) shows a protein concentration surface, where the protein analyte is labeled with a quencher that quenches signal of the label associated with the capture antibody.

FIG. 8 illustrates examples of analyte concentration surfaces that capture analyte using a capture agent, and the captured analyte are further bound with a label. Panel (A) shows a protein concentration surface, which is coated with capture antibodies. The capture antibodies capture the protein analyte in a sample, which is further bound with labeled detection antibodies. In this case, the capture antibody and detection antibody are configured to bind to the protein analyte at its different locations, therefore forming a capture antibody-protein analyte-detection antibody sandwich. Panel (B) shows a nucleic acid concentration surface, which is coated with oligonucleotide capture probes. The capture probes are complementary to one part of the nucleic acid analyte, therefore capturing the analyte to the surface. Further, the analyte is bound with a labeled detection probe that is complementary to another part of the analyte. Panel (C) shows another case of protein concentration surface, where protein analyte is directly labeled by an optical label and captured by the capture antibodies that are coated on the concentration surface. Panel (D) shows another case of protein concentration surface, where protein analyte is bound with a quencher, which quenches the signal emitted by the label that is associated with the capture antibodies on the concentration surface. In this case, the concentration of the protein analyte to the concentration surface reduces the signal emanating from the concentration surface.

Figure 9:
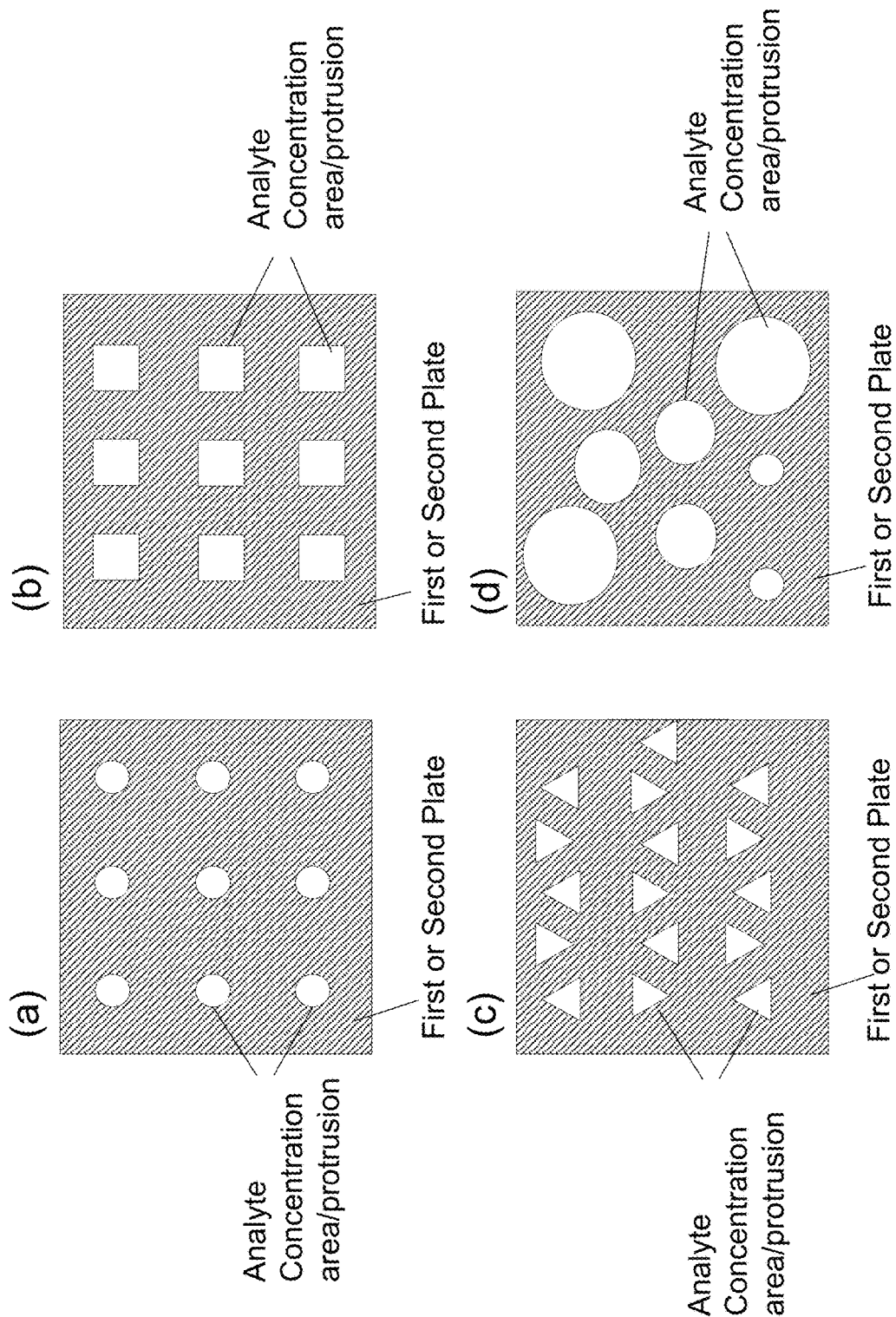
FIG. 9 Top view of the analyte concentration area/protrusion that are separated nano-/micro-islands on one or both of the plates with (i) round shape with square lattice (ii) rectangle shape with square lattice (iii) triangle shape with hexagonal lattice (iv) round shape with aperiodicity.

In some embodiments, the capture agent and the detection agent are configured to bind to the analyte at different locations thereof and to form a capture agent-analyte-detection agent sandwich that is immobilized to the separated nano-/micro-islands on one or both of the plates; wherein the shape of nano- or micro-islands are selected from the group consisting of sphere, rectangle, hexagon, and/or any other polyhedron, with lattice of square, hexagon, and/or any other lattices. FIG. 9 illustrates top views of separated nano/micro islands on one or both of the plates with (i) round shape with square lattice (ii) rectangle shape with square lattice (iii) triangle shape with hexagonal lattice (iv) round shape with aperiodicity.

In some embodiments, the material of protrusions that are nano or micro islands are selected from the group consisting of plastic as polystyrene, polypropylene, polycarbonate, PMMA, PET; metals as gold, aluminum, silver, copper, tin and/or their combinations; or any other material whose surface can be modified to be associated with the capture agent.

As discussed above, in some embodiments, the beads, the capture agent, and the detection agent are configured to render signal of the bead-captured analyte distinguishable from signal of free detection agent in the layer of uniform thickness. In some embodiments, it is critical to achieve the foregoing configuration, in that only if the signal from the sandwich structure is distinguishable from the "background" signal of the free detection agent in the layer of uniform thickness, one can use the detected signals as a readout of the presence and/or quantity of the analyte in the sample, thereby realizing the assay.

In some embodiments, the target analyte competes with the detection agent on the capture locations on beads. When more target analyte appears, beads become relative dark.

In some embodiments, the beads are associated with a label, and the detection agent is a quencher that is configured to quench signal of the beads-associated label when the detection agent is in proximity of the label. When beads capture the target analyte, the label on beads become quenched or dimed.

In some embodiments, the capture agent includes, but not limited to, protein, peptide, peptidomimetics, streptavidin, biotin, oligonucleotide, oligonucleotide mimetics, any other affinity ligand and any combination thereof. In some embodiments, the capture agent is an antibody. In some embodiments, the capture antibody is an anti-C Reactive Protein (CRP) antibody.

In some embodiments, the capture agent has a concentration that is sufficient to detect the presence and/or measure the amount of the analyte. In some embodiments, the capture agent has a concentration that is sufficient to immobilize the analyte.

In some embodiments, the detection agent includes, but not limited to, protein, peptide, peptidomimetics, streptavidin, biotin, oligonucleotide, oligonucleotide mimetics, any other affinity ligand and any combination thereof. In some embodiments, the detection agent is an antibody. In some embodiments, the detection antibody is an anti-CRP antibody.

In some embodiments, the detection antibody is configured to have a concentration in the layer of uniform thickness that is higher than analyte concentration in the sample. In some embodiments, the ratio of the detection antibody concentration over the analyte concentration is 1 or more, 2 or more, 5 or more, 10 or more, 20 or more, 30 or more, 50 or more, 100 or more, 200 or more, 300 or more, 500 or more, 1000 or more, or in a range between any two of these values.

In some embodiments, the detection antibody is labeled. In some embodiments, the label can be fluorescent, colorimetric or luminescent. In some embodiments, the detection antibody is labeled with a fluorophore. In some embodiments, the fluorophores include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 di sulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In some embodiments, the beads are treated with a protein stabilizer. In some embodiments, the beads can be deposited on the plate and dried (e.g. air-dried), further simplifying the process. In some embodiments, the detection antibody is placed on one of the plates and dried. In some embodiments, the plate with the detection antibody is treated with protein stabilizer. In some embodiments, the detection antibody with protein stabilizer is pre-printed on one of the plates and air dried.

In some embodiments, wherein the beads are prepared by:
(a) activating with N-Hydroxysuccinimide (NHS);
(b) blocking with a BSA solution; and
(c) incubating with a capture agent solution.

5. Detector, System and Smartphone-Based System

Another aspect of the present invention provides a system for homogeneous assay. In some embodiments, the system comprises the device as discussed above and a detector that detects the analyte in the layer of uniform thickness.

In some embodiments, detector detects a signal from the capture agent-analyte-detection agent sandwich indicative of the presence and/or quantity of the analyte.

In some embodiments, the signal is:
i. luminescence selected from photoluminescence, electroluminescence, and electrochemiluminescence;
ii. light absorption, reflection, transmission, diffraction, scattering, or diffusion;
iii. surface Raman scattering;
iv. electrical impedance selected from resistance, capacitance, and inductance;
v. magnetic relaxivity; or
vi. any combination of i-v.

Another aspect of the present invention provides a smartphone system for homogeneous assay. In some embodiments, the smartphone system comprises:
(a) a device of any aforementioned embodiment;
(b) a mobile communication device that comprises:
  i. one or a plurality of cameras for detecting and/or imaging the sample;
  ii. electronics, signal processors, hardware and software for receiving and/or processing the detected signal and/or the image of the sample and for remote communication; and
(c) an adaptor configured to hold the closed device and engageable to mobile communication device;
wherein when engaged with the mobile communication device, the adaptor is configured to facilitate the detection and/or imaging of the analyte in the sample at the closed configuration.

In some embodiments, the mobile communication device is configured to communicate test results to a medical professional, a medical facility or an insurance company.

In some embodiments, the mobile communication device is further configured to communicate information on the subject with the medical professional, medical facility or insurance company.

In some embodiments, the mobile communication device is configured to receive a prescription, diagnosis or a recommendation from a medical professional.

In some embodiments, the mobile communication device communicates with the remote location via a wifi or cellular network.

In some embodiments, the mobile communication device is a mobile phone.

In some embodiments, the images can be taken by a camera that is part of a mobile device. In some embodiments, the mobile device is a smart phone.

Figure 1B:
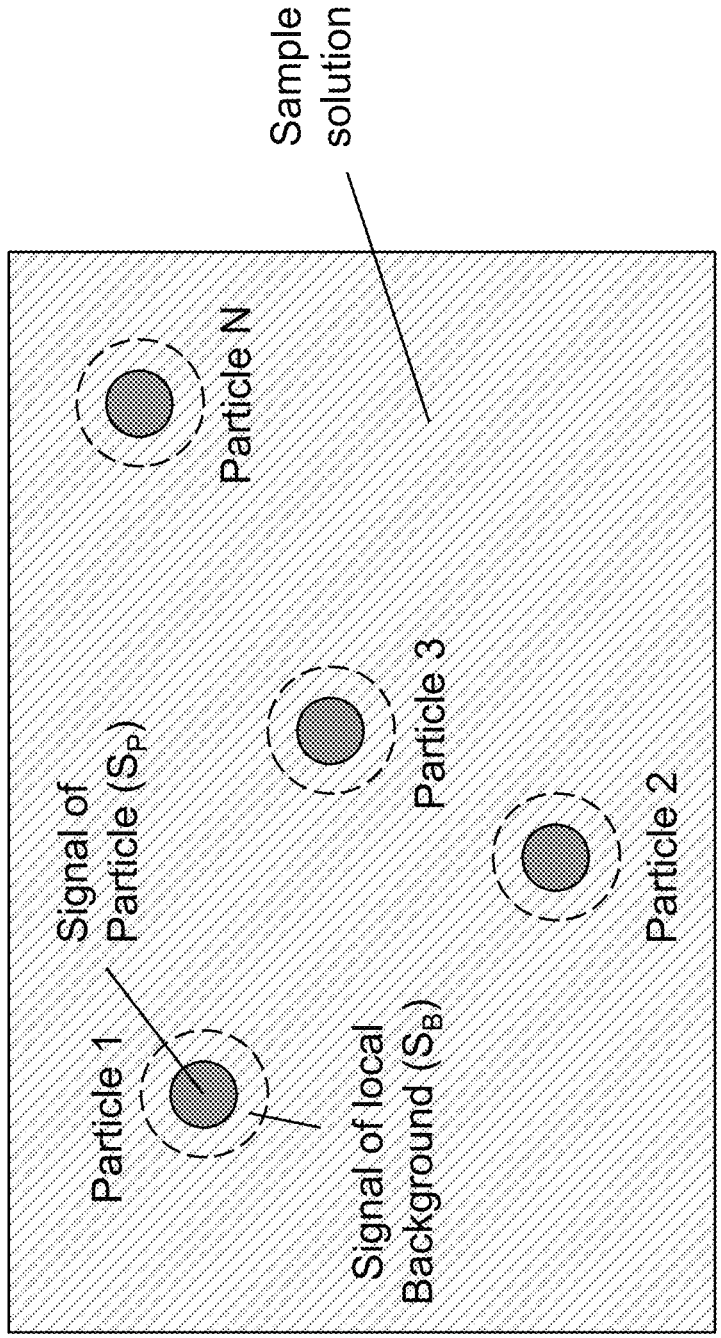
FIG. 1B illustrates local reading as used in embodiments of the present disclosure. Signal from each particle region ($S_P$) and the signal of area around the particle (local background $S_B$) is measured. The true Signal of Assay $S_A$ is determined as $S_A=S_P-S_B$.

In the local reading approach, as shown in FIG. 1B, one or more than one particles will be measured for the following two measurements: (a) the signal from the particle region ($S_P$). It can be from the whole particle region or a designated area of the particle region; and (b) the signal of area around the particle (local background $S_B$). It can be from the whole area around the particle or a designated area. The definition of "around" can be a distance of 0.01D, 0.1D, 0.2D, 0.5D, 1D, 2D, 5D, 10D, 50D or a range between any two of the values to the outer surface of the particle, in which "D" is the average diameter of the particle. The true Signal of Assay ($S_A$) for each particle can be determined as $S_A = S_P - S_B$. The assay signal from each CROF ($S_{CROF}$) can be the average of multiple particles. It can be all particles on a whole CROF or particles in a designated region of a CROF (e.g., $S_{CROF}$=Average ($S_{A1}, S_{A2}, S_{A3} \ldots S_{An}$))

6. Analyte, Sample and Application

In some embodiments, the analyte to be detected in the homogeneous assay includes, but not limited to, cells, viruses, proteins, peptides, DNAs, RNAs, oligonucleotides, and any combination thereof.

In some embodiments, the present invention finds use in detecting biomarkers for a disease or disease state. In certain instances, the present invention finds use in detecting biomarkers for the characterization of cell signaling pathways and intracellular communication for drug discovery and vaccine development. For example, the present invention may be used to detect and/or quantify the amount of biomarkers in diseased, healthy or benign samples. In certain embodiments, the present invention finds use in detecting biomarkers for an infectious disease or disease state. In some cases, the biomarkers can be molecular biomarkers, such as but not limited to proteins, nucleic acids, carbohydrates, small molecules, and the like. The present invention find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The present invention has applications in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

In some embodiments, the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

In some embodiments, the sample is an environmental gaseous sample from a source selected from the group consisting of: the air, underwater heat vents, industrial exhaust, vehicular exhaust, and any combination thereof.

In some embodiments, the sample is a foodstuff sample selected from the group consisting of: raw ingredients, cooked food, plant and animal sources of food, preprocessed food, and partially or fully processed food, and any combination thereof.

7. Examples of Present Invention

Multiplexed BEST
NA1. A device for a homogeneous assay, comprising:
a first plate, a second plate, spacers, a plurality of particles, and capture agents, wherein:
  vi. the first and second plates are movable relative to each other into different configurations, including an open configuration and a closed configuration;
  vii. each of the plates has, on its respective inner surface, a sample contact area for contacting a sample suspected of containing an analyte;
  viii. the first plate comprises the spacers that are fixed on its inner surface, at least one of the spacers is inside the sample contact area, the spacers have a predetermined substantially uniform height that is equal to 100 um or less;
  ix. the plurality of particles has the capture agents immobilized on their surface, wherein the capture agents are capable of specifically binding and immobilizing the analyte; and
  x. the plurality of particles are (a) distributed on the sample contact area of the first plate, except the areas occupied by the spacers, and (b) are temporarily or permanently fixed on the first plate;
wherein in the open configuration, the two plates are partially or entirely separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

NB1. A device for a homogeneous assay, comprising:
a first plate, a second plate, spacers, a plurality of particles, and capture agents, wherein:
  vi. the first and second plates are movable relative to each other into different configurations, including an open configuration and a closed configuration;
  vii. each of the plates has, on its respective inner surface, a sample contact area for contacting a sample suspected of containing a analyte;
  viii. one or both plates comprises the spacers that are fixed on its inner surface, at least one of the spacers is inside the sample contact area, the spacers have a predetermined substantially uniform height that is equal to 100 um or less;
  ix. the plurality of particles has the capture agents immobilized on their surface, wherein the capture agents are capable of specifically binding and immobilizing the analyte; and
  x. the plurality of particles are (a) distributed on a sample contact area of the first, and (b) are temporarily or permanently fixed on the plate;
wherein in the open configuration, the two plates are partially or entirely separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

NC1. The device of any prior embodiment, wherein the distribution of the plurality of particles on the plate is random.

NC2. The device of any prior embodiment, wherein the plurality of particles is fixed on the plate and has periodic distribution.

NC3. The device of any prior embodiment, wherein the spacer has a flat top.

NC4. The device of any prior embodiment, wherein the plurality of particles is temporarily fixed on the first plate, and in an open configuration the sample is deposited on the first plate before the two plates are brought into the closed configuration.

NC5. The device of any prior embodiment, wherein the thickness of the spacer is configured such that, in a closed configuration, for a certain concentration of the analytes in the sample, at least one area of the uniform thickness sample that contains one of the particle becomes optically distinguishable, when viewed outside of the sample layer, from its neighboring area that does not contain a particle.

NC6. The device of any prior embodiment, the device comprising two plates and spacers, wherein the pressing is by human hand.

NC7. The device of any prior embodiment, wherein the diameter of one or more of the plurality of particles is equal to the height of the spacers.

NC8. The device of any prior embodiment, wherein the spacer height is about 10 um.

NC9. The device of any prior embodiment, wherein the spacer height is about 5 um.

NC10. The device of any prior embodiment, wherein the spacer height is between about 0.1 um and about 15 um.

NC11. The device of any prior embodiment, wherein the spacer height is between about 0.1 um and about 3 um.

NC12. The device of any prior embodiment, wherein at least a portion of the inner surface of one plate or both plate is hydrophilic.

NC13. The device of any prior embodiment, wherein the inter spacer distance is periodic.

NC14. The device of any prior embodiment, wherein the sample is a deposition directly from a subject to the plate without using any transferring devices.

NC15. The device of any prior embodiment, wherein after the sample deformation at a closed configuration, the sample maintains the same final sample thickness, when some or all of the compressing forces are removed.

NC16. The device of any prior embodiment, wherein the spacers have pillar shape and nearly uniform cross-section.

NC17. The device of any prior embodiment, wherein the inter spacer distance (SD) is equal or less than about 120 um (micrometer).

NC18. The device of any prior embodiment, wherein the inter spacer distance (SD) is equal or less than about 100 um (micrometer).

NC19. The device of any prior embodiment, wherein the fourth power of the inter-spacer-distance (ISD) divided by the thickness (h) and the Young's modulus (E) of the flexible plate (ISD^4/(hE)) is 5×10^6 um^3/GPa or less.

NC20. The device of any prior embodiment, wherein the fourth power of the inter-spacer-distance (ISD) divided by the thickness (h) and the Young's modulus (E) of the flexible plate (ISD^4/(hE)) is 5×10^5 um3/GPa or less.

NC21. The device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

NC22. The device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

NC23. The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.

ND1. A method of performing a homogeneous assay, comprising the steps of:
  (a) obtaining a sample suspected of containing an analyte;
  (b) obtaining a device of any prior embodiment, wherein the capture agents are capable of specifically binding an binding site of the analyte;
  (c) having optical labels on at least a part of the sample contact areas of the device, wherein the optical labels are capable of binding to the analytes;
  (d) depositing the sample on one or both of the plates when the plates are in an open configuration, wherein in an open configuration;
  (e) after (d), bringing the two plates together and pressing the plates into a closed configuration, at least part of the sample is compressed by the two plates into a layer of highly uniform thickness, the uniform thickness of the layer is confined by the inner surfaces of the plates and is regulated by the plates and the spacers;
  (f) while the plates are in the closed configuration, analyzing the analyte in the layer of uniform thickness, wherein the analyzing comprises:
    i. measuring, from outside of the sample layer, the total light signal from (a) a particle area that is an area of the sample layer that contains one particle and from (b) a surrounding area that is the area of the sample layer which is around the particle area, wherein the surrounding area is 50 D within the edge of the particle, wherein the D is the diameter of the particle; and
    ii. measuring the total light signal from each of the particle area and the surrounding area of at least two different particle areas.

ND2. The method of any prior embodiment, wherein the particle area for the total light signal measurement has substantially the same area as the particle diameter.

ND3. The method of any prior embodiment, wherein the particle area for the total light signal measurement is smaller than the area defined by the particle diameter.

ND4. The method of any prior embodiment, wherein the analyzing the analyte in the uniform sample layer comprises averaging of the total light signal from each area.

ND5. The method of any prior embodiment, wherein the analyzing the analyte in the uniform sample layer comprises (i) taking a ratio of the total light signal of each particle area to that of its surrounding area, and (ii) averaging the ratio of all particle area and surround area pairs.

ND6. The method of any prior embodiment, wherein the time from the end of the sample deposition to the end of the plates being pressed into the closed configuration is less than 15 seconds.

ND7. The method of any prior embodiment, wherein the time from the end of the sample deposition to the end of the plates being pressed into the closed configuration is less than 5 seconds.

NE1. An apparatus for homogenous assaying an analyte in a sample, comprising:
  i. a device of any prior embodiment; and
  ii. one or more imagers that image at least a part of the sample contact area.

NF1. A device for rapid multiplexed homogeneous assay, comprising:
  a first plate, a second plate, and spacers, wherein:
  i. the plates are movable relative to each other into different configurations, including an open configuration and a closed configuration;
  ii. each of the plates has, on its respective inner surface, a sample contact area for contacting a sample suspected of containing a first analyte and a second analyte;
  iii. one or both of the plates comprise the spacers, at least one of the spacers is inside the sample contact area, and the spacers have a predetermined substantially uniform height;
  iv. one or both of the plates comprise, on the respective inner surface, a plurality of first particles and second particles, wherein the first and second particles have first and second capture agents immobilized thereon, respectively; and
  v. the first and second capture agents are capable of binding to and immobilizing the first and second analytes, respectively;
    wherein in the open configuration, the two plates are partially or entirely separated apart, the spacing between the plates is not regulated by the spacers, and the sample is deposited on one or both of the plates; and
    wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers, the analytes in the layer of uniform thickness are concentrated by the particles so that signal of the captured analytes on the particles is distinguishable from signal emanating from other area in the layer of uniform thickness.

NG1. A smartphone system for homogeneous assay, comprising:
  (a) a device of any prior embodiment;
  (b) a mobile communication device that comprises:
    i. one or a plurality of cameras for detecting and/or imaging the sample;
    ii. electronics, signal processors, hardware and software for receiving and/or processing the detected signal and/or the image(s) of the sample and for remote communication; and
  (c) an adaptor that is configured to accommodate the device that is in the closed configuration and be engageable to the mobile communication device;
    wherein when engaged with the mobile communication device, the adaptor is configured to facilitate the detection and/or imaging of the analyte in the sample.

NH1. The device, smartphone system, and method of any prior embodiments, wherein the first and second particles are different.

NH2. The device, smartphone system, and method of any prior embodiments, wherein the first and second particles are different in their sizes.

NH3. The device, smartphone system, and method of any prior embodiments, wherein the first and second particles are different in their optical properties selected from the group consisting of: photoluminescence, electroluminescence, and electrochemiluminescence, light absorption, reflection, transmission, diffraction, scattering, diffusion, surface Raman scattering, and any combination thereof.

NH4. The device, smartphone system, and method of any prior embodiments, wherein the first and second particles are different in their electric densities.

NH5. The device, smartphone system, and method of any prior embodiments, wherein the first and second particles are the same, and wherein the signals from the first and second analytes are different.

Method of Making Plate with Periodically Arranged Particles

NJ1. A method of making a plate with periodically arranged particles, comprising the steps of:
  (1) having a plate that comprises a plurality of pits on its inner surface, wherein the pits are periodically arranged;
  (2) depositing a liquid that contains a plurality of particles on the inner surface of the plate; and
  (3) drying the plate, during which process the particles are re-distributed inside the pits due to at least the capillary force on the ridge of the pits.

Analyte Concentration Area:

AA1-1. A device for rapid homogeneous assay, comprising:
  a first plate, a second plate, and spacers, wherein:
  i. the plates are movable relative to each other into different configurations, including an open configuration and a closed configuration;
  ii. each of the plates has, on its respective inner surface, a sample contact area for contacting a sample suspected of comprising an analyte;
  iii. one or both of the plates comprise the spacers, at least one of the spacers is inside the sample contact area, and the spacers have a predetermined substantially uniform height; and
  iv. one or both of the plates comprise, on the respective inner surface, one or a plurality of analyte concentration areas that have capture agent immobilized thereon, wherein the capture agent is capable of binding to and immobilizing the analyte;
    wherein in the open configuration, the two plates are partially or entirely separated apart, the spacing between the plates is not regulated by the spacers, and the sample is deposited on one or both of the plates; and
    wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers and the analyte in the layer of uniform thickness is concentrated in the analyte concentration area so that signal of captured analyte in the analyte concentration areas is distinguishable from signal emanating from non-analyte concentration area in the layer of uniform thickness.

Concentration Protrusion:

AA2. The device of any prior embodiment, wherein one or both of the plates comprise one or a plurality of protrusions extending from the respective inner surface, and wherein each protrusion has a height smaller than the spacers and comprises the analyte concentration area on at least one of its surfaces.

Particles:
AB1. A device for rapid homogeneous assay, comprising:
a first plate, a second plate, and spacers, wherein:
  i. the plates are movable relative to each other into different configurations, including an open configuration and a closed configuration;
  ii. each of the plates has, on its respective inner surface, a sample contact area for contacting a sample suspected of comprising an analyte;
  iii. one or both of the plates comprise the spacers, at least one of the spacers is inside the sample contact area, and the spacers have a predetermined substantially uniform height; and
  iv. one or both of the plates comprise, on the respective inner surface, a plurality of particles that have capture agent immobilized thereon, wherein the capture agent is capable of binding to and immobilizing the analyte;
  wherein in the open configuration, the two plates are partially or entirely separated apart, the spacing between the plates is not regulated by the spacers, and the sample is deposited on one or both of the plates; and
  wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers, the analyte in the layer of uniform thickness is concentrated by the particles so that signal of the captured analyte on the particles is distinguishable from signal emanating from other area in the layer of uniform thickness.

System:
C1. A system for rapid homogeneous assay, comprising:
  (a) a device of any prior embodiment; and
  (b) a detector that detects signals from the capture agent-bound analyte indicative of the presence and/or quantity of the analyte in the layer of uniform thickness.

Smartphone System:
D1. A smartphone system for rapid homogeneous assay, comprising:
  (a) a device of any prior embodiment; and
  (b) a mobile communication device that comprises:
    i. one or a plurality of cameras for detecting and/or imaging the sample;
    ii. electronics, signal processors, hardware and software for receiving and/or processing the detected signal and/or the image of the sample and for remote communication; and
  (c) an adaptor that is configured to hold the closed device and engageable to mobile communication device;
  wherein when engaged with the mobile communication device, the adaptor is configured to facilitate the detection and/or imaging of the analyte in the sample at the closed configuration.

Method:
AE1. A method of performing a rapid homogeneous assay, comprising the steps of:
  (a) obtaining a sample suspected of containing an analyte;
  (b) obtaining a device of any prior embodiment;
  (c) depositing the sample on one or both of the plates when the plates are in the open configuration;
  (d) after (c), bringing the two plates together and pressing the plates into the closed configuration; and
  (e) while the plates are at the closed configuration, detecting and analyzing the analyte in the layer of uniform thickness.

AE2. A method of analyzing the image for a rapid homogeneous assay, comprising the steps of:
  (a) obtaining an image of the signal in any prior embodiment at the closed configuration, wherein the image is selected from the group consisting of bright field image, dark field image, fluorescence image, and phosphorescence image;
  (b) analyzing the image, identifying particles in the image, and extracting information of particles size, signal intensity of particles, distance between particles, distribution of particles, and number of particles; and
  (c) deducing analyte concentration by analyzing the extracted information from step (b) and calculating parameters of the particles.

E1. A method of performing a homogeneous assay, comprising the steps of:
  (a) obtaining a sample suspected of containing an analyte;
  (b) obtaining a first and second plates that are movable relative to each other into different configurations, including an open configuration and a closed configuration, wherein:
  v. each of the plates has, on its respective inner surface, a sample contact area for contacting the sample,
  vi. one or both of the plates comprise the spacers, and at least one of the spacers is inside the sample contact area;
  vii. one or both of the plates comprise, on the respective inner surface, a plurality of particles that have capture agent immobilized thereon, wherein the capture agent is capable of binding to and immobilizing the analyte; and
  viii. one or both of the plates comprise, on the respective inner surface, detection agent that is configured to, upon contacting the sample, be dissolved in the sample and bind to the analyte;
  wherein the spacers have a predetermined substantially uniform height;
  (c) depositing the sample on one or both of the plates when the plates are in an open configuration, wherein in the open configuration the two plates are partially or entirely separated apart and the spacing between the plates is not regulated by the spacers;
  (d) after (c), bringing the two plates together and pressing the plates into a closed configuration, wherein in the closed configuration: at least part of the sample is compressed by the two plates into a layer of highly uniform thickness, the uniform thickness of the layer is confined by the inner surfaces of the two plates and is regulated by the spacers and the plates; and
  (e) while the plates are at the closed configuration, detecting and analyzing the analyte in the layer of uniform thickness,
    wherein the capture agent and the detection agent are configured to bind to the analyte at different locations thereof and to form a capture agent-analyte-detection agent sandwich that is immobilized to the particle; and
    wherein the particles, the capture agent, and the detection agent are configured to render signal from the particle-associated capture agent-analyte-detection agent sandwich distinguishable from signal of free detection agent in the layer of uniform thickness.

Embodiments Defining Diffusion Parameters

AA1-2. A device for rapid homogenous assay, comprising:
a first plate, a second plate, and spacers, wherein:
i. the plates are movable relative to each other into different configurations, including an open configuration and a closed configuration;
ii. each of the plates has, on its respective inner surface, a sample contact area for contacting a sample suspected of comprising an analyte;
iii. one or both of the plates comprise the spacers, at least one of the spacers is inside the sample contact area, and the spacers have a predetermined substantially uniform height of 200 um or less; and
iv. one or both of the plates comprise, on the respective inner surface, one or a plurality of analyte concentration areas that has capture agent immobilized thereon, wherein the capture agent is capable of binding the analyte;
wherein the spacers have a height that is equal to or less than 4 times of a diffusion parameter, wherein the diffusion parameter is square root of the intended assay time multiplying diffusion constant of the analyte in the sample and wherein the intended assay time is equal to or less than 240 seconds;
wherein the average distance between two neighboring analyte concentration areas is equal to or less than 4 times of the diffusion parameter;
wherein in the open configuration, the two plates are partially or entirely separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers and the analyte in the layer of uniform thickness is concentrated in the concentration area so that signal of captured analyte in the concentration areas is distinguishable from signal emanating from non-concentration area in the layer of uniform thickness.

AA2-2. The device of any prior embodiment, wherein one or both of the plates comprise one or a plurality of protrusions extending from the respective inner surface, and wherein each protrusion has a height smaller than the spacers and comprises the analyte concentration area on at least one of its surfaces.

AB1-2. A device for rapid homogeneous assay, comprising:
a first plate, a second plate, and spacers, wherein:
i. the plates are movable relative to each other into different configurations, including an open configuration and a closed configuration;
ii. each of the plates has, on its respective inner surface, a sample contact area for contacting a sample suspected of comprising an analyte;
iii. one or both of the plates comprise the spacers, at least one of the spacers is inside the sample contact area, and the spacers have a predetermined substantially uniform height; and
iv. one or both of the plates comprise, on the respective inner surface, a plurality of particles that have capture agent immobilized thereon, wherein the capture agent is capable of binding to and immobilizing the analyte;
wherein the spacers have a height that is equal to or less than 3 times of a diffusion parameter, wherein the diffusion parameter is square root of the intended assay time multiplying diffusion constant of the analyte in the sample and wherein the intended assay time is equal to or less than 240 seconds;
wherein the average distance between two neighboring particles is equal to or less than 2 times of the diffusion parameter;
wherein in the open configuration, the two plates are partially or entirely separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers and the analyte in the layer of uniform thickness is concentrated in the concentration area so that signal of captured analyte in the concentration areas is distinguishable from signal emanating from non-concentration area in the layer of uniform thickness.

AE1-2. A method of performing a rapid homogeneous assay, comprising the steps of:
(a) obtaining a sample suspected of containing an analyte;
(b) obtaining a device of any prior embodiment;
(c) depositing the sample on one or both of the plates when the plates are in the open configuration;
(d) after (c), bringing the two plates together and pressing the plates into the closed configuration; and
(e) after step (d), incubating the assay for a time equal to or longer than the intended assay time, detecting and analyzing the analyte in the layer of uniform thickness.

DP1. The device, kit, system, smartphone system, and method of any prior embodiments, wherein the intended assay time is in the range of 0.1-240 sec.

DP2-1. The device, kit, system, smartphone system, and method of any prior embodiments, wherein the intended assay time is in the range of 1-60 sec.

DP2-2. The device, kit, system, smartphone system, and method of any prior embodiments, wherein the intended assay time is equal to or less than 30 sec.

DP2-3. The device, kit, system, smartphone system, and method of any prior embodiments, wherein the intended assay time is equal to or less than 10 sec.

DP2-4. The device, kit, system, smartphone system, and method of any prior embodiments, wherein the intended assay time is equal to or less than 5 sec.

DP-5. The device, kit, system, smartphone system, and method of any prior embodiments, wherein the intended assay time is equal to or less than 1 sec.

DP3. The device, kit, system, smartphone system, and method of any prior embodiments, wherein the average distance between two neighboring analyte concentration areas or particles is in the range of 50 nm-200 um.

DP4-1. The device, kit, system, smartphone system, and method of any prior embodiments, wherein the average distance between two neighboring analyte concentration areas or particles is in the range of 500 nm-20 um.

DP4-2. The device, kit, system, smartphone system, and method of any prior embodiments, wherein the average distance between two neighboring analyte concentration areas or particles is in the range of 500 nm-10 um.

DP4-3. The device, kit, system, smartphone system, and method of any prior embodiments, wherein the average distance between two neighboring analyte concentration areas or particles is in the range of 500 nm-5 um.

DP5. The device, kit, system, smartphone system, and method of any prior embodiments, wherein the ratio of the spacers' height versus the diffusion parameter is in the range of 0.01-2.

DP6-1. The device, kit, system, smartphone system, and method of any prior embodiments, wherein the ratio of the spacers' height versus the diffusion parameter is in the range of 0.1-1.5.

DP6-2. The device, kit, system, smartphone system, and method of any prior embodiments, wherein the ratio of the spacers' height versus the diffusion parameter is in the range of 0.01-0.5.

DP6-3. The device, kit, system, smartphone system, and method of any prior embodiments, wherein the ratio of the spacers' height versus the diffusion parameter is in the range of 0.01-0.2.

DP6-4. The device, kit, system, smartphone system, and method of any prior embodiments, wherein the ratio of the spacers' height versus the diffusion parameter is in the range of 0.01-0.1.

DP7. The device, kit, system, smartphone system, and method of any prior embodiments, wherein the ratio of the average distance between two neighboring analyte concentration areas or particles versus the diffusion parameter is in the range of 0.01-5.

DP8-1. The device, kit, system, smartphone system, and method of any prior embodiments, wherein the ratio of the average distance between two neighboring analyte concentration areas or particles versus the diffusion parameter is in the range of 0.01-1.5.

DP8-2. The device, kit, system, smartphone system, and method of any prior embodiments, wherein the ratio of the average distance between two neighboring analyte concentration areas or particles versus the diffusion parameter is in the range of 0.01-1.

DP8-3. The device, kit, system, smartphone system, and method of any prior embodiments, wherein the ratio of the average distance between two neighboring analyte concentration areas or particles versus the diffusion parameter is in the range of 0.01-0.5.

DP8-4. The device, kit, system, smartphone system, and method of any prior embodiments, wherein the ratio of the average distance between two neighboring analyte concentration areas or particles versus the diffusion parameter is in the range of 0.01-0.2.

DP8-5. The device, kit, system, smartphone system, and method of any prior embodiments, wherein the ratio of the average distance between two neighboring analyte concentration areas or particles versus the diffusion parameter is in the range of 0.01-0.1.

DP9-1. The device, kit, system, smartphone system, and method of any prior embodiments, wherein the ratio of the average distance between two neighboring analyte concentration areas or particles versus the diffusion parameter is in the range of 0.01-0.5, and the ratio of the spacers' height versus the diffusion parameter is in the range of 0.01-0.2.

DP9-2. The device, kit, system, smartphone system, and method of any prior embodiments, wherein the ratio of the average distance between two neighboring analyte concentration areas or particles versus the diffusion parameter is in the range of 0.01-1, and the ratio of the spacers' height versus the diffusion parameter is in the range of 0.01-0.5.

DP9-3. The device, kit, system, smartphone system, and method of any prior embodiments, wherein the ratio of the average distance between two neighboring analyte concentration areas or particles versus the diffusion parameter is in the range of 0.01-2, and the ratio of the spacers' height versus the diffusion parameter is in the range of 0.01-1.

DP9-4. The device, kit, system, smartphone system, and method of any prior embodiments, wherein the ratio of the average distance between two neighboring analyte concentration areas or particles versus the diffusion parameter is in the range of 0.01-4, and the ratio of the spacers' height versus the diffusion parameter is in the range of 0.01-1.

DP10-1. The device, kit, system, smartphone system, and method of any prior embodiments, wherein the ratio of the average distance between two neighboring analyte concentration areas or particles versus the diffusion parameter is in the range of 0.01-0.5, the ratio of the spacers' height versus the diffusion parameter is in the range of 0.01-0.2, and the intended assay time is equal to or less than 120 sec.

DP10-2. The device, kit, system, smartphone system, and method of any prior embodiments, wherein the ratio of the average distance between two neighboring analyte concentration areas or particles versus the diffusion parameter is in the range of 0.01-1; the ratio of the spacers' height versus the diffusion parameter is in the range of 0.01-0.5, and the intended assay time is equal to or less than 60 sec.

DP10-3. The device, kit, system, smartphone system, and method of any prior embodiments, wherein the ratio of the average distance between two neighboring analyte concentration areas or particles versus the diffusion parameter is in the range of 0.01-2; the ratio of the spacers' height versus the diffusion parameter is in the range of 0.01-1; and the intended assay time is equal to or less than 30 sec.

DP10-4. The device, kit, system, smartphone system, and method of any prior embodiments, wherein the ratio of the average distance between two neighboring analyte concentration areas or particles versus the diffusion parameter is in the range of 0.01-4; the ratio of the spacers' height versus the diffusion parameter is in the range of 0.01-1; and the intended assay time is equal to or less than 30 sec.

More:

(Sandwich Assay)

AA1 The device, kit, system, smartphone system, and method of any prior embodiments, wherein the analyte is labeled by detection agent that selectively binds to the analyte and is associated with a label.

AA1.1 The device, kit, system, smartphone system, and method of any prior embodiments, wherein the detection agent is coated on the inner surface(s) of one or both of the plates, and is configured to, upon contacting the sample, be dissolved and diffuse in the sample.

AA1.2 The device, kit, system, smartphone system, and method of any prior embodiments, wherein the detection agent is pre-loaded into the sample before the sample is deposited on the plate(s).

AA1.3 The device, kit, system, smartphone system, and method of any prior embodiments, wherein the capture agent and the detection agent are configured to bind to the analyte at different locations thereof and form capture agent-analyte-detection agent sandwich.

(Competitive Assay)

AA2 The device, kit, system, smartphone system, and method of any prior embodiments, wherein the analyte competes with a detection agent to bind to the capture agent, and wherein the detection agent is labeled.

AA3 The device, kit, system, smartphone system, and method of any prior embodiments, wherein one or both of the plates comprise, on the respective inner surface, a signal amplification surface that amplify the signal in proximity to the amplification surface.

A2 The device, kit, system, smartphone system, and method of any prior embodiments, wherein the particles are the spacers that regulate the thickness of the layer at the closed configuration.

A2.1 The device, kit, system, smartphone system, and method of any prior embodiments, wherein the particles are micro- or nano-particles having an average diameter in the range of 1 nm to 200 um.

AA2.1 The device, kit, system, smartphone system, and method of any prior embodiments, wherein the analyte concentration areas have an average diameter in the range of 1 nm to 200 um.

AAA2.1 The device, kit, system, smartphone system, and method of any prior embodiments, wherein the concentrating protrusions have an average diameter in the range of 1 nm to 200 um.

A2.1.1 The device, kit, system, smartphone system, and method of any prior embodiments, wherein the particles have an average diameter in the range of 0.1 μm to 10 μm.

A2.1.2 The device, kit, system, smartphone system, and method of any prior embodiments, wherein the particles have an average diameter in the range of 1 nm to 500 nm.

A2.1.3 The device, kit, system, smartphone system, and method of any prior embodiments, wherein the particles have an average diameter in the range of to 0.5 μm to 30 μm.

A2.1.4 The device, kit, system, smartphone system, and method of any prior embodiments, wherein ratio between the spacing between the plates at the closed configuration and average dimeter of the particles is in the range of 1-100.

AA2.1.4 The device, kit, system, smartphone system, and method of any prior embodiments, wherein ratio between the spacing between the plates at the closed configuration and height of the analyte concentration area is in the range of 1-100.

AAA2.1.4 The device, kit, system, smartphone system, and method of any prior embodiments, wherein ratio between the spacing between the plates at the closed configuration and height of the concentrating protrusion is in the range of 1-100.

A2.2 The device, kit, system, smartphone system, and method of any prior embodiments, wherein the particles have an area density of 1 to $10^6$ per $mm^2$.

AA2.2 The device, kit, system, smartphone system, and method of any prior embodiments, wherein the analyte concentration areas have an area density of 1 to $10^6$ per $mm^2$.

AAA2.2 The device, kit, system, smartphone system, and method of any prior embodiments, wherein the concentrating protrusions have an area density of 1 to $10^6$ per $mm^2$.

A2.2.1 The device, kit, system, smartphone system, and method of any prior embodiments, wherein the particles have an area density of 1 to 1000 per $mm^2$.

A2.3 The device, kit, system, smartphone system, and method of any prior embodiments, wherein the particles are configured to amplify the signal in proximity to the particles, and have a signal amplification factor in the range of 1 to 10000.

A2.4 The device, kit, system, smartphone system, and method of any prior embodiments, wherein the detection antibody is configured to have a concentration in the layer of uniform thickness that is 1 to 1000 times higher than analyte concentration in the sample.

A3 The device, kit, system, smartphone system, and method of any prior embodiments, wherein the particles and the detection agent are on the same plate.

A3.1 The device, kit, system, smartphone system, and method of any prior embodiments, wherein the particles and the detection agent are on different plates.

A4 The device, kit, system, smartphone system, and method of any prior embodiments, wherein the analyte is selected from the group consisting of: cells, viruses, proteins, peptides, DNAs, RNAs, oligonucleotides, and any combination thereof.

A4.1 The device, kit, system, smartphone system, and method of any prior embodiments, wherein the analyte is C Reactive Protein (CRP).

A5.1 The device, kit, system, smartphone system, and method of any prior embodiments, wherein the capture agent is selected from the group consisting of: protein, peptide, peptidomimetics, streptavidin, biotin, oligonucleotide, oligonucleotide mimetics, any other affinity ligand and any combination thereof.

A5.1.1 The device, kit, system, smartphone system, and method of any prior embodiments, wherein the capture agent is an antibody.

A5.1.2 The device, kit, system, smartphone system, and method of any prior embodiments, wherein the capture antibody is an anti-C Reactive Protein (CRP) antibody.

A5.1.3 The device, kit, system, smartphone system, and method of any prior embodiments, wherein the capture agent has a concentration that is sufficient to detect the presence and/or measure the amount of the analyte.

A5.1.4 The device, kit, system, smartphone system, and method of any prior embodiments, wherein the capture agent has a concentration that is sufficient to immobilize the analyte.

A5.2 The device, kit, system, smartphone system, and method of any prior embodiments, wherein the detection agent is selected from the group consisting of: protein, peptide, peptidomimetics, streptavidin, biotin, oligonucleotide, oligonucleotide mimetics, any other affinity ligand and any combination thereof.

A5.2.1 The device, kit, system, smartphone system, and method of any prior embodiments, wherein the detection agent is an antibody.

A5.2.2 The device, kit, system, smartphone system, and method of any prior embodiments, wherein the detection antibody is an anti-CRP antibody.

A6 The device, kit, system, smartphone system, and method of any prior embodiments, wherein the particles are made of a material selected from the group consisting of: polystyrene, polypropylene, polycarbonate, PMMG, PC, COC, COP, glass, resin, aluminum, gold or other metal or any other material whose surface can be modified to be associated with the capture agent.

A6.1 The device, kit, system, smartphone system, and method of any prior embodiments, wherein the particles are treated with a protein stabilizer.

A6.2 The device, kit, system, smartphone system, and method of any prior embodiments, wherein the capture agent are conjugated with the particles.

A6.3 The device, kit, system, smartphone system, and method of any prior embodiments, wherein the particles are prepared by:
 (d) activating with N-Hydroxysuccinimide (NHS);
 (e) blocking with a BSA solution; and
 (f) incubating with a capture agent solution.

A7 The device, kit, system, smartphone system, and method of any prior embodiments, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

A7.1 The device, kit, system, smartphone system, and method of any prior embodiments, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

A7.2 The device, kit, system, smartphone system, and method of any prior embodiments, wherein the sample is an environmental gaseous sample from a source selected from the group consisting of: the air, underwater heat vents, industrial exhaust, vehicular exhaust, and any combination thereof.

A7.3 The device, kit, system, smartphone system, and method of any prior embodiments, wherein the sample is a foodstuff sample selected from the group consisting of: raw ingredients, cooked food, plant and animal sources of food, preprocessed food, and partially or fully processed food, and any combination thereof.

A8. The device, kit, system, smartphone system, and method of any prior embodiments, wherein the detection agent is a labeled agent.

A8.1 The device, kit, system, smartphone system, and method of any prior embodiments, wherein the detection agent is labeled with a fluorophore.

A8.1.1 The device, kit, system, smartphone system, and method of any prior embodiments, wherein the fluorophore is Cy5.

(Quencher)

A8.2 The device, kit, system, smartphone system, and method of any prior embodiments, wherein the particles are associated with a label, and wherein the detection agent is a quencher that is configured to quench signal of the particles-associated label when the detection agent is in proximity of the label.

A9. The device, kit, system, smartphone system, and method of any prior embodiments, wherein the detector detects the signal emanating from the analyte concentration areas or particles indicative of the presence and/or quantity of the analyte.

A9.1 The device, kit, system, smartphone system, and method of any prior embodiments, wherein the signal is:
  i. luminescence selected from photoluminescence, electroluminescence, and electrochemiluminescence;
  ii. light absorption, reflection, transmission, diffraction, scattering, or diffusion;
  iii. surface Raman scattering;
  iv. electrical impedance selected from resistance, capacitance, and inductance;
  v. magnetic relaxivity; or
  vi. any combination of i-v.

D2. The smartphone system of any prior embodiments, wherein the mobile communication device is configured to communicate test results to a medical professional, a medical facility or an insurance company.

D3. The smartphone system of any prior embodiments, wherein the mobile communication device is further configured to communicate information on the subject with the medical professional, medical facility or insurance company.

D4. The smartphone system of any prior embodiments, wherein the mobile communication device is configured to receive a prescription, diagnosis or a recommendation from a medical professional.

D5. The smartphone system of any prior embodiments, wherein the mobile communication device communicates with the remote location via a wifi or cellular network.

D6. The smartphone system of any prior embodiments, wherein the mobile communication device is a mobile phone.

E2 The method of any prior embodiments, wherein the sample contact sites are not washed before the imaging step (e).

E3 The method of any of embodiments 1-5, further comprising washing the sample contact area before the imaging step (e).

E4 The method of any prior embodiments, further comprising determining the presence of the analyte and/or measuring the amount of the analyte.

AE2.1 The method of embodiment AE2, wherein the calculated parameters comprise average signal intensity from all the particles that are analyzed.

AE2.2 The method of embodiment AE2, wherein the calculated parameters comprise highest signal intensity from all the particles that are analyzed.

AE2.3 The method of embodiment AE2, wherein the calculated parameters comprise signal intensity distribution from all the particles that are analyzed.

AE2.4 The method of embodiment AE2, wherein the calculated parameters comprise number of all the particles that are analyzed with signal intensity larger than a threshold;

AE2.5 The method of embodiment AE2, wherein the calculated parameters comprise average signal intensity from all the particles that are analyzed in a first area of the image.

AE2.6 The method of embodiment AE2, wherein the calculated parameters comprise highest signal intensity from all the particles that are analyzed in a first area of the image.

AE2.7 The method of embodiment AE2, wherein the calculated parameters comprise signal intensity distribution from all the particles that are analyzed in a first area of the image.

AE2.8 The method of embodiment AE2, wherein the calculated parameters comprise number of all the particles that are analyzed in a first area of the image with signal intensity larger than a threshold.

F1 The device, kit, system, smartphone system, and method of any prior embodiments wherein the analytes is the analyte in 5 detection of proteins, peptides, nucleic acids, synthetic compounds, and inorganic compounds.

F2 The device, kit, system, smartphone system, and method of any prior embodiments wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

F3 The device, kit, system, smartphone system, and method of any prior embodiments wherein the spacers have a shape of pillars and a ratio of the width to the height of the pillar is equal or larger than one.

F4 The method of any prior embodiment, wherein the sample that is deposited on one or both of the plates has an unknown volume.

F5 The device, kit, system, smartphone system, and method of any prior embodiments wherein the spacers have a shape of pillar, and the pillar has substantially uniform cross-section.

F6 The device, kit, system, smartphone system, and method of any prior embodiments wherein the samples are for the detection, purification and quantification of chemical compounds or biomolecules that correlates with the stage of certain diseases.

F7 The device, kit, system, smartphone system, and method of any prior embodiments wherein the samples is related to infectious and parasitic disease, injuries, cardiovascular disease, cancer, mental disorders, neuropsychiatric disorders, pulmonary diseases, renal diseases, and other and organic diseases.

F8 The device, kit, system, smartphone system, and method of any prior embodiments wherein the samples are related to the detection, purification and quantification of microorganism.

F9 The device, kit, system, smartphone system, and method of any prior embodiments wherein the samples is related to virus, fungus and bacteria from environment, e.g., water, soil, or biological samples.

F10 The device, kit, system, smartphone system, and method of any prior embodiments wherein the samples is related to the detection, quantification of chemical compounds or biological samples that pose hazard to food safety or national security, e.g. toxic waste, anthrax.

F11 The device, kit, system, smartphone system, and method of any prior embodiments wherein the samples are related to quantification of vital parameters in medical or physiological monitor.

F12 The device, kit, system, smartphone system, and method of any prior embodiments wherein the samples are related to glucose, blood, oxygen level, total blood count.

F13 The device, kit, system, smartphone system, and method of any prior embodiments wherein the samples are related to the detection and quantification of specific DNA or RNA from biosamples.

F14 The device, kit, system, smartphone system, and method of any prior embodiments wherein the samples are related to the sequencing and comparing of genetic sequences in DNA in the chromosomes and mitochondria for genome analysis.

F15 The device, kit, system, smartphone system, and method of any prior embodiments wherein the samples are related to detect reaction products, e.g., during synthesis or purification of pharmaceuticals.

F16 The device, kit, system, smartphone system, and method of any prior embodiments wherein the samples are cells, tissues, bodily fluids, and stool.

F17 The device, kit, system, smartphone system, and method of any prior embodiments wherein the sample is the sample in the detection of proteins, peptides, nucleic acids, synthetic compounds, inorganic compounds.

F18 The device, kit, system, smartphone system, and method of any prior embodiments wherein the sample is the sample in the fields of human, veterinary, agriculture, foods, environments, and drug testing.

F19 The method or device of any prior embodiment, wherein the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, or bone.

Example-1

Homogeneous QMAX Immunoassay—for Human CRP (C-Reactive Protein)

Here we describe an experiment of homogeneous QMAX immunoassay for human CRP according to one embodiment of the present invention.

In this experiment, the device for the immunoassay comprises a first plate and a second plate. Conventional glass slide was used as the first plate and X-plate with 10 μm spacer as the second plate. Microbeads were coated on the first plate, and the microbeads (Pierce, 10 μm in diameter) were NHS activated and conjugated to capture antibody (anti-CRP mouse monoclonal, Fitzgerald). A fluorescence microscope was used as the detector. The average distance between two neighboring beads is about 30 um to 50 um.

The experiment was conducted according to the following procedures:

1. Conjugation of capture antibody to beads. NHS activated beads (Pierce, 10 μm in diameter) were conjugated to anti-CRP mouse monoclonal capture antibody (Fitzgerald) according to manufacturer's protocol.
2. Blocking of beads. The antibody conjugated beads were blocked by 4% BSA in PBS at 4° C. over night and washed by PBST for 6 times prior to use.
3. Coating first plate. 1 μL of beads from Step 2 (beads concentration $10^7$-$10^8$/mL) were dropped on glass slide (Fisher Scientific) and air dried at room temperature.
4. Homogeneous QMAX assay. 1 μL of CRP analyte (Fitzgerald) at the concentration of 10 μg/mL and 1 μL of Cy5-labeled anti-CRP mouse monoclonal detection antibody (Fitzgerald) were dropped onto the area of coated beads on the glass slide. Different concentrations of Cy5 labeled anti-CRP detection antibody (A, 800 μg/mL; B, 100 μg/mL; C, 50 μg/mL; D, 25 μg/mL and E, 0 μg/mL) were tested separately. The mixture was immediately covered by X-plate (second plate) with 10 μm spacer and incubated for 30 seconds at room temperature.
5. Imaging. Without washing, the fluorescent images were taken by the fluorescence microscope (Ex 640 nm, Em 670-690 nm).

Figure 12:
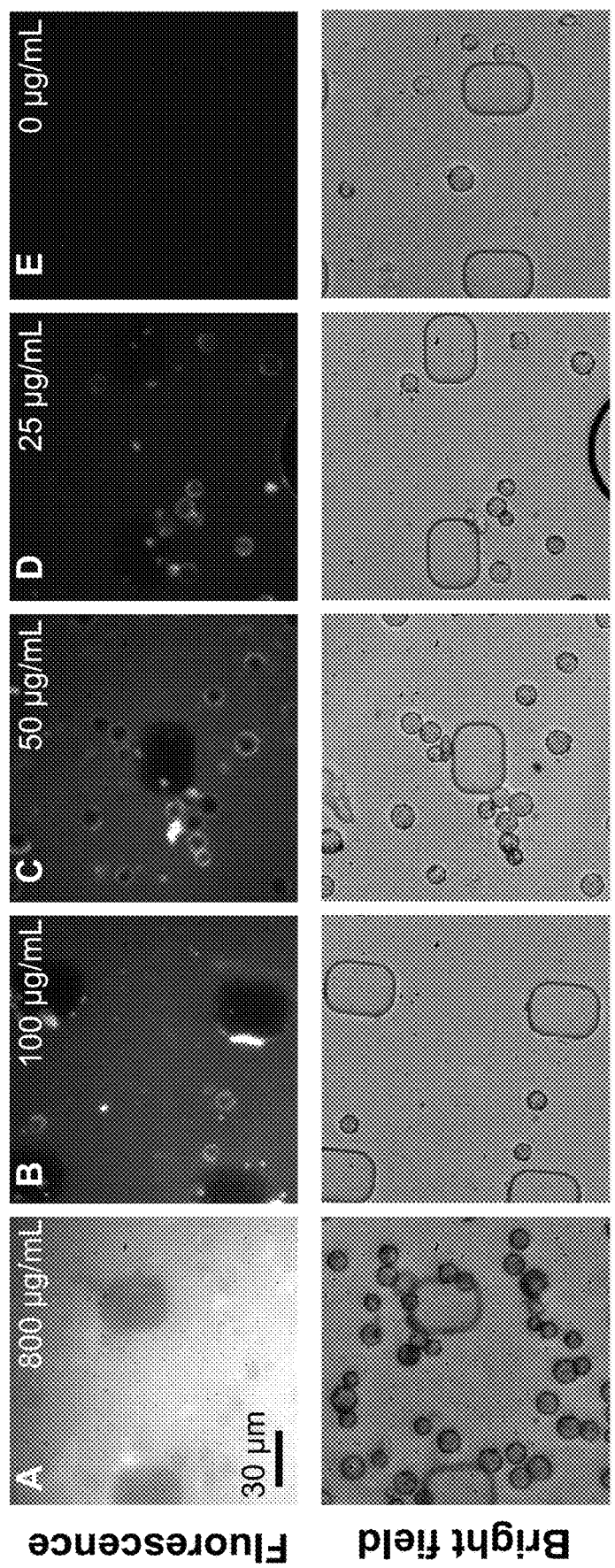
FIG. 12 shows exemplary fluorescence and bright-field images of the fluorescent stained beads inside a sample (i.e. solution) sandwiched between two plates.

FIG. 12 shows exemplary pictures of the fluorescent signals with the QMAX device and the conjugated beads, as well as their corresponding bright-field images.

As shown in the figure, we found that, in this exemplary experiment, the concentration of the fluorophore-labeled detection antibody is critical for the homogeneous assay. When it is high enough to create a high fluorescence background (FIG. 12A, detection antibody concentration: 800 ug/mL), the true assay signal from the beads, although locally concentrated around the beads, is not distinguishable from the background in liquid.

In contrast, when the detection antibody is at relatively low concentrations (FIGS. 12B-D, 100 ug/mL, 50 ug/mL, 25 ug/mL, respectively), the background created by the free (unbound) fluorophore labeled antibody in liquid is low enough so that the assay signals on the beads are distinguishable. It is worth noting that when the concentration of detection antibody is too low, there will be not enough detection antibody to be captured onto the beads, which may result in poor contrast to the background.

Example-2

Beads-Enhanced Speedy Test (BEST) Structure Examples
1. Exemplary Embodiments of Beads-Enhanced Speedy Test (BEST)—Beads Based:

One exemplary device comprises a first plate, a second plate, an array of spacers on the second plate, beads and concentration areas.

First plate: 24 mm×32 mm size, 1 mm thick plastic (as acrylic or polystyrene) or glass Second plate: 22 mm×25 mm size, 175 um thick plastic (as acrylic or polystyrene) with an array of pillar spacers on one side. The pillar spacers are 30×40 um in lateral size, and 10 um in height, and the inter-spacer distance is 80 um for the array.

Beads: 10 um in diameter plastic beads (as acrylic or polystyrene) with an area concentration of 100/mm2 to 1000/mm2, which are uniformly pre-dried on the second plate.

Concentration areas: on the surface of all the beads

2. Exemplary Embodiments of Beads-Enhanced Speedy Test (BEST)—Beads Based:

Another exemplary device comprises a first plate, a second plate, spacer array on the second plate, beads and concentration areas.

First plate: 24 mm×32 mm size, 1 mm thick plastic (as acrylic or polystyrene) or glass Second plate: 22 mm×25 mm size, 50 um thick plastic (as acrylic or polystyrene) with an array of pillar spacers on one side. The pillar spacers are 20×20 um in lateral size, and 20 um in height, and the inter-spacer distance is 150 um for the array.

Beads: 20 um in diameter beads with metal surface (as gold or silver) with an area concentration of 100/mm2 to 1000/mm2, which are uniformly pre-dried on the second plate.

Concentration area: on the surface of all the beads

3. Exemplary Embodiments of Beads-Enhanced Speedy Test (BEST)—Beads Based:

Another exemplary device comprises a first plate, a second plate, a pit array on the first plate, an array of spacers on the second plate, beads and concentration areas.

First plate: 24 mm×32 mm size, 1 mm thick plastic (as acrylic or polystyrene) or glass with pit array on one side. The pits are 12 um×12 um in lateral size, and 6 um in depth, and the inter-pit distance is 50 um.

Second plate: 22 mm×25 mm size, 175 um thick plastic (as acrylic or polystyrene) with an array of pillar spacers on one side. The pillar spacers are 20×20 um in lateral size, and 10 um in height, and the inter-spacer distance is 100 um.

Beads: 10 um in diameter beads with or without metal surface (gold or silver) with an area concentration of 100/mm2 to 1000/mm2, which are uniformly pre-dried on the first plate and mostly inside the pits.

Concentration area: on the surface of all the beads

4. Exemplary Embodiments of Beads-Enhanced Speedy Test (BEST)—Protrusions Based:

Another exemplary device comprises a first plate, a second plate, an array of first type of pillars (spacers) and an array of second type of pillars (protrusions) on the first plate, and concentration areas.

First plate: 24 mm×32 mm size, 1 mm thick plastic (as acrylic or polystyrene) or glass with the two pillar arrays on one side. The first type of pillars are 20×20 um in lateral size, and 10 um in height, and the inter-pillar distance is 150 um. The second type of pillars are 10 urn in lateral diameter, and 8 um in height, and the inter-pillar distance is 50 um. The two pillar arrays are intermingled with one another.

Second plate: 22 mm×25 mm size, 150 um thick plastic (as acrylic or polystyrene) with flat surface.

Concentration area: on the top surface of the protrusions. Or on the side surfaces of the protrusions. Or on all the surfaces of the protrusions.

5. Exemplary Embodiments of Beads-Enhanced Speedy Test (BEST)—Protrusions Based:

Another exemplary device comprises a first plate, a second plate, an array of first type of pillars (spacers) and an array of second type of pillars (protrusions) on the first plate, and concentration areas.

First plate: 24 mm×32 mm size, 1 mm thick plastic (as acrylic or polystyrene) or glass with the two pillar arrays on one side. The first type pillars are 30×30 um in lateral size, and 15 um in height, and the inter-pillar distance is 120 um. The second type pillars are 15 um in lateral diameter, and 10 um in height, and the inter-pillar distance is 60 um. The two pillar arrays are intermingled with one another The second type pillars are coated with gold on all the surfaces.

Second plate: 22 mm×25 mm size, 100 um thick plastic (as acrylic or polystyrene) with flat surface.

Concentration area: on the top surface of the protrusions. Or on the side surfaces of the protrusions. Or on all the surfaces of the protrusions.

6. Exemplary Embodiments of Beads-Enhanced Speedy Test (BEST)—Protrusions Based:

Another exemplary device comprises a first plate, a second plate, an array of first type of pillars (protrusions) on the first plate, an array of second type of pillars (spacers) on the second plate, and concentration areas.

First plate: 24 mm×32 mm size, 1 mm thick plastic (as acrylic or polystyrene) or glass with the protrusion pillar array on one side. The protrusion pillars are 10 um pillar in lateral diameter, and 5 um in height, and the inter-pillar distance is 50 um.

Second plate: 22 mm×25 mm size, 50 um thick plastic (as acrylic or polystyrene) with flat surface. The spacer pillars are 20×20 um in lateral size, and 10 um in height, and the inter-pillar distance is 150 um.

Concentration area: on the top surface of the protrusions. Or on the side surfaces of the protrusions. Or on all the surfaces of the protrusions.

In all the above exemplary devices of this section, the side wall(s) of the protrusion pillars has/have a slope of 90°, 80°, 70°, 60°, 50°, 40°, 30°, 20°, or in a range between any of these two values.

8. Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S.

Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

What is claimed is:

1. A device for a homogeneous assay, comprising:
    a first plate, a second plate, spacers, a plurality of particles, and a capture agent, wherein:
    (i) the first and second plates are movable relative to each other into different configurations, including an open configuration and a closed configuration;
    (ii) each of the plates has, on its respective inner surface, a sample contact area for contacting a sample suspected of containing an analyte;
    (iii) the spacers are fixed on the inner surface of the first plate, at least one of the spacers is inside the sample contact area of the first plate, the spacers have a predetermined uniform height that is equal to 100 μm or less;
    (iv) the capture agent is immobilized on a surface of the plurality of particles, wherein the capture agent is capable of specifically binding and immobilizing the analyte; and (v) the plurality of particles are (a) distributed on the sample contact area of the first plate, except the areas occupied by the spacers, and (b) are temporarily or permanently fixed on the first plate;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of uniform thickness, the uniform thickness of the layer is confined by the inner surfaces of the plates and is regulated by the plates and the spacers.

2. The device of claim 1, wherein:
(i) one or both of the first and second plates are flexible;
(ii) each of the spacers has a pillar shape and a flat top surface, and the spacers have a predetermined uniform height and a predetermined inter-spacer distance;
(iii) the fourth power of the inter-spacer-distance (ISD) divided by the thickness (h) and the Young's modulus (E) of the flexible plate ($ISD^4/(hE)$) is $5 \times 10^6$ $\mu m^3/GPa$ or less; and
(iv) the thickness of the plate times the Young's modulus of the flexible plate is in the range 60 to 750 GPa-μm.

3. The device of claim 1, wherein the distribution of the plurality of particles on the first plate is random.

4. The device of claim 1, wherein the plurality of particles are fixed on the plate and has periodic distribution.

5. The device of claim 1, wherein each of the spacers has a flat top.

6. The device of claim 1, wherein the plurality of particles are temporarily fixed on the first plate, and in an open configuration the sample is deposited on the first plate before the two plates are brought into the closed configuration.

7. The device of claim 1, wherein a thickness of the spacers is configured such that, in a closed configuration, for a certain concentration of the analytes in the sample, at least one area of the sample layer that contains one of the particle becomes optically distinguishable, when viewed outside of the sample layer, from its neighboring area that does not contain a particle.

8. The device of claim 1, wherein the plates are compressed by a compression force that is provided by human hand.

9. The device of claim 1, wherein the diameter of one or more of the plurality of particles is equal to the height of the spacers.

10. The device of claim 1, wherein the height of the spacers is about 10 μm.

11. The device of claim 1, wherein the height of the spacers is about 5 μm.

12. The device of claim 1, wherein the height of the spacers is between about 0.1 μm and about 15 μm.

13. The device of claim 1, wherein the height of the spacers is between about 0.1 μm and about 3 μm.

14. The device of claim 1, wherein at least a portion of the inner surface of one plate or both plates is hydrophilic.

15. The device of claim 1, wherein the inter-spacer distance is periodic.

16. The device of claim 1, wherein the sample is a deposition directly from a subject to the plate without using any transferring devices.

17. The device of claim 1, wherein the inter-spacer distance (ISD) is equal or less than about 120 μm (micrometer).

18. The device of claim 1, wherein the inter-spacer distance (ISD) is equal or less than about 100 μm.

19. The device of claim 2, wherein the inter-spacer distance (ISD) is equal or less than about 120 μm (micrometer).

20. The device of claim 2, wherein the inter-spacer distance (ISD) is equal or less than about 100 μm (micrometer).

21. The device of claim 2, wherein the fourth power of the inter-spacer-distance (ISD) divided by the thickness (h) and the Young's modulus (E) of the flexible plate ($ISD^4/(hE)$) is $1 \times 10^6$ $\mu m^3/GPa$ or less.

22. The device of claim 2, wherein the fourth power of the inter-spacer-distance (ISD) divided by the thickness (h) and the Young's modulus (E) of the flexible plate ($ISD^4/(hE)$) is $5 \times 10^5$ $\mu m^3/GPa$ or less.

23. The device of claim 1, wherein the spacers have pillar shape, a flat top surface, a predetermined uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

24. The device of claim 1, wherein the spacers have pillar shape, a flat top surface, a predetermined uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5 \times 10^6$ $\mu m^3/GPa$ or less.

25. The device of claim 2, wherein the ratio of the inter-spacer distance of the spacers to the average width of the spacer is 2 or larger, and the filling factor of the spacers multiplied by the Young's modulus of the spacers is 2 MPa or larger.

26. A method of performing a homogeneous assay, comprising the steps of:
(a) obtaining a sample suspected of containing an analyte;
(b) obtaining the device of claim 1, wherein the capture agent is capable of specifically binding a binding site of the analyte;
(c) having optical labels on at least a part of the sample contact areas of the device, wherein the optical labels are capable of binding to the analytes;
(d) depositing the sample on one or both of the plates when the plates are in an open configuration, wherein in an open configuration;
(e) after (d), bringing the two plates together and pressing the plates into a closed configuration, at least part of the sample is compressed by the two plates into a layer of highly uniform thickness, the uniform thickness of the layer is confined by the inner surfaces of the plates and is regulated by the plates and the spacers;
(f) while the plates are in the closed configuration, analyzing the analyte in the layer of uniform thickness, wherein the analyzing comprises:
(i) measuring, from outside of the sample layer, the total light signal from (a) a particle area that is an area of the sample layer that contains one particle and from (b) a surrounding area that is the area of the sample layer which is around the particle area, wherein the surrounding area is 50 D within the edge of the particle, wherein the D is the diameter of the particle; and (ii) measuring the total light signal from each of the particle area and the surrounding area of at least two different particle areas.

27. The method of claim 26, wherein the particle area for the total light signal measurement has the same area as the particle diameter.

28. The method of claim 26, wherein the particle area for the total light signal measurement is smaller than the area defined by the particle diameter.

29. The method of claim 26, wherein the analyzing the analyte in the uniform sample layer comprises averaging of the total light signal from each area.

30. The method of claim 26, wherein the analyzing the analyte in the uniform sample layer comprises (i) taking a ratio of the total light signal of each particle area to that of its surrounding area, and (ii) averaging the ratio of all particle area and surround area pairs.

31. The method of claim 26, wherein the time from the end of the sample deposition to the end of the plates being pressed into the closed configuration is less than 15 seconds.

32. The method of claim 26, wherein the time from the end of the sample deposition to the end of the plates being pressed into the closed configuration is less than 5 seconds.

33. An apparatus for homogenous assaying an analyte in a sample, comprising:
(i) the device of claim 1; and
(ii) one or more imagers that image at least a part of the sample contact area.

34. A smartphone system for homogeneous assay, comprising:
(a) the device of claim 1;
(b) a mobile communication device that comprises:
(i) one or a plurality of cameras for detecting and/or imaging the sample;
(ii) electronics, signal processors, hardware and software for receiving and/or processing the detected signal and/or the image(s) of the sample and for remote communication; and
(c) an adaptor that is configured to accommodate the device that is in the closed configuration and be engageable to the mobile communication device;
wherein when engaged with the mobile communication device, the adaptor is configured to facilitate the detection and/or imaging of the analyte in the sample.

35. The smartphone system, of claim 34, wherein the first and second particles are different.

36. The smartphone system, of claim 34, wherein the first and second particles are different in their sizes.

37. The smartphone system, of claim 34, wherein the first and second particles are different in their optical properties selected from the group consisting of: photoluminescence, electroluminescence, and electrochemiluminescence, light absorption, reflection, transmission, diffraction, scattering, diffusion, surface Raman scattering, and any combination thereof.

38. The smartphone system, of claim 34, wherein the first and second particles are different in their electric densities.

39. The smartphone system, of claim 34, wherein the first and second particles are the same, and wherein the signals from the first and second analytes are different.

40. A system for rapid homogeneous assay, comprising:
(a) the device of claim 1; and
(b) a detector that detects signals from the capture agent-bound analyte indicative of the presence and/or quantity of the analyte in the layer of uniform thickness.

41. A smartphone system for rapid homogeneous assay, comprising:
(a) the device of claim 1;
(b) a mobile communication device that comprises:
i. one or a plurality of cameras for detecting and/or imaging the sample;
ii. electronics, signal processors, hardware and software for receiving and/or processing the detected signal and/or the image of the sample and for remote communication; and
(c) an adaptor that is configured to hold the closed device and engageable to mobile communication device;
wherein when engaged with the mobile communication device, the adaptor is configured to facilitate the detection and/or imaging of the analyte in the sample at the closed configuration.

42. A method of performing a rapid homogeneous assay, comprising the steps of:
(a) obtaining a sample suspected of containing an analyte;
(b) obtaining the device of claim 1;
(c) depositing the sample on one or both of the plates when the plates are in the open configuration;
(d) after (c), bringing the two plates together and pressing the plates into the closed configuration; and
(e) while the plates are at the closed configuration, detecting and analyzing the analyte in the layer of uniform thickness.

43. A method of analyzing the image for a rapid homogeneous assay, comprising the steps of:
(a) obtaining an image of the signal in claim 40 at the closed configuration, wherein the image is selected from the group consisting of bright field image, dark field image, fluorescence image, and phosphorescence image;
(b) analyzing the image, identifying particles in the image, and extracting information of particles size, signal intensity of particles, distance between particles, distribution of particles, and number of particles; and
(c) deducing analyte concentration by analyzing the extracted information from step (b) and calculating parameters of the particles.

44. A method of performing a rapid homogeneous assay, comprising the steps of:
(a) obtaining a sample suspected of containing an analyte;
(b) obtaining the device of claim 1;
(c) depositing the sample on one or both of the plates when the plates are in the open configuration;
(d) after (c), bringing the two plates together and pressing the plates into the closed configuration; and
(e) after step (d), incubating the assay for a time equal to or longer than an intended assay time, detecting and analyzing the analyte in the layer of uniform thickness.

45. The method of claim 44, wherein the intended assay time is in the range of 0.1-240 sec.

46. The method of claim 44, wherein the intended assay time is in the range of 1-60 sec.

47. The method of claim 44, wherein the intended assay time is equal to or less than 30 sec.

48. The method of claim 44, wherein the intended assay time is equal to or less than 10 sec.

49. The method of claim 44, wherein the intended assay time is equal to or less than 5 sec.

50. The method of claim 44, wherein the intended assay time is equal to or less than 1 sec.

51. The device of claim 1, wherein the analyte is labeled by a detection agent that selectively binds to the analyte and is associated with a label.

52. The device of claim 51, wherein the detection agent is coated on the inner surface(s) of one or both of the plates, and is configured to, upon contacting the sample, be dissolved and diffuse in the sample.

53. The device of claim 51, wherein the detection agent is pre-loaded into the sample before the sample is deposited on the plate(s).

54. The device of claim 51, wherein the capture agent and the detection agent are configured to bind to the analyte at different locations thereof and form capture agent-analyte-detection agent sandwich.

55. The device of claim 1, wherein the analyte competes with a detection agent to bind to the capture agent, and wherein the detection agent is labeled.

56. The device of claim 1, wherein one or both of the plates comprise, on the respective inner surface, a signal amplification surface that amplify a signal in proximity to the amplification surface.

57. The device of claim 1, wherein the particles are the spacers that regulate the thickness of the layer at the closed configuration.

58. The device of claim 1, wherein the particles are micro- or nano-particles having an average diameter in the range of 1 nm to 200 μm.

59. The device of claim 1, wherein the particles have an average diameter in the range of 0.1 μm to 10 μm.

60. The device of claim 1, wherein the particles have an average diameter in the range of 1 nm to 500 nm.

61. The device of claim 1, wherein the particles have an average diameter in the range of to 0.5 μm to 30 μm.

62. The device of claim 1, wherein ratio between the spacing between the plates at the closed configuration and average diameter of the particles is in the range of 1-100.

63. The device of claim 1, wherein the particles have an area density of 1 to $10^6$ per $mm_2$.

64. The device of claim 1, wherein the particles have an area density of 1 to 1000 per $mm^2$.

65. The device of claim 1, wherein the particles are configured to amplify a signal in proximity to the particles and have a signal amplification factor in the range of 1 to 10000.

66. The device of claim 51, wherein the detection agent is configured to have a concentration in the layer of uniform thickness that is 1 to 1000 times higher than analyte concentration in the sample.

67. The device of claim 51, wherein the particles and the detection agent are on the same plate.

68. The device of claim 51, wherein the particles and the detection agent are on different plates.

69. The device of claim 1, wherein the analyte is selected from the group consisting of: cells, viruses, proteins, peptides, DNAs, RNAs, oligonucleotides, and any combination thereof.

70. The device of claim 1, wherein the analyte is C Reactive Protein (CRP).

71. The device of claim 1, wherein the capture agent is selected from the group consisting of: protein, peptide, peptidomimetics, streptavidin, biotin, oligonucleotide, oligonucleotide mimetics, any other affinity ligand and any combination thereof.

72. The device of claim 1, wherein the capture agent is an antibody.

73. The device of claim 1, wherein the capture agent is an anti-C Reactive Protein (CRP) antibody.

74. The device of claim 1, wherein the capture agent has a concentration that is sufficient to detect the presence and/or measure the amount of the analyte.

75. The device of claim 1, wherein the capture agent has a concentration that is sufficient to immobilize the analyte.

76. The device of claim 51, wherein the detection agent is selected from the group consisting of: protein, peptide, peptidomimetics, streptavidin, biotin, oligonucleotide, oligonucleotide mimetics, any other affinity ligand and any combination thereof.

77. The device of claim 51, wherein the detection agent is an antibody.

78. The device of claim 51, wherein the detection agent is an anti-CRP antibody.

79. The device of claim 1, wherein the particles are made of a material selected from the group consisting of: polystyrene, polypropylene, polycarbonate, PMMG, PC, COC, COP, glass, resin, aluminum, gold or other metal or any other material whose surface can be modified to be associated with the capture agent.

80. The device of claim 1, wherein the particles are treated with a protein stabilizer.

81. The device of claim 1, wherein the capture agent is conjugated with the particles.

82. The device of claim 1, wherein the particles are prepared by:
(a) activating with N-Hydroxysuccinimide (NHS);
(b) blocking with a BSA solution; and
(c) incubating with a capture agent solution.

83. The device of claim 1, wherein the sample is made from a biological sample selected from the group consisting of: amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

84. The device of claim 1, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

85. The device of claim 1, wherein the sample is an environmental gaseous sample from a source selected from the group consisting of: the air, underwater heat vents, industrial exhaust, vehicular exhaust, and any combination thereof.

86. The device of claim 1, wherein the sample is a foodstuff sample selected from the group consisting of: raw ingredients, cooked food, plant and animal sources of food, preprocessed food, and partially or fully processed food, and any combination thereof.

87. The device of claim 51, wherein the detection agent is a labeled agent.

88. The device of claim 51, wherein the detection agent is labeled with a fluorophore.

89. The device of claim 88, wherein the fluorophore is Cy5.

90. The device of claim 51, wherein the particles are associated with a label, and wherein the detection agent is a quencher that is configured to quench signal of the particles-associated label when the detection agent is in proximity of the label.

91. The system of claim 40, wherein the detector detects the signal emanating from the analyte concentration areas or particles indicative of the presence and/or quantity of the analyte.

92. The system of claim 40, wherein the signal is:
(i) luminescence selected from photoluminescence, electroluminescence, and electrochemiluminescence;
(ii) light absorption, reflection, transmission, diffraction, scattering, or diffusion;
(iii) surface Raman scattering;
(iv) electrical impedance selected from resistance, capacitance, and inductance;
(v) magnetic relaxivity; or
(vi) any combination of i-v.

93. The smartphone system of claim 34, wherein the mobile communication device is configured to communicate test results to a medical professional, a medical facility or an insurance company.

94. The smartphone system of claim 34, wherein the mobile communication device is further configured to communicate information on the subject with a medical professional, medical facility or insurance company.

95. The smartphone system of claim 34, wherein the mobile communication device is configured to receive a prescription, diagnosis or a recommendation from a medical professional.

96. The smartphone system of claim 34, wherein the mobile communication device communicates with a remote location via a wifi or cellular network.

97. The smartphone system of claim 34, wherein the mobile communication device is a mobile phone.

98. The method of claim 42, wherein the sample contact areas are not washed before step (e).

99. The method of claim 42, further comprising washing the sample contact area before step (e).

100. The method of claim 42, further comprising determining the presence of the analyte and/or measuring the amount of the analyte.

101. The method of claim 43, wherein the calculated parameters comprise average signal intensity from all the particles that are analyzed.

102. The method of claim 43, wherein the calculated parameters comprise highest signal intensity from all the particles that are analyzed.

103. The method of claim 43, wherein the calculated parameters comprise signal intensity distribution from all the particles that are analyzed.

104. The method of claim 43, wherein the calculated parameters comprise number of all the particles that are analyzed with signal intensity larger than a threshold.

105. The method of claim 43, wherein the calculated parameters comprise average signal intensity from all the particles that are analyzed in a first area of the image.

106. The method of claim 43, wherein the calculated parameters comprise highest signal intensity from all the particles that are analyzed in a first area of the image.

107. The method of claim 43, wherein the calculated parameters comprise signal intensity distribution from all the particles that are analyzed in a first area of the image.

108. The method of claim 43, wherein the calculated parameters comprise number of all the particles that are analyzed in a first area of the image with signal intensity larger than a threshold.

109. The device of claim 1, wherein the analyte is the analyte in detection of proteins, peptides, nucleic acids, synthetic compounds, and inorganic compounds.

110. The device of claim 1, wherein the sample is a biological sample selected from amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

111. The device of claim 1, wherein the spacers have a shape of pillars and a ratio of the width to the height of the pillar is equal or larger than one.

112. The method of claim 42, wherein the sample that is deposited on one or both of the plates has an unknown volume.

113. The device of claim 1, wherein the spacers have a shape of pillar, and the pillar has uniform cross-section.

114. The device of claim 1, wherein the sample is for the detection, purification and quantification of chemical compounds or biomolecules that correlates with the stage of certain diseases.

115. The device of claim 1, wherein the sample is related to an infectious or parasitic disease, injuries, cardiovascular disease, cancer, mental disorders, neuropsychiatric disorders, pulmonary diseases, renal diseases, or other organic diseases.

116. The device of claim 1, wherein the sample is related to the detection, purification and quantification of microorganism.

117. The device of claim 1, wherein the sample is related to virus, fungus and bacteria from an environment or a biological sample.

118. The device of claim 1, wherein the sample is related to the detection, quantification of chemical compounds or biological samples that pose hazard to food safety or national security.

119. The device of claim 1, wherein the sample is related to quantification of vital parameters in medical or physiological monitor.

120. The device of claim 1, wherein the sample is related to glucose, blood, oxygen level, total blood count.

121. The device of claim 1, wherein the sample is related to the detection and quantification of specific DNA or RNA from biosamples.

122. Device of claim 1, wherein the sample is related to the sequencing and comparing of genetic sequences in DNA in the chromosomes and mitochondria for genome analysis.

123. The device of claim 1, wherein the sample is cells, tissues, bodily fluids, and stool.

124. The device of claim 1, wherein the sample is the sample in the detection of proteins, peptides, nucleic acids, synthetic compounds, inorganic compounds.

125. The device of claim 1, wherein the sample is the sample in the fields of human, veterinary, agriculture, foods, environments, and drug testing.

126. The device of claim 1, wherein the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, or bone.

127. The device of claim 1, further comprising a detection agent on one of the first and second plates, wherein the detection agent is configured to bind to the analyte and form a capture agent-analyte-detection agent sandwich.

128. The device of claim 1, further comprising a labeled detection agent, wherein a unlabeled analyte competes with the labeled detection agent to bind to the capture agent.

129. The device of claim 1, further comprising a camera for imaging the sample.

130. The device of claim 1, further comprising a second set of particles that is different from the plurality of particles in the first plate in shape, size, optical property, or any combination thereof, wherein the second set of particles has a second capture agent immobilized on the surface of the second set of particles, wherein the second capture agent is capable of specifically binding and immobilizing a second analyte.

131. The device of claim 1, further comprising a detection agent, wherein the detection agent and the plurality of particles are on different plates.

132. The device of claim 1, further comprising a detector that images an optical signal of the sample, where the image comprises fluorescence image, bring field image, or a combination.

133. The device of claim 1, further comprising a label that attached to the analyte.

134. The device of claim 2, further comprising a detection agent on one of the first and second plates, wherein the detection agent is configured to bind to the analyte and form a capture agent-analyte-detection agent sandwich.

135. The device of claim 2, further comprising a labeled detection agent, wherein a unlabeled analyte competes with the labeled detection agent to bind to the capture agent.

136. The device of claim 2, further comprising a camera for imaging the sample.

137. The device of claim 2, further comprising a second set of particles that is different from the plurality of particles in the first plate in shape, size, optical property, or any combination thereof, wherein the second set of particles has a second capture agent immobilized on the surface of the second set of particles, wherein the second capture agent is capable of specifically binding and immobilizing a second analyte.

138. The device of claim 2, further comprising a detection agent, wherein the detection agent and the plurality of particles are on different plates.

139. The device of claim 2, further comprising a detector that images an optical signal of the sample, where the image comprises fluorescence image, bring field image, or a combination.

140. The device of claim 2, further comprising a label that attached to the analyte.

141. The device of claim 2, wherein the diameter of one or more of the plurality of particles is equal to the height of the spacers.

142. The device of claim 2, wherein the height of the spacers is about 10 µm.

143. The device of claim 2, wherein the height of the spacers is about 5 µm.

144. The device of claim 2, wherein the height of the spacers is between about 0.1 µm and about 15 µm.

145. The device of claim 2, wherein the height of the spacers is between about 0.1 µm and about 3 µm.

146. The device of claim 2, wherein the inter-spacer distance is periodic.

147. The device of claim 1, wherein the plurality of particles comprises first particles and second particles, and the capture agent comprises a first capture agent and a second capture agent,
wherein the first and second particles have first and second capture agents immobilized thereon, respectively; and
wherein the first and second capture agents are capable of binding to and immobilizing the first and second analytes, respectively.

148. The device of claim 1, wherein one or both of the plates further comprise, on the respective inner surface, a detection agent that is configured to, upon contacting the sample, be dissolved in the sample and bind to the analyte;
wherein the capture agent and the detection agent are configured to bind to the analyte at different locations thereof and to form a capture agent-analyte-detection agent sandwich that is immobilized to the particle; and
wherein the particles, the capture agent, and the detection agent are configured to render signal from the particle-associated capture agent-analyte-detection agent sandwich distinguishable from signal of free detection agent in the layer of uniform thickness.

149. The method of claim 26, wherein the spacers have a height that is equal to or less than 3 times of a diffusion parameter,
wherein the diffusion parameter is square root of an intended assay time multiplying diffusion constant of the analyte in the sample and wherein the intended assay time is equal to or less than 240 seconds, and
wherein an average distance between two neighboring particles is equal to or less than 2 times of the diffusion parameter.

150. The method of claim 26, wherein the ratio of the spacers' height versus the diffusion parameter is in the range of 0.01-2.

151. The method of claim 149, wherein the ratio of the spacers' height versus the diffusion parameter is in the range of 0.1-1.5.

152. The method of claim 149, wherein the ratio of the spacers' height versus the diffusion parameter is in the range of 0.01-0.5.

153. The method of claim 149, wherein the ratio of the spacers' height versus the diffusion parameter is in the range of 0.01-0.2.

154. The method of claim 149, wherein the ratio of the spacers' height versus the diffusion parameter is in the range of 0.01-0.1.

155. The method of claim 149, wherein the ratio of the average distance between two neighboring particles versus the diffusion parameter is in the range of 0.01-2, and the ratio of the spacers' height versus the diffusion parameter is in the range of 0.01-1.

156. The method of claim 149, wherein the ratio of the average distance between two neighboring particles versus the diffusion parameter is in the range of 0.01-4, and the ratio of the spacers' height versus the diffusion parameter is in the range of 0.01-1.

157. The method of claim 149, wherein the ratio of the average distance between two neighboring particles versus the diffusion parameter is in the range of 0.01-0.5, the ratio of the spacers' height versus the diffusion parameter is in the range of 0.01-0.2, and the intended assay time is equal to or less than 120 sec.

158. The method of claim 149, wherein the ratio of the average distance between two neighboring particles versus the diffusion parameter is in the range of 0.01-1; the ratio of the spacers' height versus the diffusion parameter is in the range of 0.01-0.5, and the intended assay time is equal to or less than 60 sec.

159. The method of claim 149, wherein the ratio of the average distance between two neighboring particles versus the diffusion parameter is in the range of 0.01-2; the ratio of the spacers' height versus the diffusion parameter is in the range of 0.01-1; and the intended assay time is equal to or less than 30 sec.

160. The method of claim 149, wherein the ratio of the average distance between two neighboring particles versus the diffusion parameter is in the range of 0.01-4; the ratio of the spacers' height versus the diffusion parameter is in the range of 0.01-1; and the intended assay time is equal to or less than 30 sec.

* * * * *